(12) United States Patent
Arber et al.

(10) Patent No.: US 11,219,636 B2
(45) Date of Patent: Jan. 11, 2022

(54) COMPOSITIONS AND METHODS FOR TREATING CANCER

(71) Applicant: The Medical Research, Infrastructure and Health Services Fund of the Tel Aviv Medical Center, Tel-Aviv (IL)

(72) Inventors: Nadir Arber, Tel-Aviv (IL); Shiran Shapira, Petach-Tikva (IL); Dina Kazanov, Rishon-LeZion (IL)

(73) Assignee: THE MEDICAL RESEARCH, INFRASTRUCTURE AND HEALTH SERVICES FUND OF THE TEL AVIV MEDICAL CENTER, Tel-Aviv (IL)

(*) Notice: Subject to any disclaimer, the term of this patent is extended or adjusted under 35 U.S.C. 154(b) by 324 days.

(21) Appl. No.: 15/574,855

(22) PCT Filed: May 17, 2016

(86) PCT No.: PCT/IL2016/050522
§ 371 (c)(1),
(2) Date: Nov. 17, 2017

(87) PCT Pub. No.: WO2016/185471
PCT Pub. Date: Nov. 24, 2016

(65) Prior Publication Data
US 2018/0161358 A1 Jun. 14, 2018

Related U.S. Application Data

(60) Provisional application No. 62/162,765, filed on May 17, 2015.

(51) Int. Cl.
| A61K 48/00 | (2006.01) |
| A61K 38/16 | (2006.01) |
| C12N 15/07 | (2006.01) |
| A61P 35/00 | (2006.01) |
| A61K 31/713 | (2006.01) |
| A61K 45/06 | (2006.01) |
| C12N 15/86 | (2006.01) |
| C12N 15/63 | (2006.01) |
| C12N 15/09 | (2006.01) |
| A61K 35/761 | (2015.01) |

(52) U.S. Cl.
CPC .......... *A61K 31/713* (2013.01); *A61K 35/761* (2013.01); *A61K 45/06* (2013.01); *A61K 48/005* (2013.01); *A61K 48/0008* (2013.01); *A61P 35/00* (2018.01); *C12N 15/09* (2013.01); *C12N 15/63* (2013.01); *C12N 15/86* (2013.01); *A61K 2300/00* (2013.01); *C12N 2710/10343* (2013.01); *C12N 2750/14143* (2013.01); *C12N 2830/002* (2013.01); *C12N 2830/15* (2013.01); *C12N 2840/206* (2013.01)

(58) Field of Classification Search
None
See application file for complete search history.

(56) References Cited

U.S. PATENT DOCUMENTS

| 7,811,814 | B2 * | 10/2010 | Bohn | C12N 15/86 |
| | | | | 435/320.1 |
| 9,555,127 | B2 * | 1/2017 | Cueva-Mendez | |
| | | | | A61K 47/6901 |
| 2019/0153409 | A1 | 5/2019 | Arber et al. | |

FOREIGN PATENT DOCUMENTS

| WO | WO 00/56909 | 9/2000 |
| WO | WO 2013/027217 | 2/2013 |
| WO | WO 2013/037504 | 3/2013 |
| WO | WO 2016/185471 | 11/2016 |

OTHER PUBLICATIONS

Tian et al. A doxorubicin delivery platform using engineered natural membrane vesicle exosomes for targeted tumor therapy. Biomaterials. Feb. 2014;35(7):2383-90.*
Supplementary European Search Report and the European Search Opinion dated Sep. 12, 2019 From the European Patent Office Re. Application No. 16796018.6.-1111(4 Pages).*
Multiplicity of infection—Wikipedia downloaded Feb. 6, 2020 ; p. 1-3.*
Naumov et al. Novel approach to abuse the hyperactive K-Ras pathway for adenoviral gene therapy of colorectal cancer Experimental Cell Research 318(2012) 160-168.*
Boustanai et al., Bacterial Toxins Selectively Kills K-Ras Mutated Cancer Cells American Journal of Gastroenterology: Oct. 2017—vol. 112—Issue—p. S105-S107.*
Boustanai et al. Designing of a Novel Strategy for Cancer Gene Therapy by Selective Delivery of Adenovirus-Based Toxin 851 Gastroenterology 2016 Abstract pp. 1-2.*
Choi et al Production of Recombinant Adeno-Associated Viral Vectors First published: Apr. 1, 2007 ; Current Protocols in Human Genetics (2007) 12.9.1-12.9.21.*
Bahassi E M, et al., 1999. "Interactions of CcdB with DNA gyrase. Inactivation of Gyra, poisoning of the gyrase-DNA complex, and the antidote action of CcdA". J Biol Chem, 274 (16): 10936-44.*

(Continued)

*Primary Examiner* — Maria G Leavitt
(74) *Attorney, Agent, or Firm* — The Roy Gross Law Firm, LLC; Roy Gross

(57) ABSTRACT

Provided are nucleic acid constructs and systems which comprise (i) a first nucleic acid construct encoding a toxin operatively linked to a first promoter and at least one cancer-associated signaling responsive enhancer element; and (ii) a second nucleic acid construct encoding an antitoxin operatively linked to a second promoter, the second promoter being stronger than the first promoter.
Also provided are pharmaceutical compositions comprising same and methods of using same for treating cancer.

Figure 11:
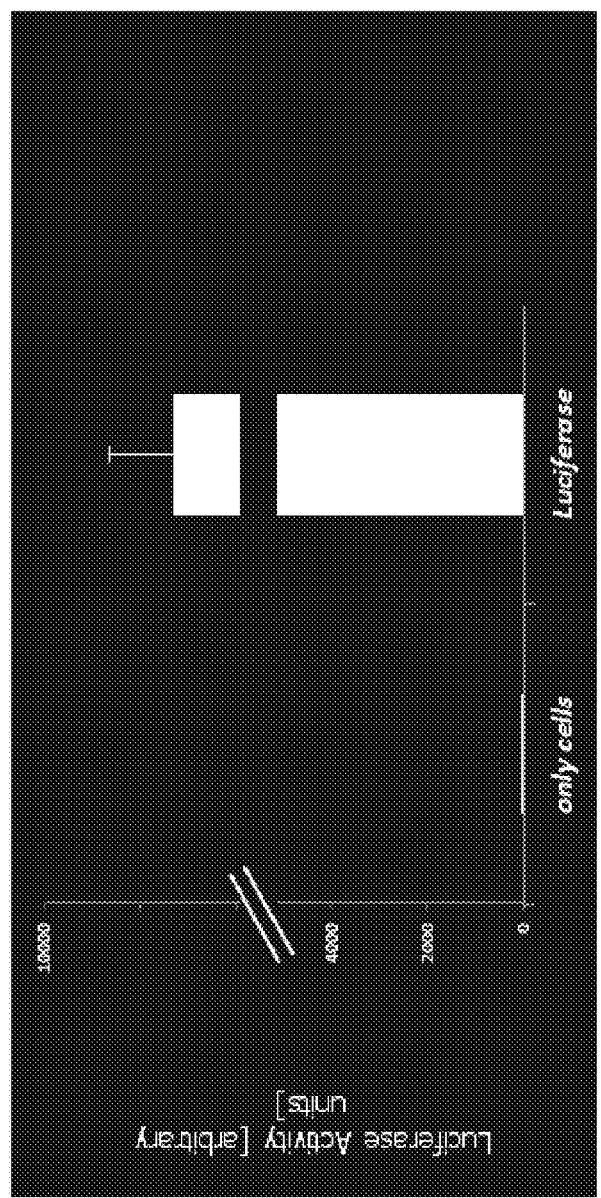

18 Claims, 22 Drawing Sheets
(17 of 22 Drawing Sheet(s) Filed in Color)
Specification includes a Sequence Listing.

(56) References Cited

OTHER PUBLICATIONS

Supplementary European Search Report and the European Search Opinion dated Dec. 6, 2018 From the European Patent Office Re. Application No. 16796018.6. (7 Pages).

International Preliminary Report on Patentability dated Nov. 30, 2017 From the International Bureau of WIPO Re. Application No. PCT/IL2016/050522. (11 Pages).

International Search Report and the Written Opinion dated Aug. 1, 2016 From the International Searching Authority Re. Application No. PCT/IL2016/050522.

Dvory-Sobol et al. "Gene Targeting Approach to Selectively Kill Colon Cancer Cells, With Hyperactive K-Ras Pathway", Biomedicine & Pharmacotherapy, 59(Suppl.2): S370-S374, Oct. 31, 2005.

Dvory-Sobol et al. "Suppression of Gastric Cancer Cell Growth by Targeting the Beta-Catenin/T-Cell Factor Pathway", Cancer, 109(2): 188-197, Published Online Dec. 5, 2006.

Dvory-Sobol et al. "Targeting the Active Beta-Catenin Pathway to Treat Cancer Cells", Molecular Cancer Therapy, 5(11): 2861-2871, Nov. 2006.

El-Aneed "Current Strategies in Cancer Gene Therapy", European Journal of Pharmacology. 498(1): 1-8, Available Online Jul. 30, 2004.

Engelberg-Kulka et al. "Bacterial Programmed Cell Death and Multicellular Behavior in Bacteria", PLoS Genetics, 2(10): e135-1-e135-9, Oct. 2006.

Engelberg-Kulka et al. "MazEF: A Chromosomal Toxin-Antitoxin Module That Triggers Programmed Cell Death in Bacteria", Journal of Cell Science, 118(19): 4327-4332, Published Online Oct. 1, 2005.

FitzGerald et al. "Redirecting Pseudomonas Exotoxin", Seminars in Cell Biology, 2(1): 31-37, Feb. 1991. Abstract.

Gerdes et al. "Mechanism of Postsegregational Killing by the Hok Gene Product of the ParB System of Plasmid RI and Its Homolog With the RelF Gene Product of the *E. Coli* RelB Operon", The EMBO Journal, 5(8): 2023-2029, Aug. 1986.

Giladi et al. "Gene Therapy Approach in Prostate Cancer Cells Using An Active Wnt Signal". Biomedicine & Pharmacotherapy, 61(9): 527-530, Available Online Sep. 14, 2007.

Inouye "The Discovery of mRNA Interferases: Implication in Bacterial Physiology and Application to Biotechnology", Journal of Cellular Physiology, 209(3): 670-676, Dec. 1, 2006.

Lisiansky et al. "Gene Therapy of Pancreatic Cancer Targeting the K-Ras Oncogene", Cancer Gene Therapy, 19(12): 862-869, Published Online Oct. 26, 2012.

Naumov et al. "Novel Approach to Abuse the Hyperactive K-Ras Pathway for Adenoviral Gene Therapy of Colorectal Cancer", Experimental Cell Reseach, 318(2): 160-168, Available Online Oct. 12, 2011. Fig.1.

Shapira et al. "Selective Eradication of Cancer Cells by Adenovirus-Based Delivery of Cytotoxic Agents: An Alternative Method for Targeting Pancreatic Cancer", Proceedings of the 104th Annual Meeting of the American Association for Cancer Research, AACR, Washington, DC, USA, Apr. 6-10, 2013, 73(8 Suppl.): # 3303, Apr. 15, 2013. Fig.2.

Shapira et al. "The 'Trojan Horse' Strategy: Selective Eradication of Cancer Cells by Adenovirus-Based Delivery of Cytotoxic Agents: An Alternative Method for Targeting Pancreatic (PC) and Colorectal Cancer (CRC)", Gastroenterology, 146(5): S-152, # 873, May 2, 2014. Fig.2.

Thisted et al. "Mechanism of Post-Segregational Killing: Sok Antisense RNA Interacts With Hok mRNA Via Its 5'-End Single-Stranded Leader and Competes With the 3'-End of Hok mRNA for Binding to the Mok Translational Initiation Region", The EMBO Journal, 13(8): 1960-1968, Apr. 15, 1994.

Yu et al. "Targeting Strategies for Multifunctional Nanoparticles in Cancer Imaging and Therapy", Theranostics, 2(1): 3-44, Jan. 1, 2012.

Communication Pursuant to Article 94(3) EPC dated Sep. 12, 2019 From the European Patent Office Re. Application No. 16796018.6. (4 Pages).

\* cited by examiner

FIG. 1A
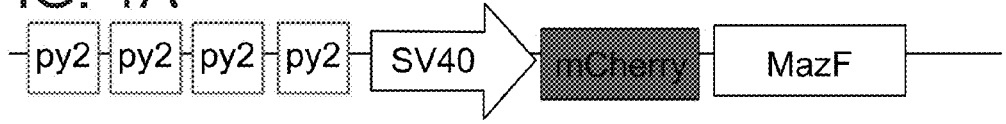
FIG. 1B 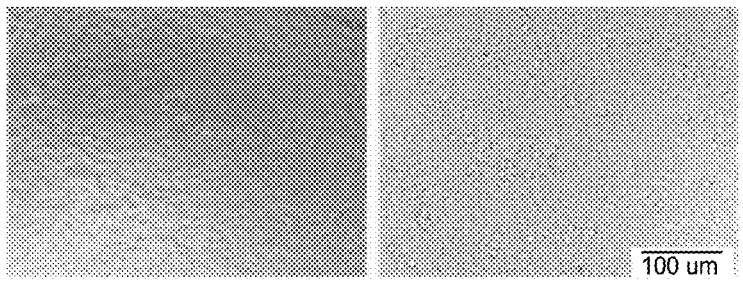 FIG. 1C
FIG. 1D 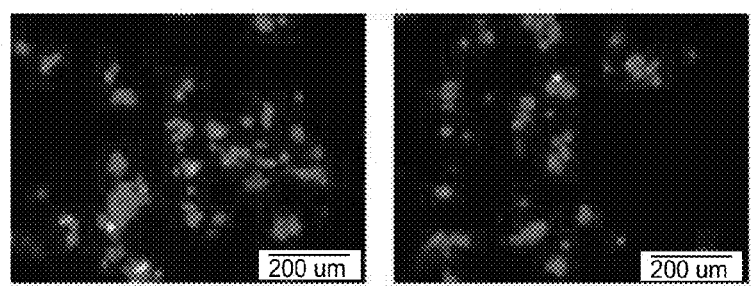 FIG. 1E
FIG. 1F
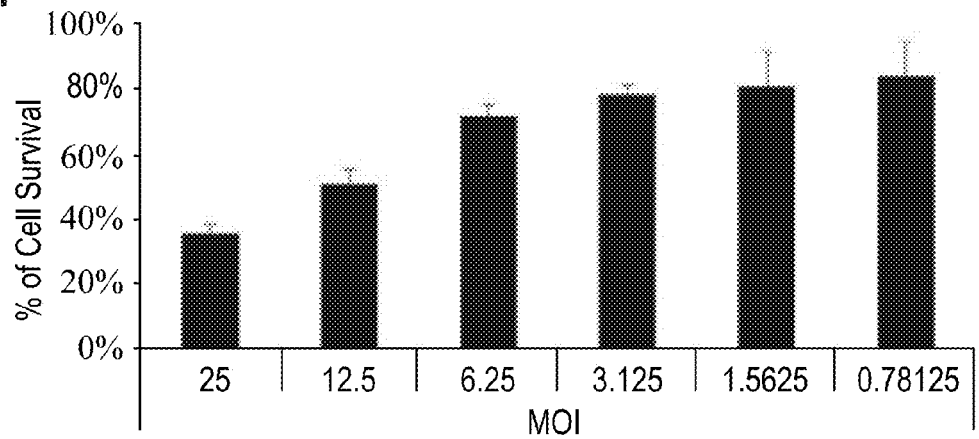
FIG. 1G 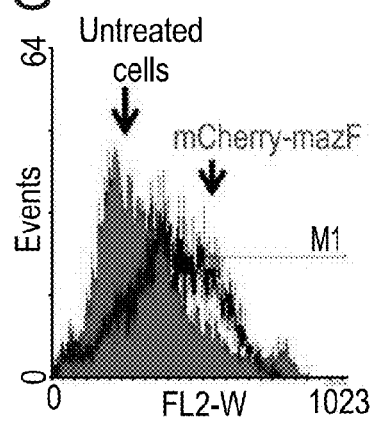 FIG. 1H 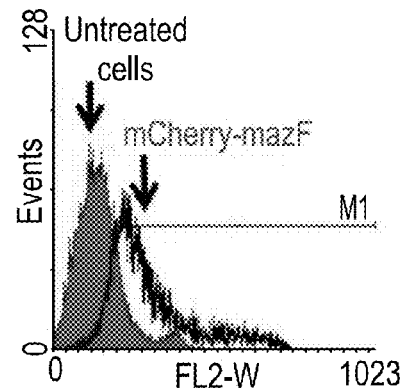

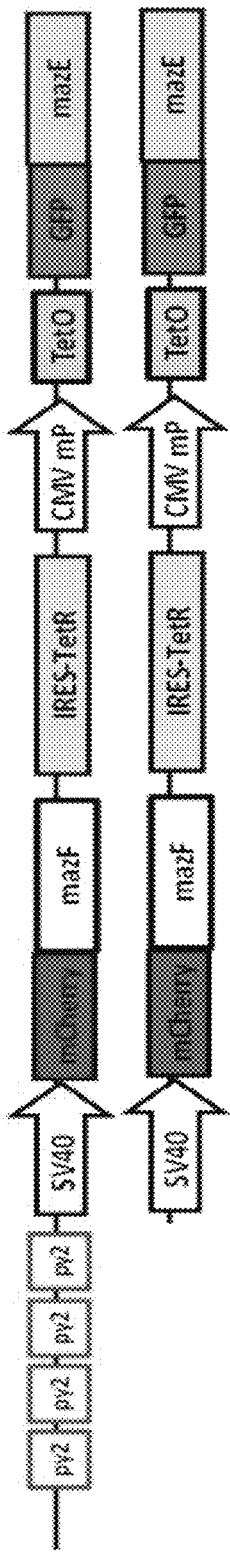

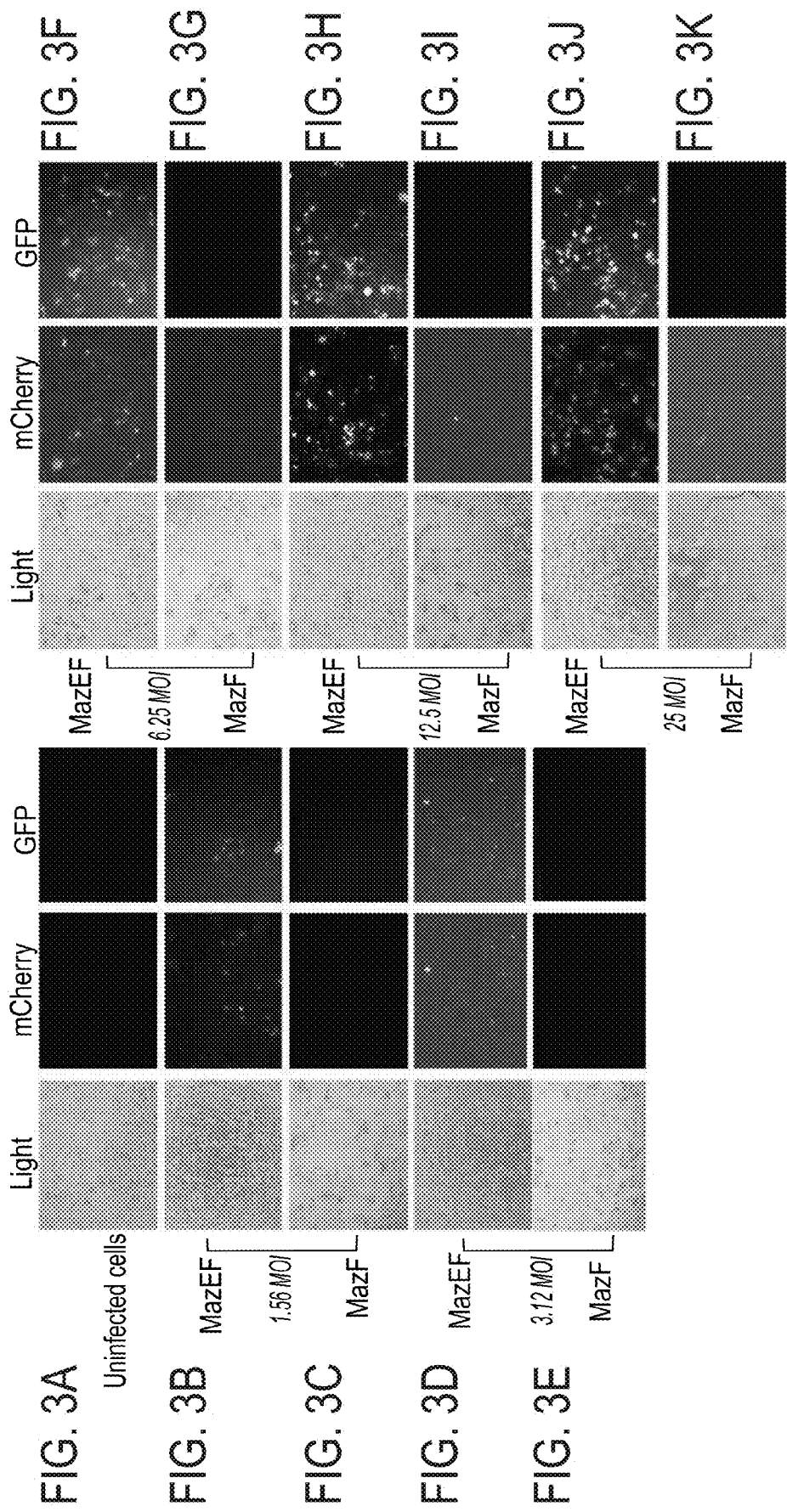

Figure 10:
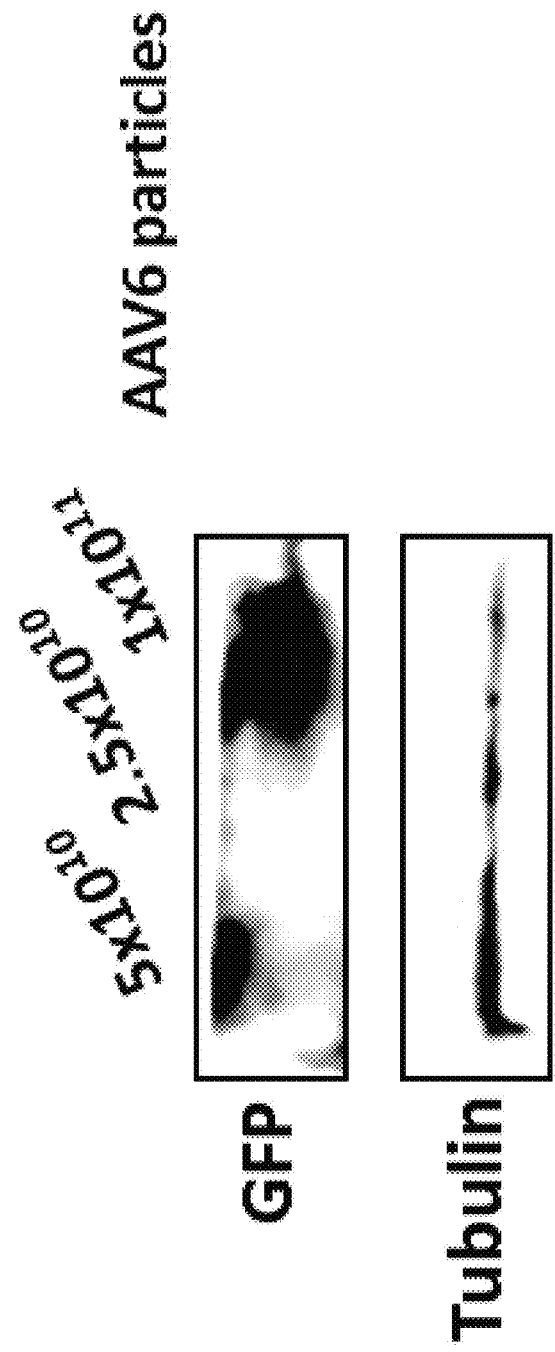

FIG. 4A
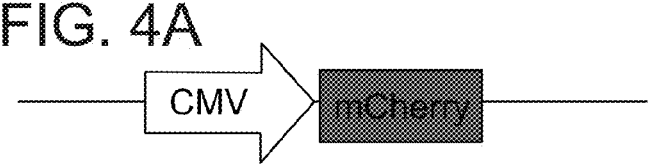
FIG. 4B  
Control
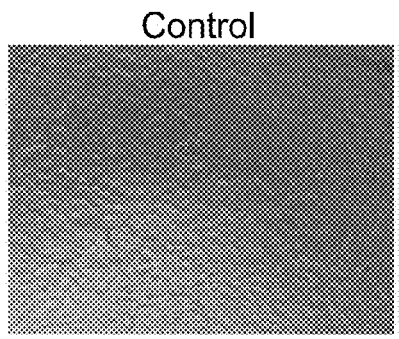
FIG. 4C  
5 MOI
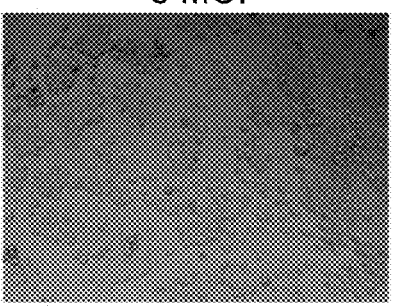
FIG. 4D  
10 MOI
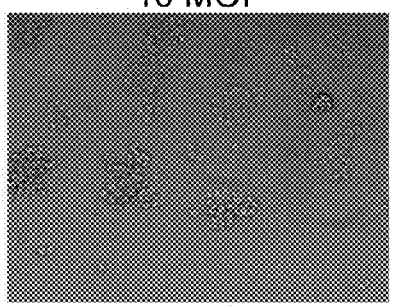
FIG. 4E
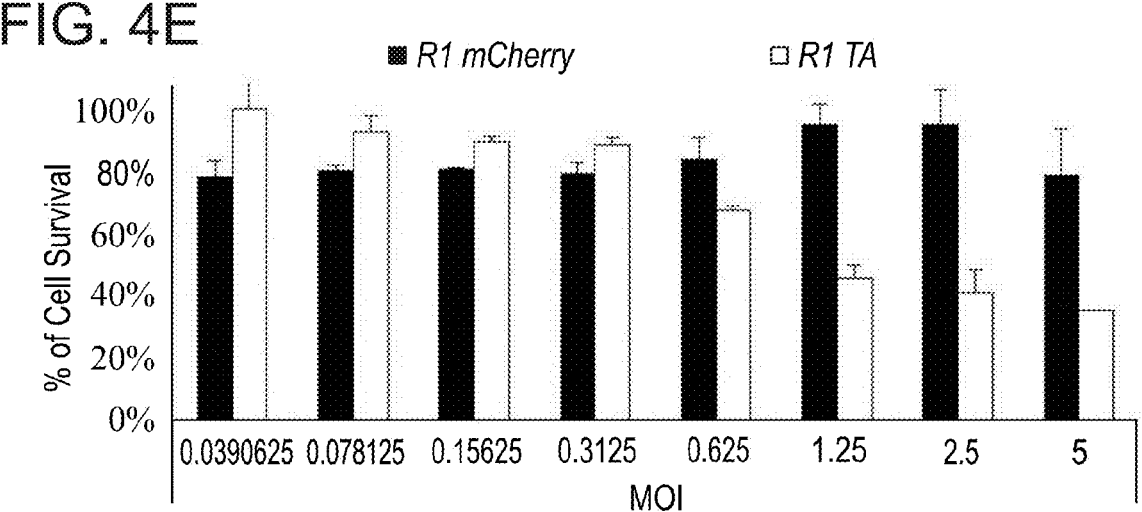
5 MOI
mCherry
FIG. 4F
GFP
FIG. 4G
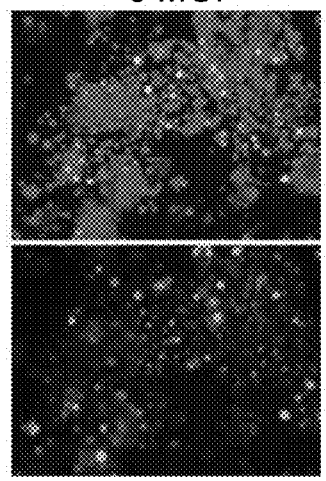

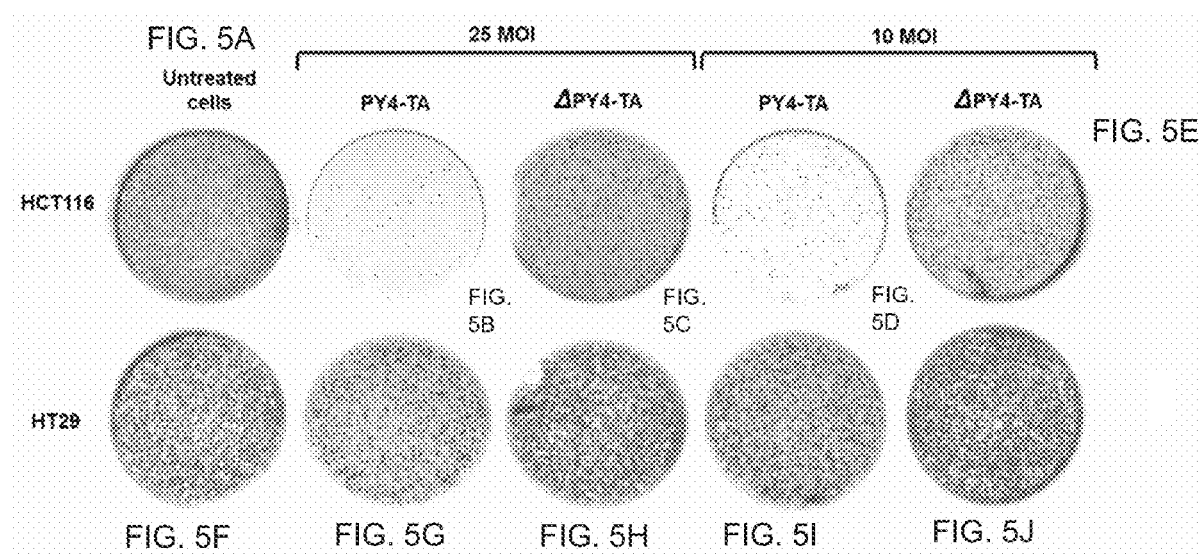

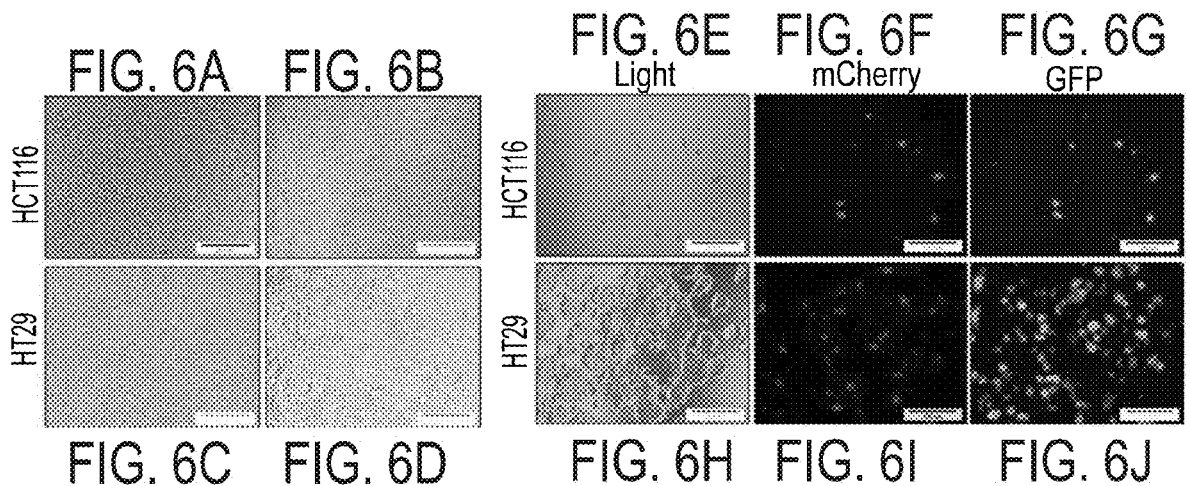
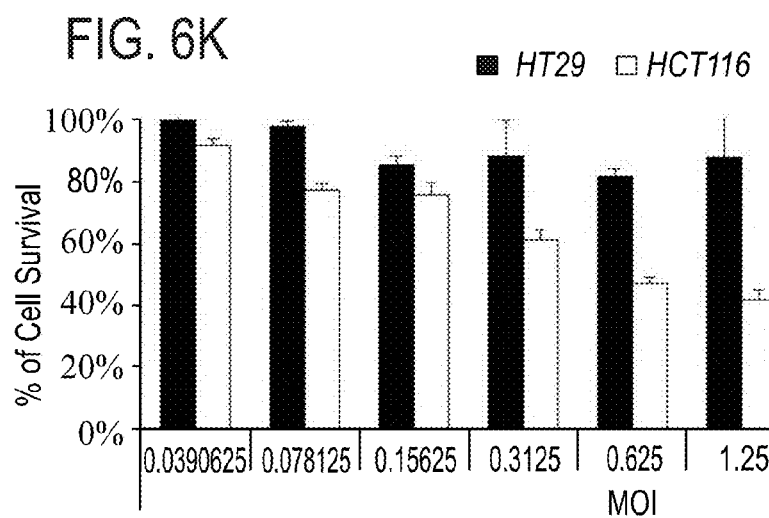
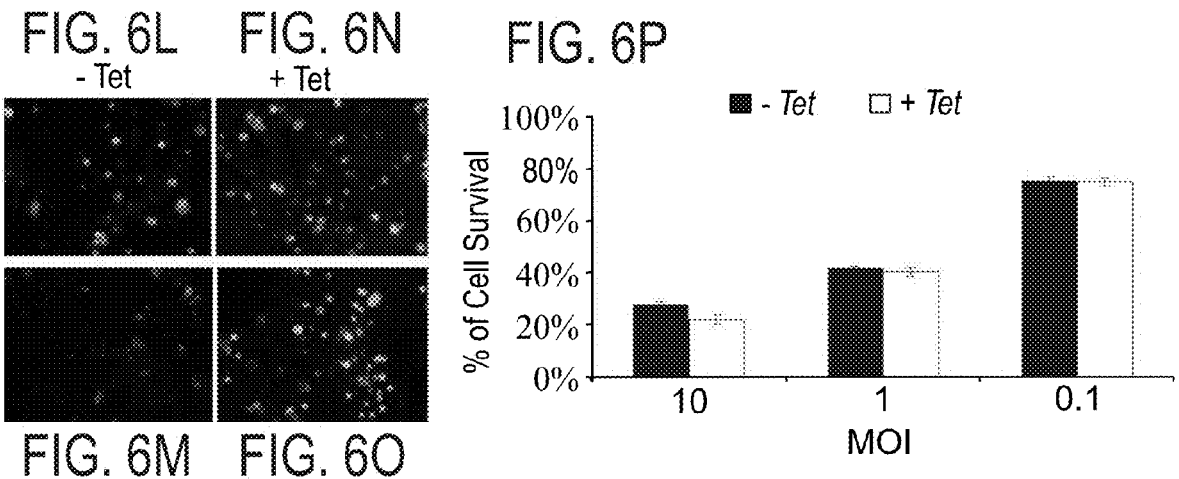

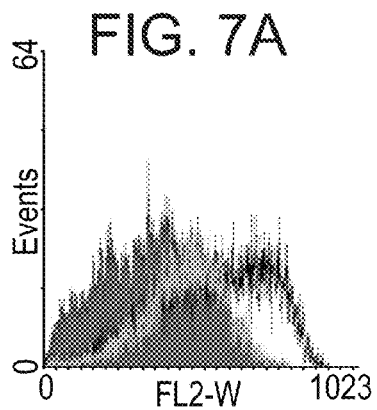
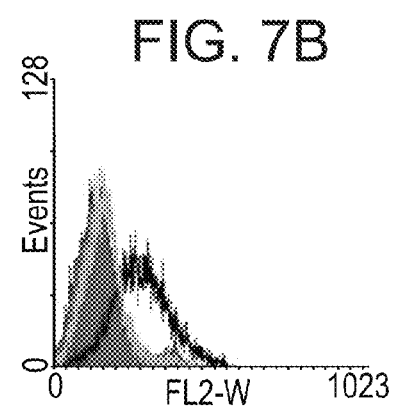
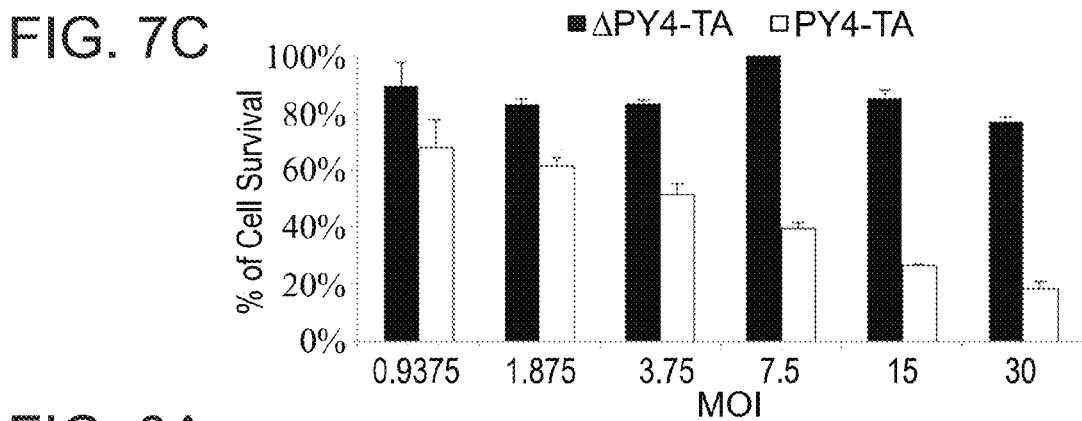
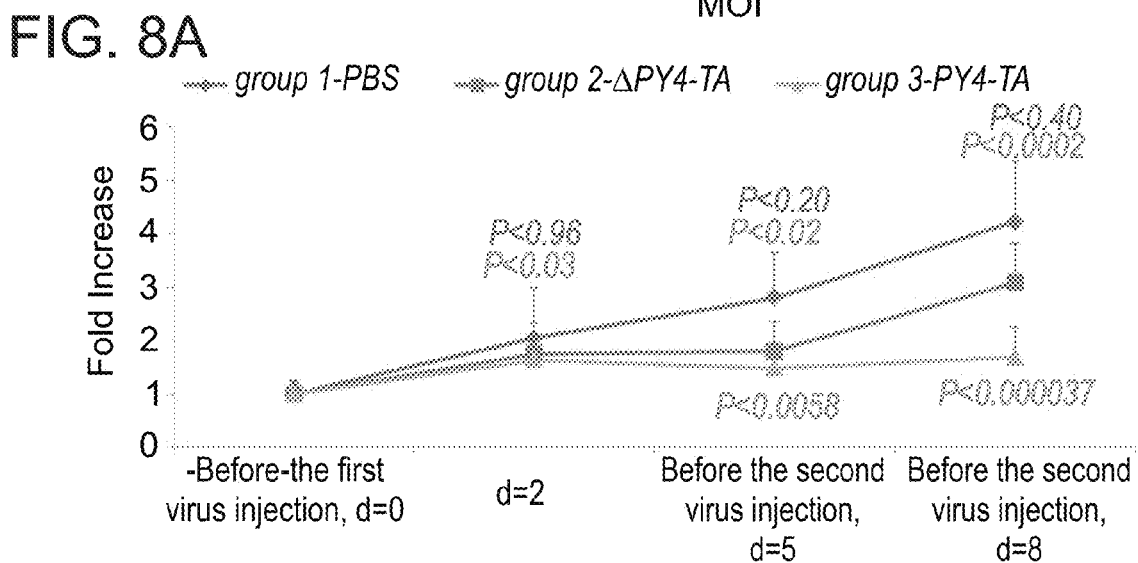
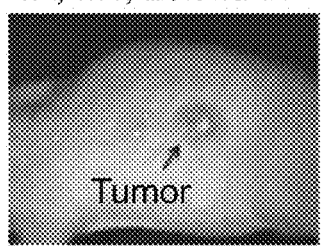
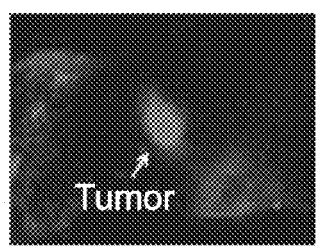

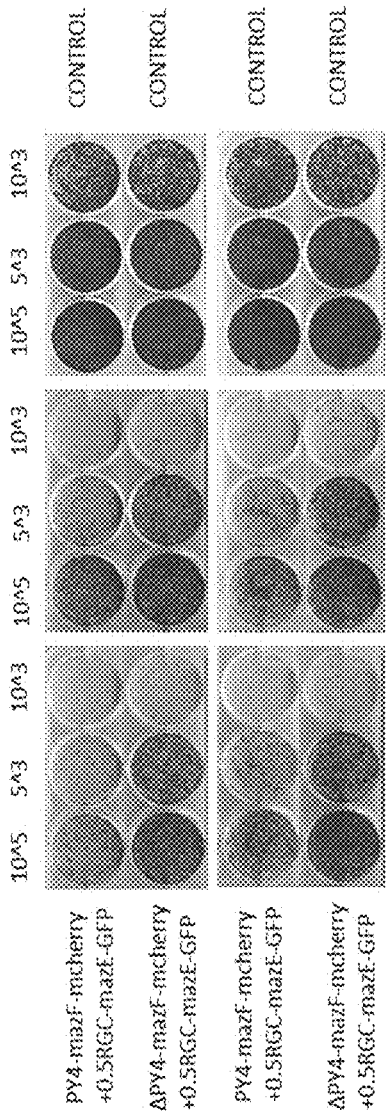
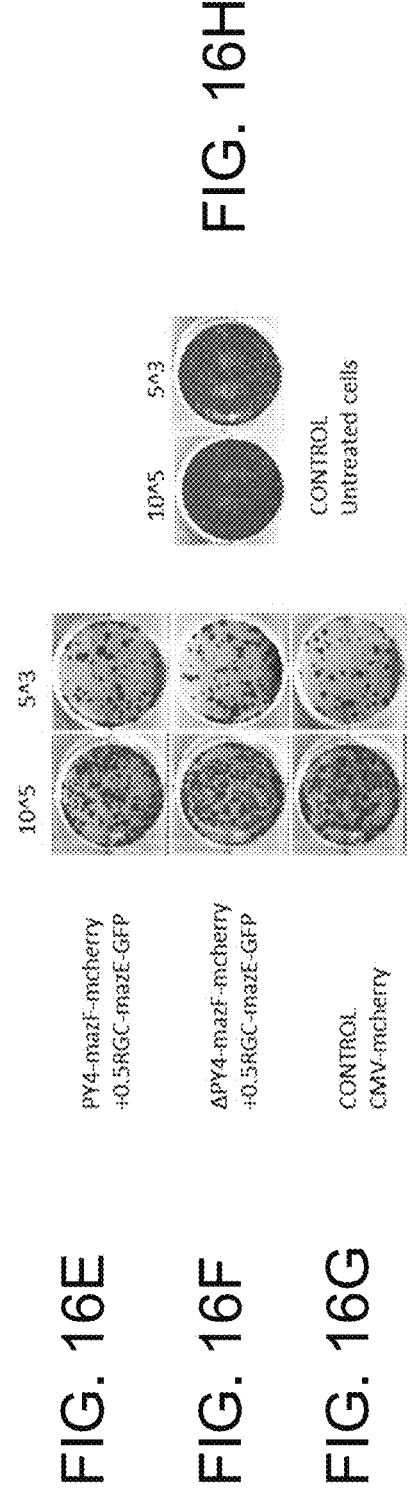

SEQUENCE LISTING

<160> NUMBER OF SEQ ID NOS: 53

<210> SEQ ID NO 1
<211> LENGTH: 7
<212> TYPE: DNA
<213> ORGANISM: Artificial sequence
<220> FEATURE:
<223> OTHER INFORMATION: Ets binding site

<400> SEQUENCE: 1 caggaag                                                              7

<210> SEQ ID NO 2
<211> LENGTH: 8
<212> TYPE: DNA
<213> ORGANISM: Artificial sequence
<220> FEATURE:
<223> OTHER INFORMATION: AP-1 binding site

<400> SEQUENCE: 2 tgactaag                                                             8

<210> SEQ ID NO 3
<211> LENGTH: 15
<212> TYPE: DNA
<213> ORGANISM: Artificial sequence
<220> FEATURE:
<223> OTHER INFORMATION: PY2 sequence

<400> SEQUENCE: 3
caggaagtga ctaag                                                    15

<210> SEQ ID NO 4
<211> LENGTH: 203
<212> TYPE: DNA
<213> ORGANISM: Artificial sequence
<220> FEATURE:
<223> OTHER INFORMATION: SV40 minimal promoter

<400> SEQUENCE: 4
gcgatctgca tctcaattag tcagcaacca tagtcccgcc cctaactccg cccatcccgc     60
ccctaactcc gcccagttcc gcccattctc cgccccatcg ctgactaatt ttttttattt    120
atgcagaggc cgaggccgcc tcggcctctg agctattcca gaagtagtga ggaggctttt    180
ttggaggcct aggcttttgc aaa                                           203

<210> SEQ ID NO 5
<211> LENGTH: 717
<212> TYPE: DNA
<213> ORGANISM: Artificial sequence
<220> FEATURE:
<223> OTHER INFORMATION: mCherry coding sequence

<400> SEQUENCE: 5
atgggaattc acgtgagcaa gggcgaggag dataacatgg ccatcatcaa ggagttcatg     60
cgcttcaagg tgcacatgga gggctccgtg aacggccacg agttcgagat cgagggcgag    120
ggcgagggcc gcccctacga gggcacccag accgccaagc tgaaggtgac caagggtggc    180
cccctgccct cgcctgggca catcctgtcc cctcagttca tgtacggctc caaggcctac    240
gtgaagcacc ccgccgacat ccccgactac ttgaagctgt ccttccccga gggcttcaag    300
tgggagcgcg tgatgaactt cgaggacggc ggcgtggtga ccgtgaccca ggactcctcc    360
ctgcaggacg gcgagttcat ctacaaggtg aagctgcgcg gcaccaactt cccctccgac    420

```
ggccccgtaa tgcagaagaa gaccatgggc tgggaggcct cctccgagcg gatgtacccc    480
gaggacggcg ccctgaaggg cgagatcaag cagaggctga agctgaagga cggcggccac    540
tacgacgctg aggtcaagac cacctacaag gccaagaagc ccgtgcagct gcccggcgcc    600
tacaacgtca acatcaagtt ggacatcacc tcccacaacg aggactacac catcgtggaa    660
cagtacgaac gcgccgaggg ccgccactcc accggcggca tggacgagct gtacaag       717

<210> SEQ ID NO 6
<211> LENGTH: 342
<212> TYPE: DNA
<213> ORGANISM: Artificial sequence
<220> FEATURE:
<223> OTHER INFORMATION: E. coli MazF ribonuclease

<400> SEQUENCE: 6
atggtaagcc gatacgtacc cgatatgggc gatctgattt gggttgattt tgacccgaca     60
aaaggtagcg agcaagctgg acatcgtcca gctgttgtcc tgagtccttt catgtacaac    120
aacaaaacag gtatgtgtct gtgtgttcct tgtacaacgc aatcaaaagg atatccgttc    180
gaagttgttt tatccggtca ggaacgtgat ggcgtagcgt tagctgatca ggtaaaaagt    240
atcgcctggc gggcaagagg agcaacgaag aaaggaacag ttgccccaga ggaattacaa    300
ctcattaaag ccaaaattaa cgtactgatt ggcaccggtt ag                       342

<210> SEQ ID NO 7
<211> LENGTH: 588
<212> TYPE: DNA
<213> ORGANISM: Artificial sequence
<220> FEATURE:
<223> OTHER INFORMATION: IRES

<400> SEQUENCE: 7
gcccctctcc ctcccccccc cctaacgtta ctggccgaag ccgcttggaa taaggccggt     60
gtgcgtttgt ctatatgtta ttttccacca tattgccgtc ttttggcaat gtgagggccc    120
ggaaacctgg ccctgtcttc ttgacgagca ttcctagggg tctttcccct ctcgccaaag    180
gaatgcaagg tctgttgaat gtcgtgaagg aagcagttcc tctggaagct tcttgaagac    240
aaacaacgtc tgtagcgacc ctttgcaggc agcggaaccc cccacctggc gacaggtgcc    300
tctgcggcca aaagccacgt gtataagata cacctgcaaa ggcggcacaa ccccagtgcc    360
acgttgtgag ttggatagtt gtggaaagag tcaaatggct ctcctcaagc gtattcaaca    420
aggggctgaa ggatgcccag aaggtacccc attgtatggg atctgatctg ggcctcggt    480 gcacatgctt tacatgtgtt tagtcgaggt taaaaaaacg tctaggcccc cgaaccacg     540 gggacgtggt tttcctttga aaacacgat gataatatgg ccacaacc                  588

<210> SEQ ID NO 8
<211> LENGTH: 657
<212> TYPE: DNA
<213> ORGANISM: Artificial sequence
<220> FEATURE:
<223> OTHER INFORMATION: Tetracycline repressor

<400> SEQUENCE: 8
atgagcagat tagataaaag taaagtgatt aacagcgcat tagagctgct taatgaggtc     60
ggaatcgaag gtttaacaac ccgtaaactc gcccagaagc taggtgtaga gcagcctaca    120
ttgtattggc atgtaaaaaa taagcgggct ttgctcgacg ccttagccat tgagatgtta    180
```

```
gataggcacc atactcactt tgcccttta aaggggaaa gctggcaaga tttttttacgt    240 aataacgcta aaagttttag atgtgcttta ctaagtcatc gcgatggagc aaaagtacat   300
ttaggtacac ggcctacaga aaaacagtat gaaactctcg aaaatcaatt agcctttta    360 tgccaacaag ttttttcact agagaatgca ttatatgcac tcagcgctgt ggggcatttt   420
actttaggtt gcgtattgga agatcaagag catcaagtcg ctaaagaaga aagggaaaca   480
cctactactg atagtatgcc gccattatta cgacaagcta tcgaattatt tgatcaccaa   540
ggtgcagagc cagccttctt attcggcctt gaattgatca tatgcggatt agaaaaacaa   600
cttaaatgtg aaagtgggtc cgcgtacagc ggatcccggg aattcagatc ttattaa     657
```

<210> SEQ ID NO 9
<211> LENGTH: 241
<212> TYPE: DNA
<213> ORGANISM: Artificial sequence
<220> FEATURE:
<223> OTHER INFORMATION: CMV minimal promoter+2xtetracycline operator

<400> SEQUENCE: 9

```
accaaaatca acgggacttt ccaaaatgtc gtaacaactc cgccccattg acgcaaatgg    60
gcggtaggcg tgtacggtgg gaggtctata taagcagagc tctccctatc agtgatagag   120
atctccctat cagtgatagag atcgtcgac gagctcgttt agtgaaccgt cagatcgcct   180
ggagacgcca tccacgctgt tttgacctcc atagaagaca ccgggaccga tccagcctcc   240
g                                                                    241
```

<210> SEQ ID NO 10
<211> LENGTH: 42
<212> TYPE: DNA
<213> ORGANISM: Artificial sequence
<220> FEATURE:
<223> OTHER INFORMATION: 2xtetracycline operator

<400> SEQUENCE: 10

```
tccctatcag tgatagagat ctccctatca gtgatagaga tc                       42
```

<210> SEQ ID NO 11
<211> LENGTH: 21
<212> TYPE: DNA
<213> ORGANISM: Artificial sequence
<220> FEATURE:
<223> OTHER INFORMATION: tetracycline operator

<400> SEQUENCE: 11

```
tccctatcag tgatagagat c                                              21
```

<210> SEQ ID NO 12
<211> LENGTH: 717
<212> TYPE: DNA
<213> ORGANISM: Artificial sequence
<220> FEATURE:
<223> OTHER INFORMATION: GFP coding sequence

<400> SEQUENCE: 12

```
atggtgagca agggcgagga gctgttcacc ggggtggtgc ccatcctggt cgagctggac     60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
```

```
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaag      717

<210> SEQ ID NO 13
<211> LENGTH: 249
<212> TYPE: DNA
<213> ORGANISM: Artificial sequence
<220> FEATURE:
<223> OTHER INFORMATION: E. coli antitoxin MazE

<400> SEQUENCE: 13
atgatccaca gtagcgtaaa gcgttgggga aattcaccgg cggtgcggat cccggctacg     60
ttaatgcagg cgctcaatct gaatattgat gatgaagtga agattgacct ggtggatggc    120
aaattaatta ttgagccagt gcgtaaagag cccgtattta cgcttgctga actggtcaac    180
gacatcacgc cggaaaacct ccacgagaat atcgactggg gagagccgaa agataaggaa    240
gtctggtaa                                                            249

<210> SEQ ID NO 14
<211> LENGTH: 19
<212> TYPE: DNA
<213> ORGANISM: Artificial sequence
<220> FEATURE:
<223> OTHER INFORMATION: p53 wild type responsive element

<400> SEQUENCE: 14
cctgcctgga cttgcctgg                                                  19

<210> SEQ ID NO 15
<211> LENGTH: 325
<212> TYPE: DNA
<213> ORGANISM: Artificial sequence
<220> FEATURE:
<223> OTHER INFORMATION: RGCx17 (17 repeats of the p53 WT responsive
      element)

<400> SEQUENCE: 15
cctgcctgga cttgcctggc ctgcctggac ttgcctggcc tgcctggact tgcctggcct     60
gcctggactt gcctggcctg cctggacttg cctggcctgc ctggacttgc ctggcctgcc    120
tggacttgcc tggcctgcct ggacttgcct ggcctgcctg gacttgcctg gccctgcct    180 ggacttgcct ggcctgcctg gacttgcctg gcctgcctgg acttgcctgg cctgcctgga    240
cttgcctggc ctgcctggac ttgcctggcc tgcctggact tgcctggcct gcctggactt    300
gcctggcctg cctggacttg cctgg                                          325

<210> SEQ ID NO 16
<211> LENGTH: 188
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa can be glycine or aspartic acid
```

<400> SEQUENCE: 16

```
Met Thr Glu Tyr Lys Leu Val Val Gly Ala Gly Xaa Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 17
<211> LENGTH: 189
<212> TYPE: PRT
<213> ORGANISM: homo sapiens
<220> FEATURE:
<221> NAME/KEY: MISC_FEATURE
<222> LOCATION: (61)..(61)
<223> OTHER INFORMATION: Xaa can be Glutamine or lysine

<400> SEQUENCE: 17

```
Met Thr Glu Tyr Lys Leu Val Val Gly Ala Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Xaa Glu Glu Tyr
    50                  55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
```

```
145                 150                 155                 160
Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 18
<211> LENGTH: 189
<212> TYPE: PRT
<213> ORGANISM: homo sapiens
<220> FEATURE:
<221> NAME/KEY: MISC_FEATURE
<222> LOCATION: (12)..(12)
<223> OTHER INFORMATION: Xaa can be glycine or valine

<400> SEQUENCE: 18

Met Thr Glu Tyr Lys Leu Val Val Val Gly Ala Xaa Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 19
<211> LENGTH: 527
<212> TYPE: DNA
<213> ORGANISM: Artificial sequence
<220> FEATURE:
<223> OTHER INFORMATION: CMV minimal promoter (without the tetracycline
      operator)

<400> SEQUENCE: 19
cgttacataa cttacggtaa atggcccgcc tggctgaccg cccaacgacc cccgcccatt      60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta cggactttcc tacttggca gtacatctac gtattagtca tcgctattac     300
catggtgatg cggttttggc agtacaccaa tgggcgtgga tagcggtttg actcacgggg    360
```

```
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagctcg tttagtgaac cgtcaga                  527
```

```
<210> SEQ ID NO 20
<211> LENGTH: 1653
<212> TYPE: DNA
<213> ORGANISM: Artificial sequence
<220> FEATURE:
<223> OTHER INFORMATION: luciferase coding sequence

<400> SEQUENCE: 20
```

```
atggaagacg ccaaaaacat aaagaaaggc ccggcgccat tctatccgct ggaagatgga     60
accgctggag agcaactgca taaggctatg aagagatacg ccctggttcc tggaacaatt    120
gcttttacag atgcacatat cgaggtggac atcacttacg ctgagtactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgggcatt    360
tcgcagccta ccgtggtgtt cgtttccaaa aggggttgc aaaaaatttt gaacgtgcaa    420
aaaaagctcc caatcatcca aaaaattatt atcatggatt ctaaaacgga ttaccaggga    480
tttcagtcga tgtacacgtt cgtcacatct catctacctc ccggttttaa tgaatacgat    540
tttgtgccag agtccttcga tagggacaag acaattgcac tgatcatgaa ctcctctgga    600
tctactggtc tgcctaaagg tgtcgctctg cctcatagaa ctgcctgcgt gagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttc tgaggagcct tcaggattac    840
aagattcaaa gtgcgctgct ggtgccaacc ctattctcct tcttcgccaa agcactctg    900 attgacaaat acgatttatc taatttacac gaaattgctt ctggtggcgc tccctctct    960 aaggaagtcg gggaagcggt tgccaagagg ttccatctgc caggtatcag gcaaggatat   1020
gggctcactg agactacatc agctattctg attacacccg agggggatga taaaccgggc   1080
gcggtcggta aagttgttcc attttttgaa gcgaaggttg tggatctgga taccgggaaa   1140
acgctgggcg ttaatcaaag aggcgaactg tgtgtgagag gtcctatgat tatgtccggt   1200
tatgtaaaca atccggaagc gaccaacgcc ttgattgaca aggatggatg gctacattct   1260
ggagacatag cttactggga cgaagacgaa cacttcttca tcgttgaccg cctgaagtct   1320
ctgattaagt acaaaggcta tcaggtggct cccgctgaat tggaatccat cttgctccaa   1380
caccccaaca tcttcgacgc aggtgtcgca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gatcgccgtg taa                                1653
```

```
<210> SEQ ID NO 21
<211> LENGTH: 52
<212> TYPE: DNA
<213> ORGANISM: Artificial sequence
<220> FEATURE:
<223> OTHER INFORMATION: Hind-Cher-Forward primer
```

<400> SEQUENCE: 21
cttttgcaaa aagcttccac catgggaatt cacgtgagca agggcgagga gg        52

<210> SEQ ID NO 22
<211> LENGTH: 49
<212> TYPE: DNA
<213> ORGANISM: Artificial sequence
<220> FEATURE:
<223> OTHER INFORMATION: Xba-Maz-Reverse primer

<400> SEQUENCE: 22
ccgccccgac tctagactaa ccggtgccaa tcagtacgtt aattttggc            49

<210> SEQ ID NO 23
<211> LENGTH: 4
<212> TYPE: DNA
<213> ORGANISM: Artificial sequence
<220> FEATURE:
<223> OTHER INFORMATION: ETS domain

<400> SEQUENCE: 23 ggaw                                                              4

<210> SEQ ID NO 24
<211> LENGTH: 36
<212> TYPE: DNA
<213> ORGANISM: Artificial sequence
<220> FEATURE:
<223> OTHER INFORMATION: ToxI RNA repeated motif

<400> SEQUENCE: 24
aggtgatttg ctacctttaa gtgcagctag aaattc                          36

<210> SEQ ID NO 25
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 25
cccaagcaat ggatgatttg a                                          21

<210> SEQ ID NO 26
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 26
ggcagaccag catgacagat t                                          21

<210> SEQ ID NO 27
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 27
tgagcagatc atgaagacag gg                                         22

<210> SEQ ID NO 28

```
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 28
agagctggaa gtcgagtgt                                                   19

<210> SEQ ID NO 29
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 29
tcaacgcaca gtacgagcg                                                   19

<210> SEQ ID NO 30
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 30
caggcaaatg tgcaatacca a                                                21

<210> SEQ ID NO 31
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 31
gcctataaga acgtggtggg c                                                21

<210> SEQ ID NO 32
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 32
ccctcctacc tctggttctt acg                                              23

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
ccaggaggca ctcacagagc                                                  20

<210> SEQ ID NO 34
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 34
```
ctcaacgtcg accccgataa                                                    20

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
ccaccgcatc tctacattca                                                    20

<210> SEQ ID NO 36
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 36
ggcattctgg gagcttcatc t                                                  21

<210> SEQ ID NO 37
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 37
gcggattagg gcttcctctt                                                    20

<210> SEQ ID NO 38
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 38
gctcgatcct ggatgaaacc                                                    20

<210> SEQ ID NO 39
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 39
gcaccttcac attcctctc                                                     19

<210> SEQ ID NO 40
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 40
gtaagggcag gagtcccatg                                                    20

<210> SEQ ID NO 41
<211> LENGTH: 26
<212> TYPE: DNA

```
<213> ORGANISM: Artificial sequence
<220> FEATURE:
<223> OTHER INFORMATION: Single strand DNA oligonucleotide

<400> SEQUENCE: 41
ggttacagca ccatcagtag gtacag                                          26

<210> SEQ ID NO 42
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 42
cctcgttgct tttctgctca a                                               21

<210> SEQ ID NO 43
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 43
ttgaatgtca gtcacttggg cat                                             23

<210> SEQ ID NO 44
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 44
gcccttggac ggcttttc                                                   18

<210> SEQ ID NO 45
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 45
acatctctgt cgtcgtcctc g                                               21

<210> SEQ ID NO 46
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 46
caagtctggc tcgttctcag t                                               21

<210> SEQ ID NO 47
<211> LENGTH: 52
<212> TYPE: PRT
<213> ORGANISM: Escherichia coli

<400> SEQUENCE: 47

Met Lys Leu Pro Arg Ser Ser Leu Val Trp Cys Val Leu Ile Val Cys
1               5                   10                  15
```

```
Leu Thr Leu Leu Ile Phe Thr Tyr Leu Thr Arg Lys Ser Leu Cys Glu
             20                  25                  30

Ile Arg Tyr Arg Asp Gly His Arg Glu Val Ala Ala Phe Met Ala Tyr
         35                  40                  45

Glu Ser Gly Lys
     50

<210> SEQ ID NO 48
<211> LENGTH: 159
<212> TYPE: DNA
<213> ORGANISM: Escherichia coli

<400> SEQUENCE: 48
atgaaactac cacgaagttc ccttgtctgg tgtgtgttga tcgtgtgtct cacactgttg      60
atattcactt atctgacacg aaaatcgctg tgcgagattc gttacagaga cggacacagg     120
gaggtggcgg ctttcatggc ttacgaatcc ggtaagtag                            159

<210> SEQ ID NO 49
<211> LENGTH: 225
<212> TYPE: DNA
<213> ORGANISM: Escherichia coli

<400> SEQUENCE: 49
atgtggacta gacataggga tgcctcgtgg tggttaatga aaattaactt actacggggc      60
tatcttcttt ctgccacaca acacggcaac aaaccaccct cacgtcatga ggcagaaagc     120
ctcaagcgcc gggcacatca tagcccatat acctgcacgc tgaccacact cactttccct     180
gaaaataatc cgctcattca gaccgttcac gggaaatccg tgtga                     225

<210> SEQ ID NO 50
<211> LENGTH: 74
<212> TYPE: PRT
<213> ORGANISM: Escherichia coli

<400> SEQUENCE: 50

Met Trp Thr Arg His Arg Asp Ala Ser Trp Trp Leu Met Lys Ile Asn
1               5                   10                  15

Leu Leu Arg Gly Tyr Leu Leu Ser Ala Thr Gln His Gly Asn Lys Pro
             20                  25                  30

Pro Ser Arg His Glu Ala Glu Ser Leu Lys Arg Arg Ala His His Ser
         35                  40                  45

Pro Tyr Thr Cys Thr Leu Thr Thr Leu Thr Phe Pro Glu Asn Asn Pro
     50                  55                  60

Leu Ile Gln Thr Val His Gly Lys Ser Val
65                  70

<210> SEQ ID NO 51
<211> LENGTH: 111
<212> TYPE: PRT
<213> ORGANISM: Escherichia coli

<400> SEQUENCE: 51

Met Val Ser Arg Tyr Val Pro Asp Met Gly Asp Leu Ile Trp Val Asp
1               5                   10                  15

Phe Asp Pro Thr Lys Gly Ser Glu Gln Ala Gly His Arg Pro Ala Val
             20                  25                  30

Val Leu Ser Pro Phe Met Tyr Asn Asn Lys Thr Gly Met Cys Leu Cys
         35                  40                  45
```

```
Val Pro Cys Thr Thr Gln Ser Lys Gly Tyr Pro Phe Glu Val Val Leu
    50                  55                  60

Ser Gly Gln Glu Arg Asp Gly Val Ala Leu Ala Asp Gln Val Lys Ser
65                  70                  75                  80

Ile Ala Trp Arg Ala Arg Gly Ala Thr Lys Lys Gly Thr Val Ala Pro
                85                  90                  95

Glu Glu Leu Gln Leu Ile Lys Ala Lys Ile Asn Val Leu Ile Gly
            100                 105                 110

<210> SEQ ID NO 52
<211> LENGTH: 82
<212> TYPE: PRT
<213> ORGANISM: Escherichia coli

<400> SEQUENCE: 52

Met Ile His Ser Ser Val Lys Arg Trp Gly Asn Ser Pro Ala Val Arg
1               5                   10                  15

Ile Pro Ala Thr Leu Met Gln Ala Leu Asn Leu Asn Ile Asp Asp Glu
                20                  25                  30

Val Lys Ile Asp Leu Val Asp Gly Lys Leu Ile Ile Glu Pro Val Arg
            35                  40                  45

Lys Glu Pro Val Phe Thr Leu Ala Glu Leu Val Asn Asp Ile Thr Pro
    50                  55                  60

Glu Asn Leu His Glu Asn Ile Asp Trp Gly Glu Pro Lys Asp Lys Glu
65                  70                  75                  80

Val Trp

<210> SEQ ID NO 53
<211> LENGTH: 8
<212> TYPE: DNA
<213> ORGANISM: Artificial sequence
<220> FEATURE:
<223> OTHER INFORMATION: E2F binding site

<400> SEQUENCE: 53 tttcccgc                                                              8
```

COMPOSITIONS AND METHODS FOR TREATING CANCER

RELATED APPLICATIONS

This application is a National Phase of PCT Patent Application No. PCT/IL2016/050522 having International filing date of May 17, 2016, which claims the benefit of priority under 35 USC § 119(e) of U.S. Provisional Patent Application No. 62/162,765 filed on May 17, 2015. The contents of the above applications are all incorporated by reference as if fully set forth herein in their entirety.

SEQUENCE LISTING STATEMENT

The ASCII file, entitled 71871SequenceListing.txt, created on Nov. 17, 2017, comprising 25,831 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to nucleic acid constructs and nucleic acid construct systems for treating cancer and, more particularly, but not exclusively, to pharmaceutical compositions and methods using same for treating cancer.

Colorectal cancer (CRC) is a major health concern in the Western world (American Cancer Society. Colorectal Cancer Facts & Figures. 2014). The prognosis for metastatic CRC still remains un-satisfactory. Resistance to chemotherapy is a major obstacle for effective treatment. CRC patients carrying KRAS (KRAS proto-oncogene, GTPase) mutations are a particular therapeutic challenge, due to their resistance to anti-EGFR therapies.

Aberrant activation of the RAS pathway plays an important role in the multistep process of CRC carcinogenesis. Oncogenic RAS stimulates a number of downstream effectors, that activate several transcription factors that bind to the RAS-responsive DNA element and induce early response gene expression. The polyoma (Py) virus enhancer consists flanking overlapping binding sites of the Ets and AP1 transcription factors that are essential for oncogene transcriptional activation (Reddy M A, et al., 1992).

Viral gene therapy is an innovative approach that offers a potential treatment for inherited and acquired diseases (Nabel et al., 2004). It usually involves the generation of replication defective viral particles that are capable of stably or transiently introducing a desirable transgene into cells, resulting in slowing down its' progression (Kootstra N A, et al., 2003; Verma I M, et al., 2005; Young L S, et al., 2006). The most characterized human adenoviruses of serotypes 2 and 5 (Ad2 and Ad5, respectively) usually cause mild upper respiratory tract infections, making them well suited for use in gene therapy.

Adenovirus-based cancer therapy are used for two main strategies: (i) direct tumor cell killing through delivery of replicating oncolytic viruses or non-replicating vectors encoding tumor suppressor genes, suicide genes or anti-angiogenic genes, (ii) destroy primary and metastatic cancer cells through induction of host antitumor immune responses (Kaplan et al., 2005). These approaches offer the potential of selective tumor cell destruction without damage to normal tissues. Apoptotic genes and tumor suppressor genes are used extensively in this field (El-Aneed et al., 2004), alone or in combination with chemotherapy. However, the ability to specifically target tumor cells with gene transfer is limited, and on the other hand, many normal (non-cancerous) cells are affected as well.

Previous studies have shown that recombinant adenovirus carrying the lethal gene PUMA (p53-upregulated modulator of apoptosis) (generous gift of Bert Vogelstein, Johns Hopkins University, Baltimore) under the control of Ets and AP1-RAS-responsive elements (Py2-SV40-PUMA) suppressed the growth of a variety of tumor cells harboring mutated RAS (Dvory-Sobol H, et al., 2005; Dvory-Sobol H, et al. 2006; Dvory-Sobol H, et al. 2007; Giladi N, et al. 2007; Naumov I, et al. 2012; FitzGerald D, et al., 1991).

The present inventors have also recently shown that the addition of multiple RAS-responsive elements (Py4/Py5-SV40-PUMA) further improved the growth inhibitory potency of the construct and induced apoptosis in CRC and pancreatic cancer cells in vitro and in vivo (Naumov I, et al. 2012; Lisiansky V, et al. 2012). However, escape mechanisms and increased expression of anti-apoptotic genes can render the cells resistant as the induced programmed cell death pathway can be inactivated.

MazF is a bacterial ribonuclease known to have specificity for ACA sequences in single-stranded RNA. MazF-induced toxicity is executed by blocking de novo protein synthesis through its endoribonuclease activity, termed mRNA interferases (Inouye et al., 2006). In nature, MazF is one of a pair of genes encoding for a stable toxin and an unstable antitoxin organized in a bicistronic operon as a part of a flexible genome (Pandey et al., 2005). The antitoxin interferes with the lethal action of the toxin and neutralizes it s toxicity (Engelberg-Kulka H, et al., 2006; Engelberg-Kulka H, et al., 2005). This organization is a hallmark of toxin-antitoxin (TA) operons. TA systems are evolutionarily successful entities that are prevalent in lower organisms, bacteria and archaea, and they play important roles in a diverse range of cellular activities (Cook et al., 2013). Some TA systems might behave as selfish elements (found in plasmids), while others integrate into host regulatory networks (encoded from the chromosome). The first TA system to be identified was shown to play a role in plasmid maintenance (Thisted T, et al. 1994; 13:1960-8). Once a cell loses the plasmid encoding the TA system, the toxin will be released from the existing TA complex, given that the antitoxin is more unstable than the toxin. This results in cell growth inhibition that eventually leads to cell death (Gerdes K, et al., 1986).

Additional background art includes Shapira et al 2013 Cancer Res. 73:3303.

SUMMARY OF THE INVENTION

According to an aspect of some embodiments of the present invention there is provided a nucleic acid construct comprising:

(i) a first nucleic acid sequence encoding a toxin operatively linked to a first promoter and at least one cancer-associated proliferative signaling responsive enhancer element;

(ii) a second nucleic acid sequence encoding an anti-toxin operatively linked to a second promoter, the second promoter being stronger than the first promoter.

According to an aspect of some embodiments of the present invention there is provided a nucleic acid construct system comprising:

(i) a first nucleic acid construct encoding a toxin operatively linked to a first promoter and at least one cancer-associated signaling responsive enhancer element;

(ii) a second nucleic acid construct encoding an anti-toxin operatively linked to a second promoter, the second promoter being stronger than the first promoter.

According to an aspect of some embodiments of the present invention there is provided a nucleic acid construct system comprising:

(i) a first nucleic acid construct encoding a toxin operatively linked to a first promoter and at least one cancer-associated signaling responsive enhancer element;

(ii) a second nucleic acid construct encoding an anti-toxin operatively linked to a second promoter;

wherein the first nucleic acid construct is provided at a higher concentration than the second nucleic acid construct.

According to an aspect of some embodiments of the present invention there is provided a method of treating cancer comprising, the method comprising introducing into the cancer cells the nucleic acid construct of some embodiments of the invention, or the nucleic acid construct system of some embodiments of the invention, wherein the cancer cells are characterized by hyper activity of the signaling as compared to non-cancerous cells of the same tissue, thereby treating the cancer.

According to an aspect of some embodiments of the present invention there is provided a pharmaceutical composition comprising the nucleic acid construct of some embodiments of the invention or the nucleic acid construct system of some embodiments of the invention, and a pharmaceutically acceptable carrier or diluents.

According to an aspect of some embodiments of the present invention there is provided a composition comprising the nucleic acid construct of some embodiments of the invention, or the nucleic acid construct system of some embodiments of the invention for use in treating cancer, wherein cells of the cancer are characterized by hyper activity of the signaling as compared to non-cancerous cells of the same tissue.

According to some embodiments of the invention, the second promoter comprises CMV and the first promoter comprises SV40.

According to some embodiments of the invention, the nucleic acid construct is adeno-virus based.

According to some embodiments of the invention, the nucleic acid construct is Lenti-virus based.

According to some embodiments of the invention, the cancer-associated signaling responsive enhancer element comprises a Ras-responsive element.

According to some embodiments of the invention, the Ras-responsive element comprises the Ets binding site and/or Ap-1 binding site.

According to some embodiments of the invention, the Ets binding site is set forth by SEQ ID NO:1.

According to some embodiments of the invention, the Ap-1 binding site is set forth by SEQ ID NO:2.

According to some embodiments of the invention, the Ras-responsive element comprises the PY2 sequence.

According to some embodiments of the invention, the Ras-responsive element comprises at least four repeats of the PY2 sequence.

According to some embodiments of the invention, the PY2 sequence is set forth by SEQ ID NO:3.

According to some embodiments of the invention, the first nucleic acid construct and the nucleic acid construct are co-transfected into cells at a 1 to 0.5 ratio, respectively.

According to some embodiments of the invention, the Ras comprises K-Ras.

According to some embodiments of the invention, the anti-toxin comprises an RNA silencing agent.

According to some embodiments of the invention, the toxin and the anti-toxin comprise a bacterial-derived toxin anti-toxin system.

According to some embodiments of the invention, the toxin anti-toxin system comprise a MazEF system.

According to some embodiments of the invention, the second nucleic acid sequence or the second nucleic acid construct further comprises a non-cancerous associated responsive element for regulating transcription of the anti-toxin.

According to some embodiments of the invention, the non-cancerous associated responsive element comprises the p53 wild type responsive element.

According to some embodiments of the invention, the p53 wild type responsive element is set forth by SEQ ID NO:14.

According to some embodiments of the invention, the second nucleic acid sequence or the second nucleic acid construct comprises at least 2 repeats of the non-cancerous associated responsive element.

According to some embodiments of the invention, the second nucleic acid sequence or the second nucleic acid construct comprises 17 repeats of the p53 wild type responsive element.

According to some embodiments of the invention, the first nucleic acid sequence or the first nucleic acid construct further comprises a repressor of a bacterial repressor-operator system, the repressor being under a transcriptional regulation of the cancer-associated signaling responsive enhancer element, and wherein the second nucleic acid sequence or construct comprises an operator of the bacterial repressor-operator system, such that expression of the repressor inhibits expression of the antitoxin.

According to some embodiments of the invention, the repressor comprises the Tetracycline repressor (Tet-R) sequence, and wherein the operator comprises the tetracycline operator sequence.

According to some embodiments of the invention, the operator comprises at least two repeats of the sequence tetracycline operator sequence.

According to some embodiments of the invention, the first nucleic acid sequence or the first nucleic acid construct comprises four repeats of the PY2 sequence set forth by SEQ ID NO:2 being upstream and operably linked to the SV40 minimal promoter region set forth by SEQ ID NO:4, a toxin coding sequence being downstream of and transcriptionally regulated by the SV40 minimal promoter region, an IRES sequence set forth by SEQ ID NO:7 being downstream and operably linked to the toxin coding sequence, and a Tetracycline repressor set forth by SEQ ID NO: 8 being downstream of and operably linked to the IRES sequence.

According to some embodiments of the invention, the second nucleic acid sequence or the second nucleic acid construct comprises a CMV minimal promoter which comprises two repeats of a tetracycline operator as set forth by SEQ ID NO:9 and an antitoxin coding sequence being downstream of and operably linked to the CMV minimal promoter.

According to some embodiments of the invention, the second nucleic acid sequence or the second nucleic acid construct comprises at least one copy of the p53 wild type responsive element set forth by SEQ ID NO:14.

According to some embodiments of the invention, the second nucleic acid sequence or the second nucleic acid construct comprises 17 copies of the p53 wild type responsive element, wherein the 17 copies of the p53 wild type responsive element are set forth in SEQ ID NO:15.

According to some embodiments of the invention, the cancer comprises colon cancer.

According to some embodiments of the invention, the cancer comprises lung cancer.

According to some embodiments of the invention, the cancer comprises pancreatic cancer.

According to some embodiments of the invention, the cancer comprises gastric cancer.

According to some embodiments of the invention, the cancer is characterized by a hyperactive RAS GTPase activity.

According to some embodiments of the invention, the RAS is a KRAS protein and wherein the hyperactive KRAS is caused by a G13D mutation in the KRAS protein set forth by SEQ ID NO:16.

According to some embodiments of the invention, the RAS is a NRAS protein and wherein the hyperactive NRAS is caused by a Q61K mutation in the NRAS protein set forth by SEQ ID NO:17.

According to some embodiments of the invention, the RAS is a HRAS protein and wherein the hyperactive HRAS is caused by a G12V mutation in the HRAS protein set forth by SEQ ID NO:18.

According to some embodiments of the invention, the method further comprising treating a subject having the cancer by a treatment selected from the group consisting of: chemotherapy, biological therapy, radiotherapy, phototherapy, photodynamic therapy, surgery, nutritional therapy, ablative therapy, combined radiotherapy and chemotherapy, brachiotherapy, proton beam therapy, immunotherapy, cellular therapy and photon beam radiosurgical therapy.

According to some embodiments of the invention, the composition further comprising an agent suitable for a treatment selected from the group consisting of: chemotherapy, biological therapy, photodynamic therapy, nutritional therapy, brachiotherapy, immunotherapy, and cellular therapy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

The patent or application file contains at least one drawing executed in color. Copies of this patent or patent application publication with color drawing(s) will be provided by the Office upon request and payment of the necessary fee.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-I depict MazF cassette. FIG. 1A—A schematic illustration of the mazF cassette. The RRE-activated MazF cassette was constructed by cloning several elements in the following order (from the N terminus): four repeats of the RAS responsive, Ets (SEQ ID NO:1) and AP-1 (SEQ ID NO:2) binding sites (termed "py2", SEQ ID NO: 3); SV40 minimal promoter (SEQ ID NO:4); monomeric red fluorescence protein mCherry (SEQ ID NO:5); E. coli MazF ribonuclease (SEQ ID NO:6). FIGS. 1B-F—The toxic effect of the mazF-encoding viruses. $1 \times 10^4$ HCT116 cells were seeded in 96-well plates in complete medium. Median dilutions of the MazF-encoding viruses starting from 25 MOI were added to the cells on the next day. FIGS. 1B-E—images from a light microscopy (FIGS. 1B-C) and from a fluorescent microscopy (FIGS. 1D-E) depicting cell survival (all of the microscope images are of the same magnification). FIG. 1F—a histogram depicting quantification of cell survival based on an enzymatic MTT assay 72 hours after infection. Each bar represents the mean±SD of a set of data determined in triplicates. FIGS. 1G-H—$1 \times 10^5$ cells were seeded in 12-well plates in complete medium and infected with the different adenoviruses in 20 MOI for 72 hours. Cell death was measured by FACS after staining with Annexin V (FIG. 1G) and RedDot2 (FIG. 1H) dyes. FIG. 1I—a histogram depicting reporter gene expression (luciferase) under the transcriptional regulation of the SV40 promoter and the PY4 Ras-responsive element in HCT116 cells. Briefly, a nucleic acid construct which comprises the PY4 Ras-responsive element upstream of the SV40 promoter being operably linked to a luciferase (reporter gene) coding sequence was used for transfection of HCT116 cells in which Ras is hyperactive. $5 \times 10^5$ HCT116 cells were seeded in 6-well plates. The next day, when the cells were about 50% confluent, co-transfection with 3 µg (microgram) of PY4-SV40-LUC vector plus 0.3 ng (nanogram) of pRL-CMV (Promega) was performed using jetPEI™ (Polyplus-transfection Inc, NY, USA) according to the manufacturer's instructions. The Luc activity was normalized to *Renilla* Luc activity from a parallel co-transfection.

Figure 2C:
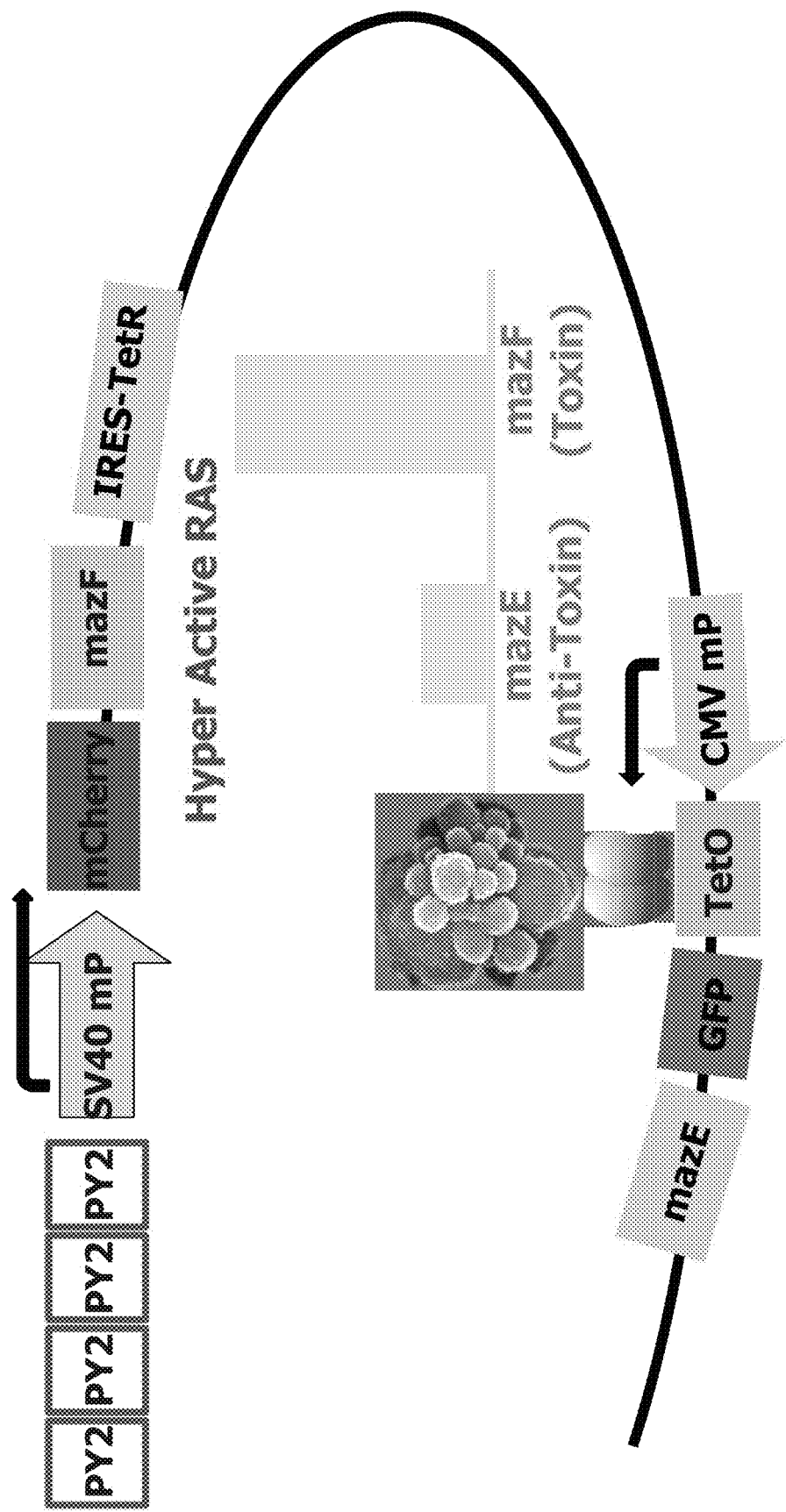
Figure 2D:
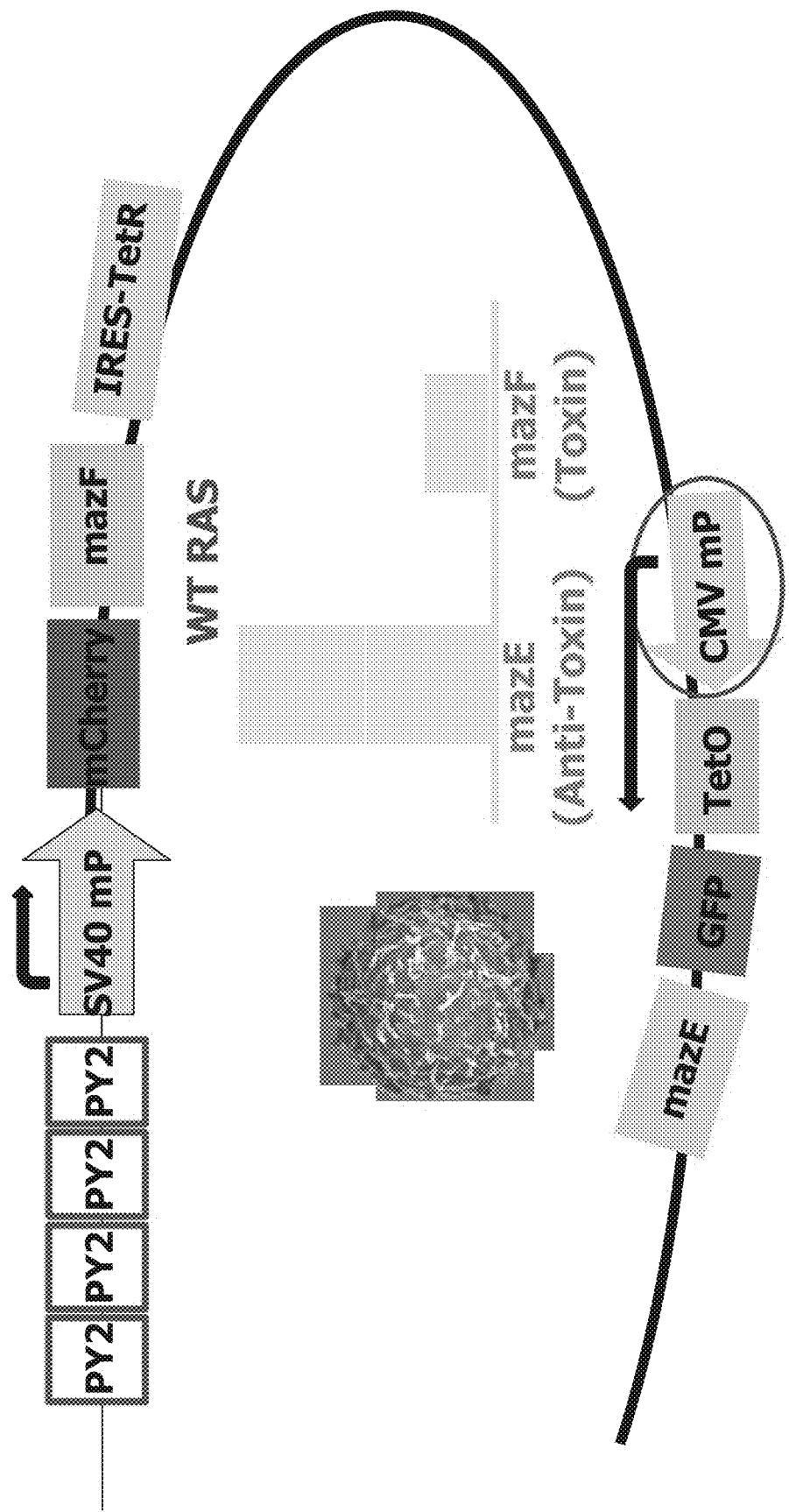
Figure 2E:
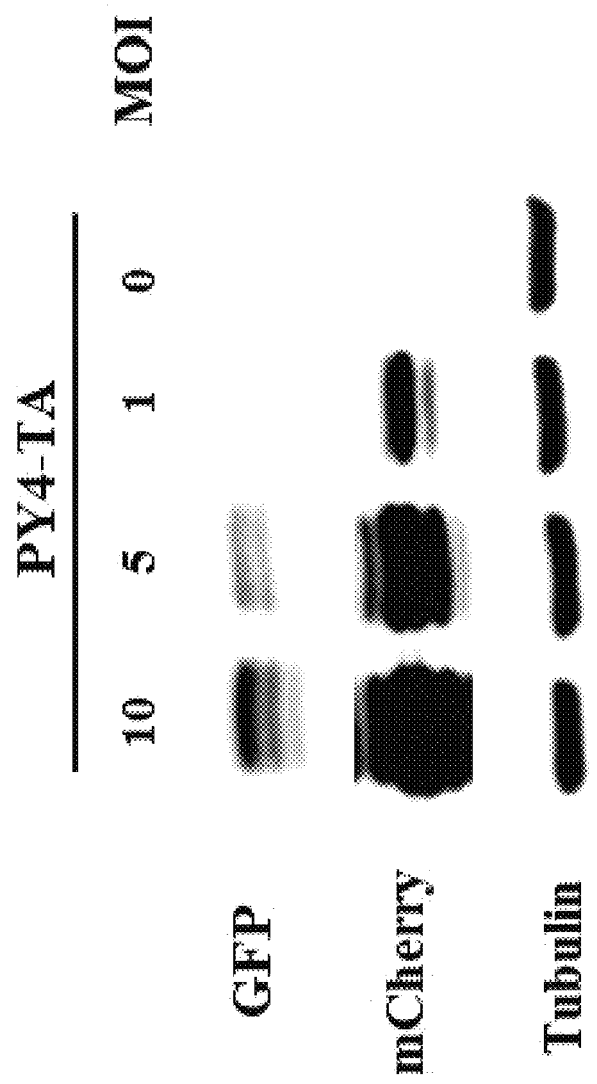

FIGS. 2A-E depict the MazEF cassette. FIG. 2A-A schematic illustration of the mazEF cassette with the Ras-responsive elements PY2. This construct is also referred to as "PY4-TA" or "pAdEasy-Py4-TA" hereinafter. The Ras-responsive element (RRE)-activated MazEF cassette was constructed by cloning several elements in the following order (from the N-terminus to the C-terminus): four repeats of "Py2" [comprising the Ras responsive Ets (SEQ ID NO:1) and AP-1 (SEQ ID NO:2) binding sites]; SV40 minimal promoter (SEQ ID NO:4); monomeric red fluorescence protein mCherry coding sequence (SEQ ID NO:5); *E. coli* MazF ribonuclease (SEQ ID NO:6); internal ribosome entry sites ("IRES", SEQ ID NO: 7); tetracycline repressor coding sequence (SEQ ID NO:8); CMV minimal promoter with two copies of the tetracycline operator (SEQ ID NO:9; the sequence of the tetracycline operator is provided in SEQ ID NO:11); green fluorescence protein coding sequence (SEQ ID NO:12); *E. coli* antitoxin MazE coding sequence (SEQ ID NO:13). FIG. 2B depicts the same construct as in FIG. 2A, yet devoid of the Ras-responsive element Py2. This construct is also referred to as "ΔPY4-TA" hereinafter). FIG. 2C-A schematic illustration depicting the proposed mode of action of the PY4-TA construct (depicted in FIG. 2A) in cells characterized by a hyperactive Ras. The PY2 elements bind transcription factors in Ras hyperactive cells, leading to expression of the mazF toxin and the tetracycline repressor (TetR; shown in pink), which then binds to the tetracycline operator and interferes (e.g., blocks) with the expression the maze antitoxin under the control of the CMV minimal promoter. As a result, the expression of the mazF toxin is higher than the expression of the mazE antitoxin and the cells are doomed to die. FIG. 2D-A schematic illustration depicting the proposed mode of action of the PY4-TA construct (depicted in FIG. 2A) in cells characterized by a wild type Ras (i.e., not hyperactive Ras). Since the cells do not include an hyperactive Ras, the PY2 sites do not activate the transcription of the mazF toxin, nor the expression of the TetR which is downstream of the mazF toxin coding sequence, and as a result, the activity of MazF is inhibited as compared to the activity of the antitoxin mazE, thus ensuring the survival of cells having wild type Ras. FIG. 2E—Western blot analysis depicting expression of the reporter proteins GFP (which is translationally fused to the antitoxin mazE coding sequence) and mCherry (which is translationally fused to the toxin mazF coding sequence) in cells characterized by a hyperactive Ras at increasing MOIs (multiple of infection). Thus, when the MOI equals to "1" (a single virus particle infecting a single cell) there is only expression of the mCherry reporter protein, indicating expression of only the mazF toxin. At increasing MOI to "5" (5 virus particles infecting a single cell), there is also "leakage" of expression of the GFP reporter protein, indicating some degree of expression of the antitoxin maze, yet the expression of the mCherry is significantly higher.

FIGS. 3A-K—Cells having wild type Ras are protected from the cytotoxicity of MazF due to MazE expression. HT29 cells, with WT (wild type) RAS, were seeded in 96-well plates. After 24 hours, two-fold dilutions of recombinant adenoviruses encoding for MazF or MazEF were added for 72 hours. Qualitative examination was performed using light microscopy (left images in each of FIGS. 3A-K) and fluorescence microscopy showing expression of mCherry (red fluorescent, middle images in each of FIGS. 3A-K) or GFP (green fluorescent, right images in each of FIGS. 3A-K). Microscopic Magnification ×100. FIG. 3A—uninfected cells; FIGS. 3B-C—cells were infected with 1.56 MOI of recombinant adenoviruses harboring the MazEF vector (FIG. 3B) or the MazF vector (FIG. 3C). FIGS. 3D-E—cells were infected with 3.12 MOI of recombinant adenoviruses harboring the MazEF vector (FIG. 3D) or the MazF vector (FIG. 3E). FIGS. 3F-G—cells were infected with 6.25 MOI of recombinant adenoviruses harboring the MazEF vector (FIG. 3F) or the MazF vector (FIG. 3G). FIGS. 3H-I—cells were infected with 12.5 MOI of recombinant adenoviruses harboring the MazEF vector (FIG. 3H) or the MazF vector (FIG. 3I). FIGS. 3J-K—cells were infected with 25 MOI of recombinant adenoviruses harboring the MazEF vector (FIG. 3J) or the MazF vector (FIG. 3K). Note the decrease in expression of mCherry in cells infected with the MazF vector as compared to the expression of mCherry in cells infected with the MazEF vector. Also note the inhibition of cell growth in cells infected with the MazF vector as compared to the cell growth in cells infected with the MazEF vector. When visualized under a fluorescence microscope, the intoxicated Ad-Py4-SV40-mCherry-MazF-infected cells showed very faint red fluorescence, indicating inefficient mCherry-MazF accumulation. This is due to the ribonuclease activity of MazF that results in inhibition of protein synthesis, including its own (Zhang Y, MazF cleaves cellular mRNAs specifically at ACA to block protein synthesis in *Escherichia coli*. Mol Cell 2003; 12:913-23' Shapira A, Removal of hepatitis C virus-infected cells by a zymogenized bacterial toxin. PLoS One 2012; 7:e32320). On the other hand, the ribonuclease activity of MazF was neutralized by its antidote MazE in cells infected with pAdEasy-Py4-TA, as indicated by the presence of both red and green fluorescence.

FIGS. 4A-G depict eradication of R1 cells by recombinant adenovirus-mediated delivery of the PY4-TA (which includes the MazF-MazE) encoding cassette. FIG. 4A—A schematic illustration depicting the construction of the mCherry control cassette by cloning the monomeric red fluorescence protein mCherry (SEQ ID NO:5) downstream to the CMV promoter. $1 \times 10^4$ R1 cells were seeded in 96-well plates. After 24 hours, two-fold dilutions of recombinant adenoviruses encoding for PY4-TA (MazF-MazE) or mCherry were added for 72 hours. FIGS. 4B-D—Representative pictures of uninfected cells (control, FIG. 4B) and cells that were infected with the PY4-TA cassette with 5 MOI (FIG. 4C) or 10 MOI (FIG. 4D) (magnification of ×100 in all microscopic images). FIG. 4E-A histogram depicting quantification of enzymatic MTT viability assay which were performed 72 hours post-infection. Cell survival was measured in R1 cells infected with mCherry (black bars, "R1 mCherry") or the PY4-TA (white bars, "R1 TA") at the infected MOI. The relative fraction of viable cells (relative to uninfected controls) was determined by MTT assay. Each bar represents the mean±SD of a set of data determined in triplicates. FIGS. 4F-G—fluorescence microscopic examination of the infected cells (5 MOI of PY4-TA encoding viruses) showing expression of mCherry (FIG. 4F, red staining) and GFP (FIG. 4G, green staining) of the same microscopic field.

FIGS. 5A-J depict a colony formation assay showing selective eradication of CRC cells by recombinant adenovirus-mediated delivery of the mazEF encoding cassette. On the day before infection, $5 \times 10^5$ HCT116 (which include an hyperactive Ras) and HT29 (which include wild type Ras) cells were seeded in 6-well plates and subsequently infected with 25 and 10 MOI of the viruses "pAdEasy-Py4-mCherry-MazF-IRES-TetR-CMVmp (with the Tet operator)-MazE-IRES-EGFP" (labeled as "PY4-TA") and "pAdEasy-SV40-mCherry-MazF-IRES-TetR-CMVmp-MazE-IRES-EGFP" (labeled as "ΔPY4-TA") or left un-infected. After 7 hours, the cells were trypsinized and seeded at 3-fold dilutions and incubated for 7 days. Surviving colonies were stained with 0.02% crystal violet. Note the significant decrease in survival cells treated with the PY4-TA vector at both MOI concentrations in HCT116 cells as compared to the cells treated with the ΔPY4-TA vector. Also, it is noted that the cell growth of the HT29 cells were not affected by treatment with either one of the vectors, thus showing the specificity of the PY4-TA vectors for killing cancer cells such as HCT116 cells with hyperactive Ras and not HT29 cells which have wild type KRAS gene.

FIGS. 6A-P—$1 \times 10^4$ HCT116 and HT29 cells were seeded in 96-well plates. After 24 hours, two-fold dilutions of recombinant adenoviruses PY4-TA encoding for mazEF were added. FIGS. 6A-D—Microscopic examination of the uninfected cells. FIGS. 6A-B—HCT116 cells; FIGS. 6C-D—HT29 cells. FIGS. 6E-J—Microscopic examination of the infected cells (10 MOI) was performed 72 hours post-infection. FIGS. 6E-G—HCT116 cells. FIGS. 6H-J—HT29 cells. Shown is a light microscopy (FIGS. 6E and 6H), and fluorescent microscopy showing mCherry expression (FIGS. 6F and 6I) and GFP expression (FIGS. 6G and 6J). Note the significant decrease in mCherry and GFP expression in HCT116 cells treated with the PY4-TA (mazEF) vector as compared to HT29 cells treated with the same PY4-TA (mazEF) vector. FIG. 6K-A histogram depicting cell survival of HCT116 cells (empty bars) or HT29 cells (black bars) treated with the same PY4-TA (mazEF) vector at various MOI. Cell survival was determined by an enzymatic MTT viability assay, and the relative fraction of viable cells (relative to uninfected controls) was determined. Each bar represents the mean±SD of a set of data determined in triplicates. FIGS. 6L-O-HT29 cells were infected (10 MOI) in the presence (FIGS. 6N and 6O) or absence (FIGS. 6L and 6M) of 1 µg/ml tetracycline. The cells were examined using a microscope 72 hour post-infection. FIG. 6P—$1 \times 10^4$ HCT116 cells (having hyperactive Ras) were seeded in 96-well plates. The Ad-Py4-TA encoding viruses were added in several MOIs with (empty bars) or without (filled bars) 1 µg/ml tetracycline 24 hours later. The enzymatic MTT viability assay was performed after 72 hours. Size bars=200 µm in all microscopic images shown in FIGS. 6A-J; the images shown in FIGS. 6L-O were taken using the same magnification as those in FIGS. 6A-J).

FIGS. 7A-C depict FACS analyses (FIGS. 7A-B) and cell survival (FIG. 7C) of cells infected with the PY4-TA or ΔPY4-TA vectors. $1 \times 10^5$ HCT116 cells were seeded in 12-well plates in complete medium and infected with the different adenoviruses at 10 MOI for 72 hours. FIGS. 7A-B—FACS analyses showing cell death after staining with Annexin V (FIG. 7A) or RedDot2 (FIG. 7B) dyes. In both analyses (FIGS. 7A-B) the untreated cells are shown in red, the toxin antitoxin-treated cells (infected with the PY4-TA vector) are shown in black, and the cells that were treated with the RRE deletion cassette (ΔPY4-TA) are shown in green. Note the increase in cell death in cells treated with the PY4-TA vector as compared to cells treated with the control ΔPY4-TA vector devoid of the PY4 elements. FIG. 7C-A histogram depicting cell survival following infection with the PY4-TA vector or the ΔPY4-TA vector. $1 \times 10^4$ HCT116 cells were seeded in 96-well plates. After 24 hours, two-fold dilutions of recombinant adenoviruses encoding for Py4-TA (empty bars) or ΔPy4-TA (filled bars) were added for 72 hours. The relative fraction of viable cells (relative to uninfected controls) was determined by MTT assay. Each bar represents the mean±SD of a set of data determined in triplicates.

FIGS. 8A-C depict inhibition of tumor growth in mice. Tumors were formed in nude mice by subcutaneous injection of $5 \times 10^6$ HCT116 cells on day 0 and were treated twice with intraperitoneal $2 \times 10^9$ PFU/mouse of the indicated viruses. FIG. 8A-A graph depicting fold increase of tumor size in mice treated with the various viruses. Tumor size was measured at the indicated time points and tumor volumes were calculated. The mean values for each group are shown, and the standard deviation is represented by error bars for each measurement. The P values for the ΔPy4-TA group compared to the PBS group are shown in red and those for the Py4-TA group compared to the PBS group are shown in green. Each bar represents the mean±SD of a set of data determined from six mice. FIGS. 8B-C—Imaging was performed on the living organism with the Maestro CRi imaging device (FIG. 8B) and outside the mouse body (FIG. 8C). The red fluorescence dye represents the expression of MazF and the green fluorescence dye represents the expression of MazE.

Figure 9A:
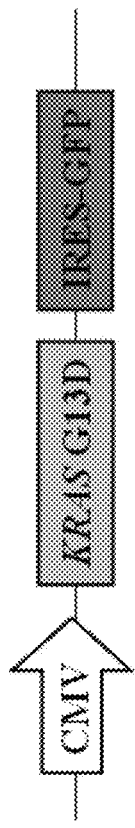
Figure 9C:
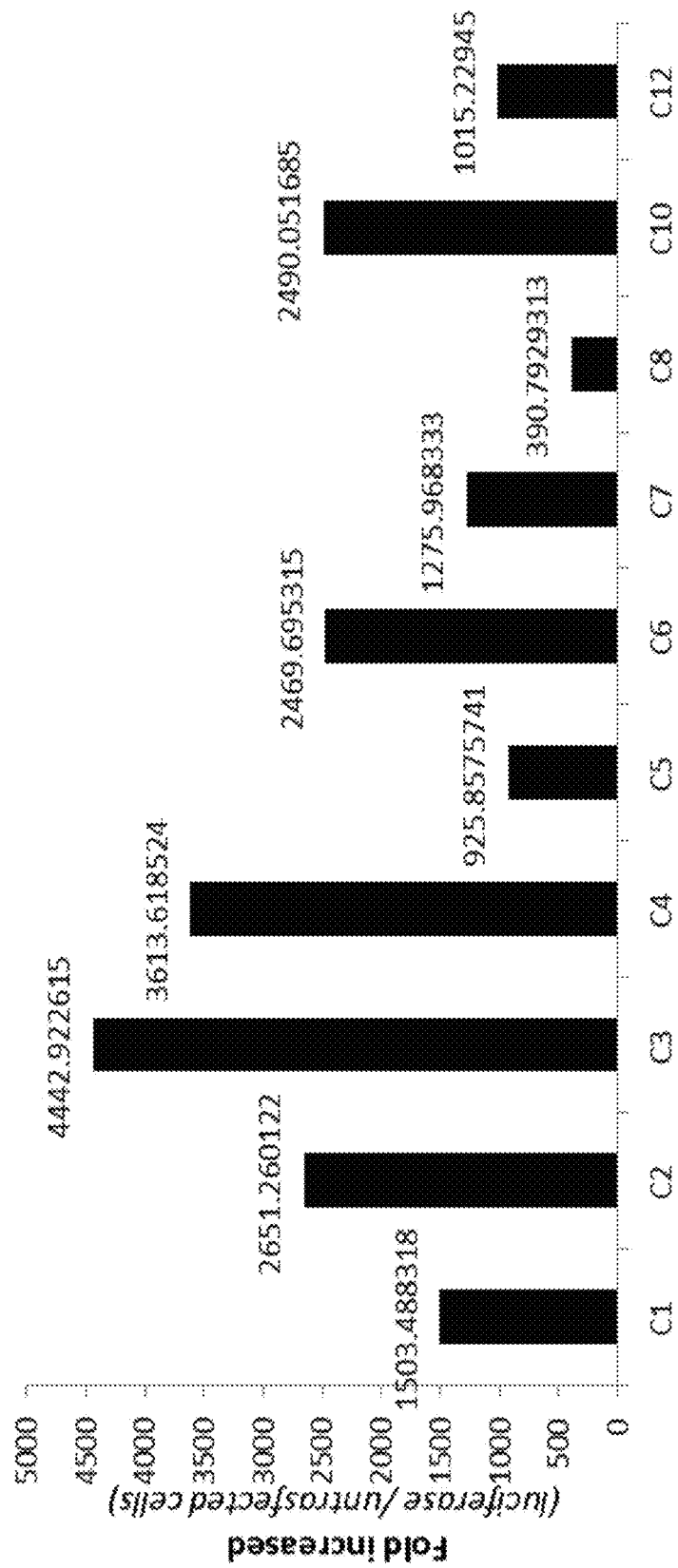
Figure 9B:
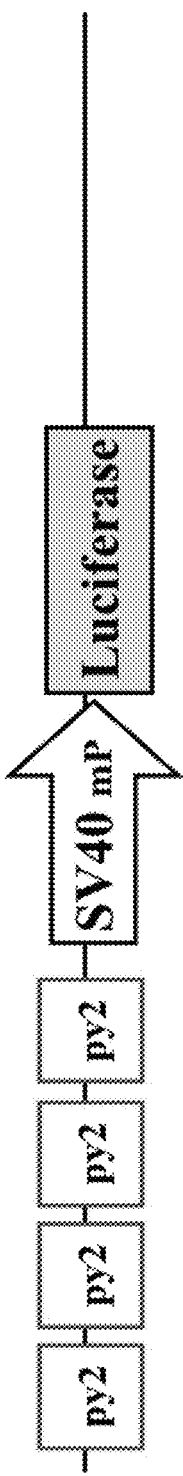

FIGS. 9A-C depict the cloning of a mutated KRAS. Mouse cells were stably transfected with the plasmid described in FIG. 9A, thus expressing the mutated KRAS in their genome resulting in a hyperactive ras in the cells. The cells were then transiently transfected with the luciferase construct described in FIG. 9B to test for clones having increased luciferase expression as a result of the binding of the PY4 ras enhancer elements to the transcription factors downstream of the KRAS hyperactive signaling pathway in the mouse cells. FIG. 9A—Schematic illustration of the KRAS G13D cassette. The mutated kras cassette was constructed by cloning of the KRAS gene [mutation in the coding sequence of amino acid at position 13 in which G (glycine) was replaced by D (aspartic acid)] downstream to the CMV promoter. IRES-GFP sequences were cloned downstream to the KRAS gene. FIG. 9B—Schematic illustration of a construct in which the luciferase coding sequence (SEQ ID NO:20) is under the regulation of the PY4 ras enhancer elements and the SV40 minimal promoter. FIG. 9C-A histogram depicting the fold increase of luciferase expression in the various clones. It is noted that clone C3 exhibits the highest expression of luciferase.

FIG. 10 is a Western blot analysis depicting the expression of GFP in tumors infected with AAV6 particles. Tumors were induced (derived from HT29 cell line) in nude mice. Then a systemic single infecting of the various serotypes in several titers was conducted, and after two weeks the mice were sacrificed, the tumors were removed and the expression of the GFP was evaluated by Western blot analysis.

Figure 11A:
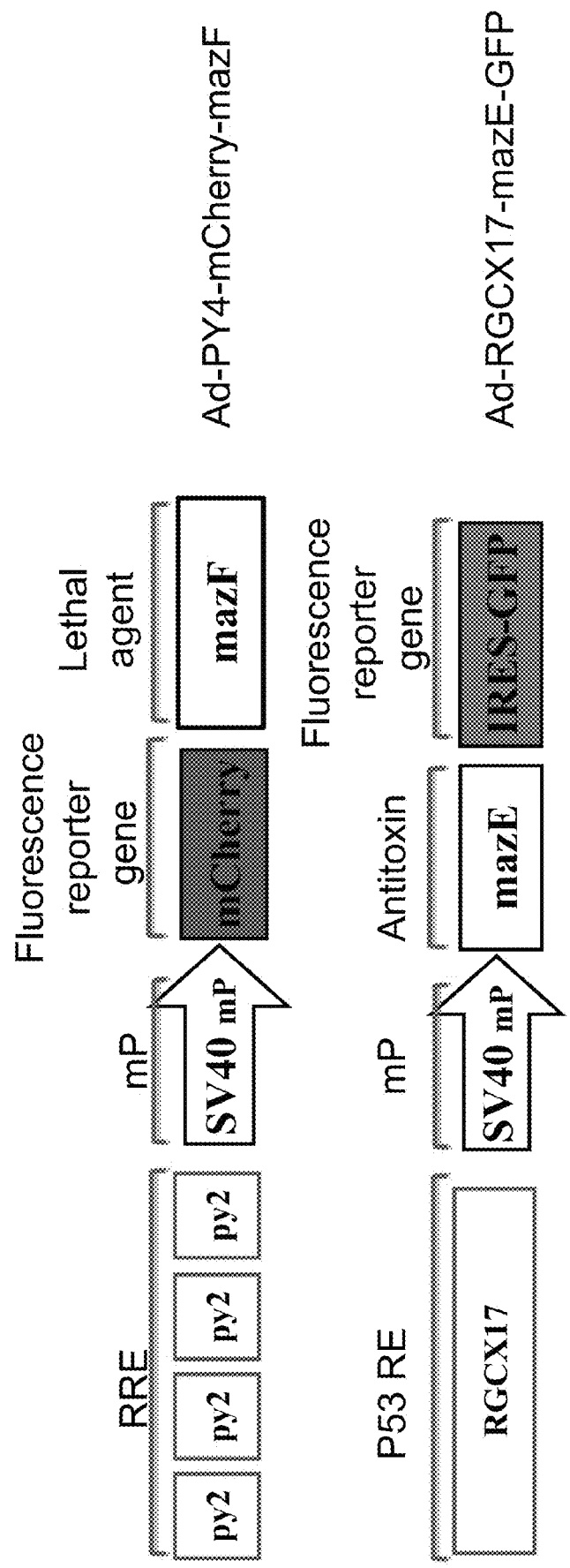
Figure 11B:
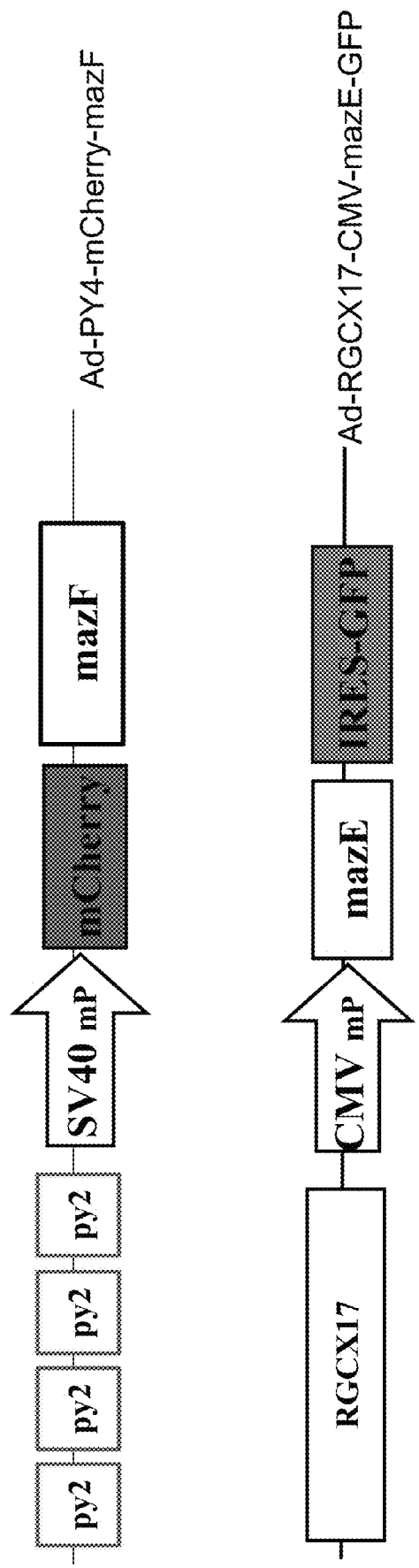

FIGS. 11A-B are schematic illustrations of nucleic acid construct systems according to some embodiments of the invention. FIG. 11A—Shown in a dual system based on the Ras and p53 responsive elements. The first nucleic acid construct (Ad-PY4-mCherry-mazF) comprises 4 repeats of the PY2 ras enhancer element, followed by the SV40 minimal promoter, followed by the mCherry coding sequence and the mazF toxin; and the second nucleic acid construct (Ad-RGCX17-mazE-GFP) comprises the p53 wild type responsive element, followed by the SV40 minimal promoter, followed by the mazE antitoxin coding sequence and the GFP fluorescence reporter gene. FIG. 11B—Shown in a dual system based on the Ras and p53 responsive elements. The first nucleic acid construct (Ad-PY4-mCherry-mazF) comprises 4 repeats of the PY2 ras enhancer element, followed by the SV40 minimal promoter, followed by the mCherry coding sequence and the mazF toxin; and the second nucleic acid construct (Ad-RGCX17-CMV-mazE-GFP) comprises the p53 wild type responsive element, followed by the CMV minimal promoter (without the Tet operator), followed by the mazE antitoxin coding sequence and the GFP fluorescence reporter gene.

Figure 12:
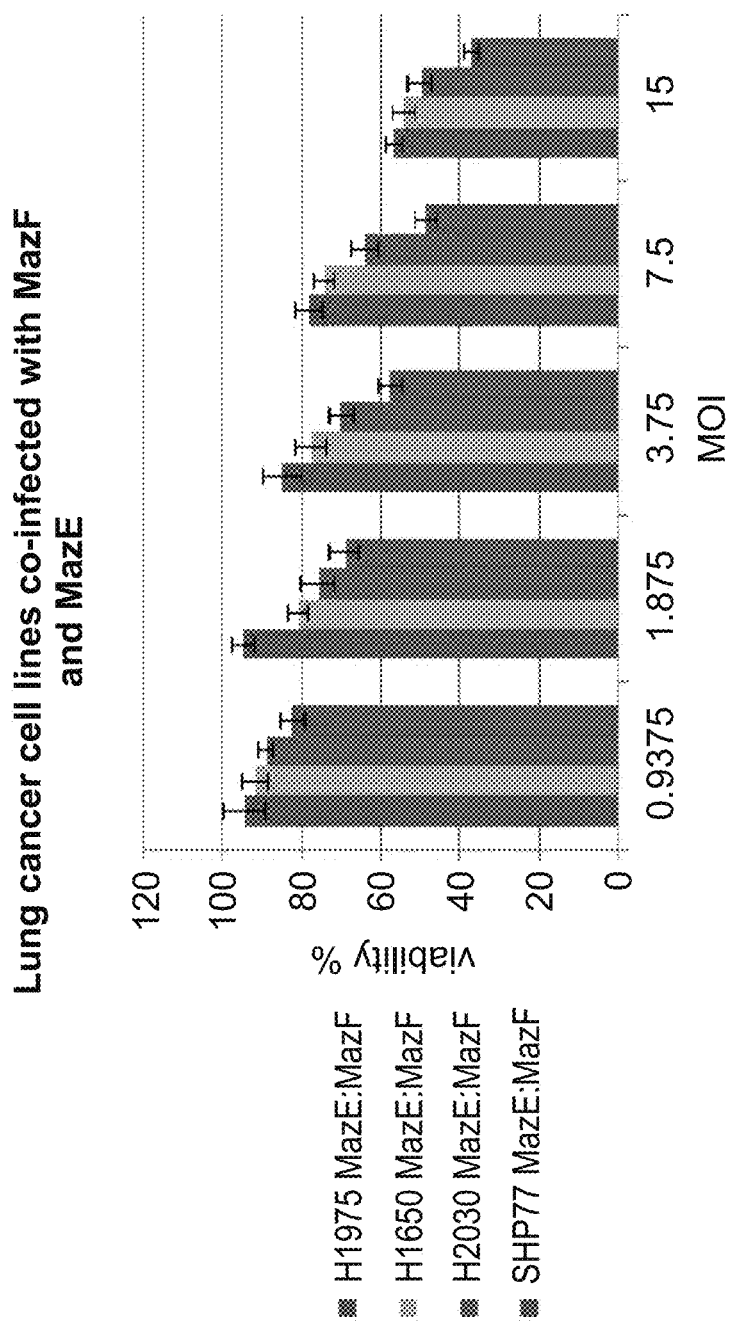

FIG. 12 is a histogram depicting cell viability (determined by an MTT assay) of lung cancer cell lines after co-infection with MazF and MazE in an MOI ratio of 1:0.5, respectively. It should be noted that in this experiment both the MazF and MazE constructs were under the transcriptional regulation of the SV40 minimal promoter. H1975 cells: $Ras^{wt}/p53^{mut}$; H1650 cells: $Ras^{wt}/p53^{mut}$; H2030 cells: $Ras^{mut}/p53^{mut}$; SHP77 cells: $Ras^{mut}/p53^{mut}$.

Figure 13A:
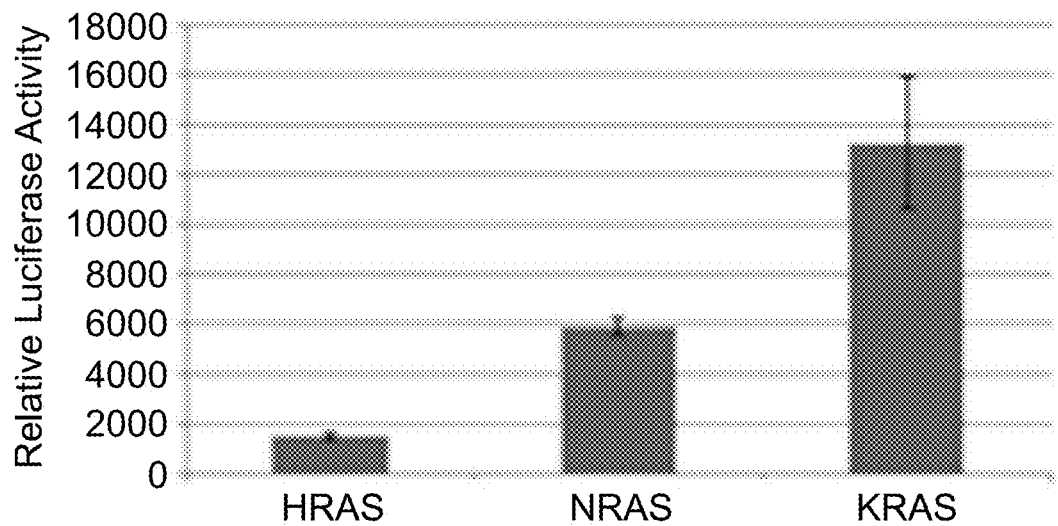
Figure 13B:
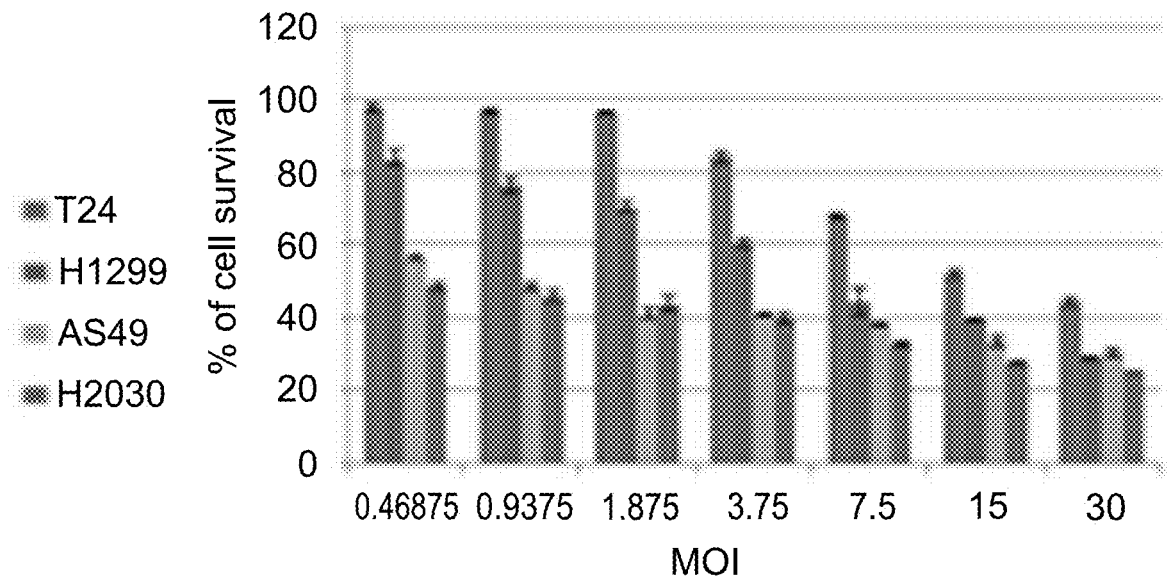

FIGS. 13A-B are histograms depicting luciferase assay (FIG. 13A) and an MTT assay (FIG. 13B). FIG. 13A—The activity of the PY4 Ras-responsive element was tested in H1299 (NRAS oncogene expressing cell line), A549 (KRAS oncogene expressing cell line) and T24 (HRAS oncogene expressing cell line). The cells were co-transfected with PY4-luciferase and pRL-CMV (Promega) plasmids. The Luciferase activity was normalized to *Renilla* Luc activity from a parallel co-transfection. The results show that PY4 transcription can be activated by 3 Ras variants. FIG. 13B-$1 \times 10^4$ H1299, H2030, A549, and T24 cells were seeded in 96-wells plates. On the next day, cells were infected with Ad-PY4-mCherry-mazF carrying viruses for 72 hours. Cell viability was measured by the MTT assay. The results show that toxin transcription can be activated by 3 Ras variants.

Figures 14A, 14B, 14C:
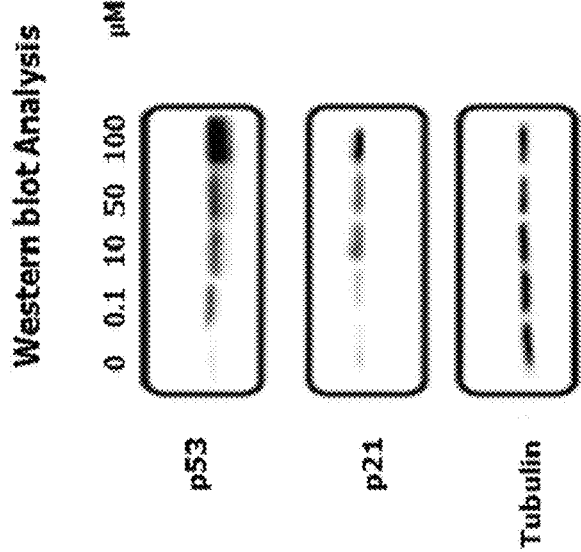

FIGS. 14A-C are Western blot analyses of p53 (FIG. 14A), p21 (FIG. 14B) and Tubulin (FIG. 14C) of HCT116 cells after treatment with 5FU. HCT116 cells were treated with 50 μM 5FU for 24 hours. Then, total cell lysate was prepared and subjected to Western blot analysis for p53 (FIG. 14A) and p21 (FIG. 14B) analysis. Tubulin (FIG. 14C) was used as a loading control and in the analyses of both proteins for normalization.

Figure 15A:
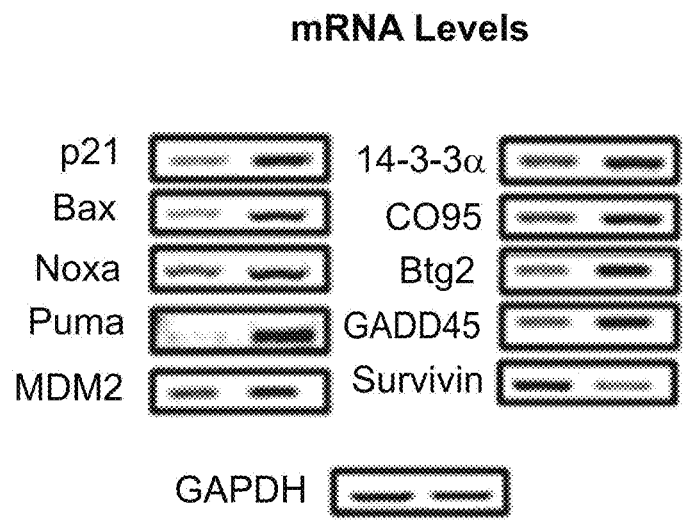
Figure 15B:
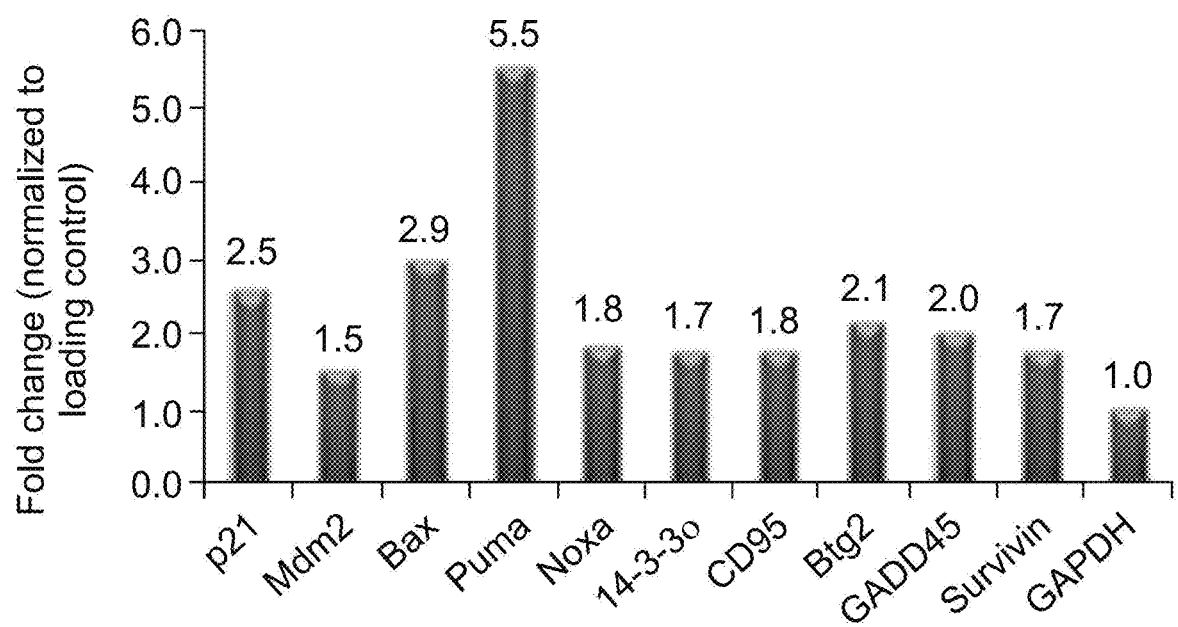

FIGS. 15A-B depict mRNA levels of various transcripts following treatment of HCT116 cells with 5FU. HCT116 cells were treated with 50 μM 5FU for 24 hours. Then, RNA was prepared and used as a template for cDNA and semi-quantitative PCR was performed for the following transcripts: p21, Bax, Noxa, Puma, MDM2, 14-3-3o, CD95, Btg2, GADD45, and Survivin. The graph represents the quantification of mRNA levels performed using the primers listed in Table 2 in the EXAMPLES section which follows.

FIGS. 16A-H depict crystal violet analysis of cells infected with the viruses according to some embodiments of the invention. $5 \times 10^5$ A549 cells (KRAS nut, p53 wild type; FIGS. 16A-D) and H1650 cells (KRAS wild type, p53 wild type) were seeded in 6-well plates. After 24 hours, the cells were infected with 10 MOI of the PY4-mazF-mCherry and RGC-mazE-GFP viruses, in a ratio of 1:0.5, respectively (FIGS. 16A and 16C for A549 cells; and FIG. 16E for H1650 cells). In parallel those cell lines were infected with ΔPY4-mazF-mcherry and RGC-mazE-GFP viruses, in a ratio of 1:0.5, respectively (FIGS. 16B and 16D for A549 cells; and FIG. 16F for H1650 cells). The CMV-mCherry vector was used as a control (FIG. 16G). After 7 hours, the cells were trypsinized and seeded in 3-fold dilutions and incubated for 7 days. Surviving colonies were fixed with 4% formaldehyde in PBS and stained with 0.02% crystal violet.

Figure 17:
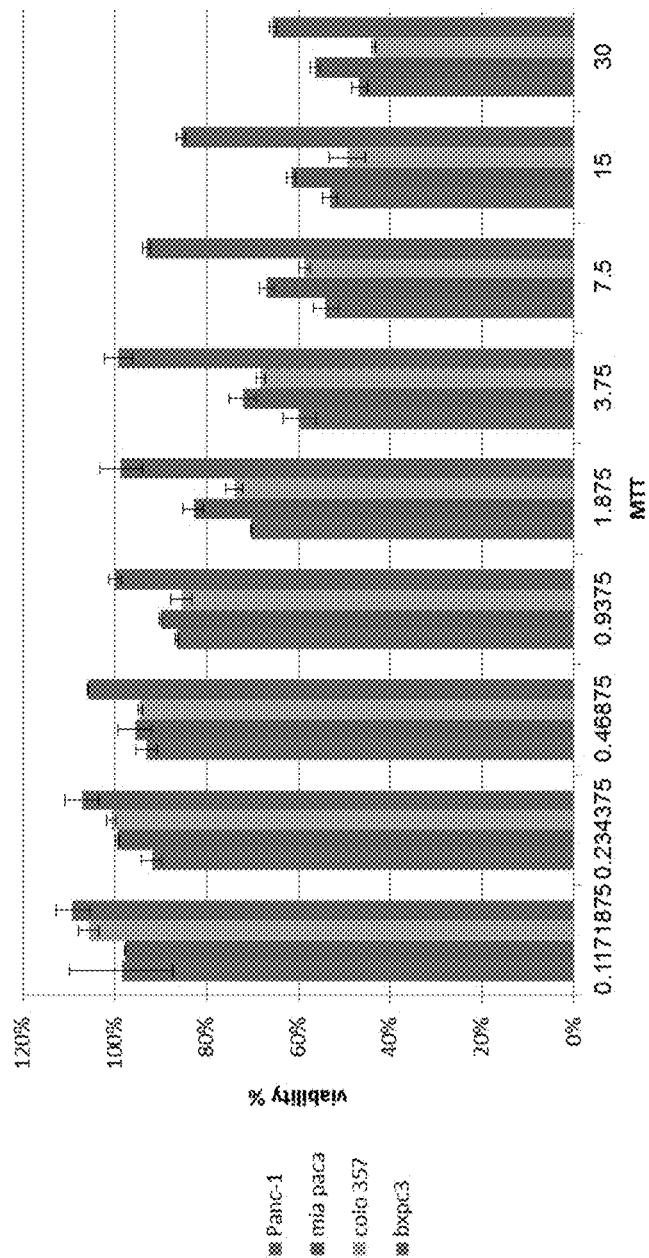

FIG. 17 is a histogram depicting the efficacy of mazF as evaluated in pancreatic cancer cells. PANC1, Mia Paca2, Colo357 (KRAS mutated cells) and BxPC3 (wild type RAS) cell lines were seeded in 96-well plates. After 24 hours, median dilutions of PY4-mazF-mcherry viruses were added. 72 hours later, cell survival was measured the enzymatic MTT assay. Note that the mazF toxin causes to selective eradication of KRAS mutated pancreatic cells. % of cell viability was significantly lower in the three mutated cell lines as compared to the wild type (wt) Kras cells.

DESCRIPTION OF SPECIFIC EMBODIMENTS OF THE INVENTION

The present invention, in some embodiments thereof, relates to nucleic acid constructs and nucleic acid construct systems for treating cancer and, more particularly, but not exclusively, to pharmaceutical compositions and methods using same for treating cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

KRAS mutation is an early event in CRC carcinogenesis. The present inventors have uncovered that the hyperactive RAS pathway can be exploited, rather than inhibited in order to treat cancer. Thus, the present inventors devised a well-regulated toxin anti-toxin (TA) system derived from *E. coli* which enables selective control and efficient killing of tumor cells while sparing normal cells.

As shown in the Examples section which follows, a massive cell death, in a dose-dependent manner, reaching 73% at MOI 10 was seen in mutated KRAS cells as compared to 22% in cells with wild type KRAS (FIG. 6K). Increased expression of MazE (the anti-toxin) protected normal cells from any possible internal or external leakage of the system and confirmed the selectivity, specificity and safety of the targeting system. Considerable tumor shrinkage (61%) was demonstrated in vivo following MazEF-encoding adenovirus treatment without any side effects (FIGS. 8A-C). These results demonstrate a novel, safe and effective gene therapy for treating cancer which exploits the aberrant hyperactive pathway.

According to an aspect of some embodiments of the invention, there is provided a nucleic acid construct comprising:

(i) a first nucleic acid sequence encoding a toxin operatively linked to a first promoter and at least one cancer-associated signaling responsive enhancer element;

(ii) a second nucleic acid sequence encoding an anti-toxin operatively linked to a second promoter, the second promoter being stronger than the first promoter.

According to an aspect of some embodiments of the invention, there is provided a nucleic acid construct system comprising:

(i) a first nucleic acid construct encoding a toxin operatively linked to a first promoter and at least one cancer-associated signaling responsive enhancer element;

(ii) a second nucleic acid construct encoding an anti-toxin operatively linked to a second promoter, the second promoter being stronger than the first promoter.

According to an aspect of some embodiments of the invention, there is provided a nucleic acid construct system comprising:

(i) a first nucleic acid construct encoding a toxin operatively linked to a first promoter and at least one cancer-associated signaling responsive enhancer element;

(ii) a second nucleic acid construct encoding an anti-toxin operatively linked to a second promoter;

wherein the first nucleic acid construct is provided at a higher concentration than the second nucleic acid construct.

As used herein the term "system" refers to at least two distinct nucleic acid construct molecules.

A coding nucleic acid sequence is "operably linked" or "operatively linked" (which is interchangeably used herein) to a regulatory sequence (e.g., promoter) if the regulatory sequence has a transcriptional regulatory effect on the coding sequence linked thereto.

As used herein, the term "promoter" refers to a region of DNA which lies upstream of the transcriptional initiation site of a gene to which RNA polymerase binds to initiate transcription of RNA. The promoter controls where (e.g., in which cells) and/or when (e.g., at which stage or condition in the lifetime of an organism) the gene is expressed.

The promoter can direct transcription of the polynucleotide sequence operably linked thereto in a constitutive or inducible manner.

According to some embodiments of the invention, the promoter is heterologous to the coding sequence operably linked thereto.

As used herein the phrase "heterologous promoter" refers to a promoter from a different gene locus as of the coding sequence operably linked thereto.

According to some embodiments of the invention, the promoter comprises the minimal promoter sequence required for transcription of the coding sequence operably linked to the promoter.

Assays for determining the minimal promoter sequence are known in the art, and described, for example, in Byrne B J., et al., 1983 ["Definition of the simian virus 40 early promoter region and demonstration of a host range bias in the enhancement effect of the simian virus 40 72-base-pair repeat. Proc Natl Acad Sci USA. 80(3): 721-725], which is fully incorporated herein by reference in its entirety.

For example, the minimal SV40 promoter sequence is set forth by SEQ ID NO:40; and the minimal CMV promoter sequence is set forth by SEQ ID NO: 19.

According to some embodiments of the invention, the second promoter is stronger than the first promoter.

It should be noted that promoter activity can be detected and evaluated by various methods, such as by operably linking thereto a coding sequence of a reporter protein which can be detected and quantified in cells transfected with the construct. Examples of such assays include, but are not limited to using the luciferase coding sequence (e.g., SEQ ID NO: 20) under the control of the promoter to be tested, and measuring luciferase activity in the transfected cells (e.g., as described in FIGS. 9B and 13A). Thus, for example, selection of suitable first and second promoters can be performed by comparing the transcription ability of these promoters under identical assay conditions, using for example, the same reporter coding sequence.

According to some embodiments of the invention, the second promoter exhibits at least 10%, 20%, 30%, 40%, 50%, 60%, 70%, 80%, 90%, 100%, 150%, 200%, 300%, 400%, 500%, e.g., at least 1000%, higher transcription ability to transcribe a coding sequence operably linked thereto.

As used herein the phrase "cancer-associated signaling responsive enhancer element" refers to a nucleic acid sequence which serves as an enhancer of transcription by the binding of a specific transcription factor thereto, wherein the specific transcription factor is expressed in cancer cells.

Typically the cancer-associated signaling responsive enhancer element is a cancer-associated proliferative signaling responsive enhancer element.

Known proliferation signaling of cancer cells include the pathways used by several oncogenes. For example, in the RAS pathway the proliferation signaling results in binding of Ets and/or the AP-1 transcription factors to specific Ets and/or Ap-1 binding sites, respectively (which form the PY2 enhancer element). Similarly, in the WNT signaling pathway the proliferation signaling results in binding of the TCF/LEF transcription factors [e.g., TCF7 (TCF-1), TCF7L1 (TCF-3), TCF7L2 (TCF-4) and/or LEF1] to their binding sites (enhancers). Another example includes the MAPK pathway in which the transcription factor MYC (c-myc) can bind to specific binding sites as described elsewhere [Karen I. Zeller, et al., 2006. Global mapping of c-Myc binding sites and target gene networks in human B cells. Proc Natl Acad Sci USA; 103(47): 17834-17839, which is fully incorporated herein by reference].

Similarly, known proliferation signaling of cancer cells include the pathways used by tumor suppressor genes as in the case of retinoblastoma (Rb) tumor suppressor protein. The Rb tumor suppressor protein binds to the E2F1 transcription factor and prevents the interaction between E2F1 and the cell's transcription machinery. In the absence of Rb [e.g., when cyclin-dependent kinases (CDK) and cyclins phosphorylate Rb to pRb], E2F1 (along with its binding partner DPI) mediates the trans-activation of E2F1 target genes that facilitate the G1/S transition and S-phase. E2F targets genes encode proteins involved in DNA replication (for example DNA polymerase, thymidine kinase, dihydrofolate reductase and cdc6), and chromosomal replication (replication origin-binding protein HsOrc1 and MCM5). When cells are not proliferating, E2F DNA binding sites [(e.g., TTTCCCGC (SEQ ID NO:53)] contribute to transcriptional repression.

Thus, according to some embodiments of the invention the cancer-associated signaling responsive enhancer element comprises the E2F DNA binding site(s). In this case, when the nucleic acid construct or system thereof is introduced to cancer cells with a mutation in the Rb tumor suppressor (which prevents binding of Rb to E2F1) the E2F1 transcription factor in the cancer cells can bind to the E2F DNA binding sites (e.g., SEQ ID NO:53), resulting in activation of the promoter operably linked to the toxin coding sequence, and with high expression of the toxin within the cells.

According some embodiments of the invention, the cancer-associated proliferative signaling responsive enhancer element comprises a Ras-responsive element.

According some embodiments of the invention, the Ras comprises K-Ras.

According some embodiments of the invention, the Ras-responsive element comprises the Ets binding site and/or the Ap-1 binding site.

The Ets binding site comprises an ETS domain, which is a winged helix-turn-helix structure that binds to DNA sites with a central GGA(A/T) DNA sequence. The ETS family includes 12 subfamilies as described in Table 1 below.

TABLE 1

| Subfamily | Mammalian family members |
| --- | --- |
| ELF | ELF1, ELF2 (NERF), ELF4 (MEF) |
| ELG | GABPα |
| ERG | ERG, FLI1, FEV |
| ERF | ERF (PE2), ETV3 (PE1) |
| ESE | ELF3 (ESE1/ESX), ELF5 (ESE2), ESE3 (EHF) |
| ETS | ETS1, ETS2 |
| PDEF | SPDEF (PDEF/PSE) |
| PEA3 | ETV4 (PEA3/E1AF), ETV5 (ERM), ETV1 (ER81) |
| ER71 | ETV2 (ER71) |
| SPI | SPI1 (PU.1), SPIB, SPIC |
| TCF | ELK1, ELK4 (SAP1), ELK3 (NET/SAP2) |
| TEL | ETV6 (TEL), ETV7 (TEL2) |

Table 1.

According some embodiments of the invention, the Ets binding site is set forth by SEQ ID NO:1.

According to some embodiments of the invention, the AP-1 binding site is set forth by SEQ ID NO:2.

According to some embodiments of the invention, the Ras-responsive element comprises the PY2 sequence. The PY2 sequence comprises the Ets and Ap-1 binding site and is set forth by SEQ ID NO: 3.

According to some embodiments of the invention, the Ras-responsive element comprises at least two repeats of the PY2 sequence, e.g., at least three repeats of the PY2 sequence, e.g., at least four repeats of the PY2 sequence, e.g., at least five repeats of the PY2 sequence or more.

According to some embodiments of the invention, the Ras-responsive element comprises four repeats of the PY2 sequence (the four repeats of the PY2 sequence are also referred to as "PY4" herein).

As used herein the term "toxin" refers to a polypeptide capable of killing cells.

As used herein the term "anti-toxin" (or "antitoxin") refers to an RNA or a polypeptide capable of neutralizing the effect of the toxin in the cells where the toxin is present and/or active.

There are three known types of toxin—antitoxin systems. Type I toxin-antitoxin systems rely on the base-pairing of complementary antitoxin RNA with the toxin's mRNA. Translation of the mRNA is then inhibited either by degradation via RNase III or by occluding the Shine-Dalgarno sequence or ribosome binding site. Often the toxin and antitoxin are encoded on opposite strands of DNA. Known examples of type I toxin and anti-toxin pairs which can be used in the construct or system(s) of constructs according to some embodiments of the invention include, but are not limited to Hok-Sok [e.g., the Hok protein (SEQ ID NO:47; encoded by SEQ ID NO: 48) and the Sok coding sequence (SEQ ID NO: 49) encoding the SOK protein (SEQ ID NO:50)], fst-RNAII, TisB-IstR, LdrD-Rd1D, FlmA-FlmB, Ibs-Sib, TxpA/BrnT-RatA, SymE-SymR, and XCV2162-ptaRNA1 [reviewed in Sabine Brantl, and Natalie Jahn. sRNAs in bacterial type I and type III toxin-antitoxin systems. FEMS Microbiology Reviews. First published online: 25 Mar. 2015. doi: 10.1093/femsre/fuv003; Vogel J, et al., 2004. "The small RNA IstR inhibits synthesis of an SOS-induced toxic peptide". Curr. Biol. 14 (24): 2271-6; Greenfield T J, et al., 2000. "The antisense RNA of the par locus of pAD1 regulates the expression of a 33-amino-acid toxic peptide by an unusual mechanism". Mol. Microbiol. 37 (3): 652-60; Kawano M, et al., 2002. "Molecular characterization of long direct repeat (LDR) sequences expressing a stable mRNA encoding for a 35-amino-acid cell-killing peptide and a cis-encoded small antisense RNA in Escherichia coli". Mol. Microbiol. 45 (2): 333-49; Loh S M, et al., 1988. "Nucleotide sequence and transcriptional analysis of a third function (Flm) involved in F-plasmid maintenance". Gene 66 (2): 259-68; Fozo E M, et al., 2008. "Repression of small toxic protein synthesis by the Sib and OhsC small RNAs". Mol. Microbiol. 70 (5): 1076-93; Silvaggi J M, et al. 2005. "Small Untranslated RNA Antitoxin in Bacillus subtilis". J. Bacteriol. 187 (19): 6641-50; Gerdes K, et al. 2007. "RNA antitoxins". Curr. Opin. Microbiol. 10 (2): 117-24; Findeiss S, et al. 2010. "A novel family of plasmid-transferred anti-sense ncRNAs". RNA Biol. 7 (2): 120-4; each of which is fully incorporated herein by reference in its entirety].

In Type II toxin-antitoxin systems a labile protein anti-toxin tightly binds and inhibits the activity of a stable toxin. Known examples of type II toxin and anti-toxin pairs which can be used in the construct or system(s) of constructs according to some embodiments of the invention include, but are not limited to, CcdB-CcdA, ParE-ParD, MazF-MazE, yafO-yafN, HicA-HicB, Kid-Kis, and Zeta-Epsilon [reviewed in Bahassi E M, et al., 1999. "Interactions of CcdB with DNA gyrase. Inactivation of Gyra, poisoning of the gyrase-DNA complex, and the antidote action of CcdA.". J Biol Chem 274 (16): 10936-44; Jensen R B, Gerdes K, 1995. "Programmed cell death in bacteria: proteic plasmid stabilization systems.". Mol Microbiol 17 (2): 205-10; Singletary L A, et al. 2009. "An SOS-Regulated Type 2 Toxin-Antitoxin System". J. Bacteriol. 191 (24): 7456-65. doi:10.1128/JB.00963-09. PMC 2786605. PMID 19837801; Jorgensen M G et al. 2009. "HicA of Escherichia coli defines a novel family of translation-independent mRNA interferases in bacteria and archaea.". Journal of Bacteriology 191 (4): 1191-1199; Diago-Navarro E, et al., 2010. "parD toxin-antitoxin system of plasmid R1—basic contributions, biotechnological applications and relationships with closely-related toxin-antitoxin systems". FEBS J. 277 (15): 3097-117; Mutschler H and Meinhart A. 2011. "ε/ζ systems: their role in resistance, virulence, and their potential for antibiotic development.". Journal of Molecular Medicine 89 (2): 1183-1194; each of which is fully incorporated herein by reference in its entirety].

Type III toxin-antitoxin systems rely on direct interaction between a toxic protein and an RNA antitoxin. The toxic effects of the protein are neutralized by the RNA gene. A non-limiting example of type III toxin and anti-toxin pairs which can be used in the construct or system(s) of constructs according to some embodiments of the invention is the ToxIN system from the bacterial plant pathogen Erwinia carotovora. The toxic ToxN protein is approximately 170 amino acids long and has been shown to be toxic to E. coli. The toxic activity of ToxN is inhibited by ToxI RNA, an RNA with 5.5 direct repeats of a 36 nucleotide motif (AGGTGATTTGCTACCTT-TAAGTGCAGCTAGAAATTC, SEQ ID NO:24).

The sequences of the various toxin and anti-toxin agents (e.g., RNA or proteins) are known in the art and can be obtained from various sources including the "National Center for Biotechnology Information" data base [www(dot)ncbi(dot)nlm(dot)nih(dot)gov/].

According some embodiments of the invention, the anti-toxin is a polypeptide capable of neutralizing the effect of the toxin in the cells where the toxin is present and/or active.

According some embodiments of the invention, the anti-toxin comprises an RNA silencing agent.

According some embodiments of the invention, the toxin and the anti-toxin comprise a bacterial-derived toxin anti-toxin system.

MazF is a bacterial ribonuclease (e.g., SEQ ID NOs: 6 and 51), which is specific for ACA sequences in single-stranded RNA. MazF-induced toxicity is executed by blocking de novo protein synthesis through its endoribonuclease activity (mRNA interferases; Inouye et al., 2006). The MazE anti-toxin (e.g., SEQ ID NOs: 13 and 52) interferes with the lethal action of the MazF toxin and neutralizes it s toxicity.

According some embodiments of the invention, the toxin anti-toxin system comprise a MazEF system.

According some embodiments of the invention, the MazF toxin comprises the coding sequence set forth by SEQ ID NO:6.

According some embodiments of the invention, the MazF toxin protein is set forth by SEQ ID NO: 51.

According some embodiments of the invention, the MazE anti-toxin comprises the coding sequence set forth by SEQ ID NO:13.

According some embodiments of the invention, the MazE anti-toxin comprises the amino acid sequence set forth by SEQ ID NO: 52.

According some embodiments of the invention, the second promoter comprises CMV and the first promoter comprises SV40.

According some embodiments of the invention, the second nucleic acid sequence or the second nucleic acid construct further comprises a non-cancerous associated responsive element for regulating transcription of the anti-toxin.

Thus, by inclusion of the additional responsive element for regulating the transcription of the anti-toxin the construct or the construct system ensures that no-cell killing of "normal" (non-cancerous) cells.

For example, as shown in FIGS. 11A and 11B the p53 wild type responsive element (such as provided in SEQ ID NO:14) can be added upstream of the promoter which drives the transcription of the antitoxin coding sequence.

According some embodiments of the invention, the non-cancerous associated responsive element comprises the p53 wild type responsive element.

According some embodiments of the invention, the p53 wild type responsive element is set forth by SEQ ID NO:14.

According some embodiments of the invention, the second nucleic acid sequence or the second nucleic acid construct comprises at least one copy of the p53 wild type responsive element set forth by SEQ ID NO:14.

According some embodiments of the invention, the second nucleic acid sequence or the second nucleic acid construct comprises at least 2 repeats of the non-cancerous associated responsive element, e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 repeats of the non-cancerous associated responsive element.

According some embodiments of the invention, the second nucleic acid sequence or the second nucleic acid construct comprises 17 repeats of the p53 wild type responsive element.

According some embodiments of the invention, the second nucleic acid sequence or the second nucleic acid construct comprises the RCGX17 sequence (17 repeats of the p53 wild type responsive element) as set forth by SEQ ID NO: 15.

For example, as shown in FIG. 12, cancerous cells having a mutation in both ras and p53 (e.g., SHP77 cells which are $Ras^{mut}/p53^{mut}$) were more sensitive to cell killing than cells which exhibit wild type sequences of both ras and p53 (e.g., H1650 cells which are $Ras^{wt}/p53^{wt}$).

Additionally or alternatively, the nucleic acid construct or construct system can include a repressor-operator system for control of expression in cancerous cells having hyperactive cell signaling.

According some embodiments of the invention, the first nucleic acid sequence or the first nucleic acid construct further comprises a repressor of a bacterial repressor-operator system, the repressor being under a transcriptional regulation of the cancer-associated proliferative signaling responsive enhancer element, and wherein the second nucleic acid sequence or construct comprises an operator of the bacterial repressor-operator system, such that expression of the repressor inhibits expression of the antitoxin.

According some embodiments of the invention, the repressor comprises the Tetracycline repressor (Tet-R) sequence, and wherein the operator comprises the tetracycline operator sequence.

According some embodiments of the invention, the operator comprises at least two repeats of the sequence tetracycline operator sequence.

According some embodiments of the invention, the first nucleic acid sequence or the first nucleic acid construct comprises four repeats of the PY2 sequence set forth by SEQ ID NO:2 being upstream and operably linked to the SV40 minimal promoter region set forth by SEQ ID NO:4, a toxin coding sequence being downstream of and transcriptionally regulated by the SV40 minimal promoter region, an IRES sequence set forth by SEQ ID NO:7 being downstream and operably linked to the toxin coding sequence, and a Tetracycline repressor set forth by SEQ ID NO: 8 being downstream of and operably linked to the IRES sequence.

According some embodiments of the invention, the second nucleic acid sequence or the second nucleic acid construct comprises a CMV minimal promoter which comprises two repeats of a tetracycline operator as set forth by SEQ ID NO:9 and an antitoxin coding sequence being downstream of and operably linked to the CMV minimal promoter.

For example, as schematically illustrated in FIG. 2C, in cells with hyperactive RAS, the Tet-R is expressed resulting in its binding to the Tetracycline operator and accordingly inhibition of expression of the antitoxin mazE which is downstream to the Tetracycline operator. In contrast, in cells with wild type RAS the TetR is not overexpressed and accordingly does not bind to the tetracycline operator, resulting in expression of the antitoxin maze (FIG. 2D).

It should be noted that when the nucleic acid construct system is used, the first nucleic acid construct and the second nucleic acid constructs can be co-transfected at any MOI ratio into the cell-of-interest (e.g., the target cell such as the cancerous cell).

According to some embodiments of the invention, the first nucleic acid construct and the second nucleic acid constructs are co-transfected at a 1:1 MOI ratio.

For example, when using a nucleic acid construct system in which the second promoter is stronger than the first promoter, a 1:1 MOI ratio can be used for co-transfection.

Additionally or alternatively, when using a nucleic acid construct system in which the second promoter has a similar ability to direct transcription of a nucleic acid sequence operably linked thereto as the ability of the promoter of the first nucleic acid construct, and/or in the case of using identical promoters in both constructs (e.g., the SV40 promoter as shown in FIG. 11A) then the amount of the first nucleic acid construct should be higher than the amount of the second nucleic acid construct, in order to ensure cell killing.

According to some embodiments of the invention, the first nucleic acid construct and the nucleic acid construct are co-transfected into cells at an MOI ratio of 1 to 0.9, e.g., at an MOI ratio of 1 to 0.8, 1 to 0.7, 1 to 0.6, 1 to 0.5, 1 to 0.4, 1 to 0.3, 1 to 0.2, e.g., 1 to 0.1, respectively.

According to some embodiments of the invention, the first nucleic acid construct and the nucleic acid construct are co-transfected into cells at an MOI ratio of 1 to 0.5, respectively.

The nucleic acid construct of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of toxin or anti-toxin mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the nucleic acid construct of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The nucleic acid construct may or may not include a eukaryotic replicon. If a eukaryotic replicon is present, then the nucleic acid construct is amplifiable in eukaryotic cells using the appropriate selectable marker. If the nucleic acid construct does not comprise a eukaryotic replicon, no episomal amplification is possible. Instead, the recombinant DNA integrates into the genome of the engineered cell, where the promoter directs expression of the desired nucleic acid.

The nucleic acid construct of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a toxin or anti-toxin can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A⁺, pMT010/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of toxin-anti-toxin protein since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the nucleic acid construct of some embodiments of the invention can also include sequences engineered to enhance stability, production, purification, yield or toxicity of the expressed peptide. For example, the expression of a fusion protein or a cleavable fusion protein comprising the toxin or anti-toxin protein of some embodiments of the invention and a heterologous protein can be engineered.

According some embodiments of the invention, the nucleic acid construct or the nucleic acid construct system is adeno-virus based.

As used herein the term "adeno-virus" encompasses adenoviruses and adeno-associated virus(es) (AAVs).

Adenoviruses (members of the family Adenoviridae and genus *Mastadenovirus*.) are medium-sized (90-100 nm), nonenveloped (without an outer lipid bilayer) viruses with an icosahedral nucleocapsid at 70-90 nm in diameter and each contains a single linear, double-stranded DNA genome of approximately 36 kb. Within the almost 100 different serotypes of human adenovirus, 51 are known to be pathogenic in humans and to cause a wide range of illnesses, from mild respiratory infections in young children (known as the common cold) to life-threatening multi-organ disease in people with a weakened immune system.

Adeno-associated virus (AAV) is a small virus which infects humans and some other primate species. AAV belongs to the genus Dependoparvovirus, which in turn belongs to the family Parvoviridae. The virus is a small (20 nm) replication-defective, nonenveloped virus. AAV is not currently known to cause disease. The virus causes a very mild immune response, lending further support to its apparent lack of pathogenicity. Gene therapy vectors using AAV can infect both dividing and quiescent cells and persist in an extrachromosomal state without integrating into the genome of the host cell, although in the native virus some integration of virally carried genes into the host genome does occur. These features make AAV a very attractive candidate for creating viral vectors for gene therapy, and for the creation of isogenic human disease models. Recent human clinical trials using AAV for gene therapy in the retina have shown promise [Maguire A M, et al. (2008). "Safety and Efficacy of Gene Transfer for Leber's Congenital Amaurosis". New England Journal of Medicine 358 (21): 2240-8].

There are about 11 AAV serotypes described, all of them can infect cells from multiple diverse tissue types. Tissue specificity is determined by the capsid serotype and pseudo-typing of AAV vectors to alter their tropism range will likely be important to their use in therapy.

As shown in FIG. 10, the present inventors showed that AAV serotype 6 is suitable for expression of the toxin and anti-toxin proteins using the constructs of the nucleic acid construct system of some embodiments of the invention.

According some embodiments of the invention, the nucleic acid construct or the nucleic acid construct system is Lenti-virus based.

Lentivirus is a genus of viruses of the Retroviridae family, characterized by a long incubation period. Lentiviruses can deliver a significant amount of viral RNA into the DNA of the host cell and have the unique ability among retroviruses of being able to infect non-dividing cells, so they are one of the most efficient methods of a gene delivery vector.

The nucleic acid construct or the nucleic acid construct system of some embodiments of the invention can be administered to an organism per se, or in a pharmaceutical composition where it is mixed with suitable carriers or excipients.

According to an aspect of some embodiments of the invention, there is provided a pharmaceutical composition comprising the nucleic acid construct of some embodiments of the invention or the nucleic acid construct system of some embodiments of the invention and a pharmaceutically acceptable carrier or diluents.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the nucleic acid construct of some embodiments of the invention or the nucleic acid construct system of some embodiments of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (the nucleic acid construct of some embodiments of the invention or the nucleic acid construct system of some embodiments of the invention) effective to prevent, alleviate or ameliorate symptoms of a disorder (e.g., cancer, e.g., colon cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to an aspect of some embodiments of the invention there is provided a method of treating cancer comprising, the method comprising introducing into the cancer cells the nucleic acid construct of some embodiments of the invention, or the nucleic acid construct system of some embodiments of the invention, wherein the cancer cells are characterized by hyper activity of the proliferative signaling as compared to non-cancerous cells of the same tissue, thereby treating the cancer.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

Thus, the nucleic acid construct of some embodiments of the invention, or the nucleic acid construct system of some embodiments of the invention is administered to the cancer cells of a subject in need thereof.

As used herein, the term "subject" includes mammals, preferably human beings at any age which suffer from the pathology.

According to an aspect of some embodiments of the invention there is provided a composition comprising the nucleic acid construct of some embodiments of the invention, or the nucleic acid construct system of any one of some embodiments of the invention for use in treating cancer, wherein cells of the cancer are characterized by hyper activity of the proliferative signaling as compared to non-cancerous cells of the same tissue.

According to some embodiments of the invention, the cancer comprises a solid tumor.

According to some embodiments of the invention, the cancer comprises cancer metastases and/or cancer micrometastases.

According to some embodiments of the invention, the cancer comprises cancer micrometastases.

Non-limiting examples of the cancer which can be treated by the composition (e.g., the nucleic acid construct or the nucleic acid construct system) or the method of some embodiments of the invention include any solid or non-solid cancer and/or cancer metastasis, including, but is not limiting to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to some embodiments of the invention, the cancer comprises colon cancer.

According to some embodiments of the invention, the cancer comprises lung cancer.

According to some embodiments of the invention, the cancer comprises pancreatic cancer.

According to some embodiments of the invention, the cancer comprises gastric cancer.

According to some embodiments of the invention, the cancer is characterized by a hyperactive RAS GTPase activity.

It should be noted that in cells where the RAS is hyperactive the hydrolysis of GTP (Guanosine-5'-triphosphate) to GDP (Guanosine diphosphate) is prevented, thus the ras pathway is always on (active) and is not deactivated, since it binds to GTP.

According to some embodiments of the invention, the RAS is a KRAS protein and wherein the hyperactive KRAS is caused by a G13D mutation in the KRAS protein set forth by SEQ ID NO:16 (i.e., substitution of glycine with aspartic acid at amino acid position 13 in the KRAS protein set forth by SEQ ID NO:16).

According to some embodiments of the invention, the RAS is an NRAS protein and wherein the hyperactive NRAS is caused by a Q61K mutation in the NRAS protein set forth by SEQ ID NO:17 (i.e., substitution of Glutamine with Lysine at amino acid position 61 in the NRAS protein set forth by SEQ ID NO:17).

According to some embodiments of the invention, the RAS is a HRAS protein and wherein the hyperactive HRAS is caused by a G12V mutation in the HRAS protein set forth by SEQ ID NO:18 (i.e., substitution of Glycine with Valine at amino acid position 12 of the HRAS protein set forth by SEQ ID NO:18).

According to some embodiments of the invention, the active agents described hereinabove (e.g., the nucleic acid construct of some embodiments of the invention and/or the nucleic acid construct system of some embodiments of the invention) can be provided to the subject in need thereof along with an additional medicament identified for treating the cancer, i.e., by combination therapy.

Therapeutic regimen for treatment of cancer suitable for combination with the nucleic acid construct of some embodiments of the invention and/or the nucleic acid construct system of some embodiments of the invention include, but are not limited to chemotherapy, biological therapy, immunological therapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy.

According to some embodiments of the invention, the method further comprising treating a subject having the cancer by a treatment selected from the group consisting of: chemotherapy, biological therapy, radiotherapy, phototherapy, photodynamic therapy, surgery, nutritional therapy, ablative therapy, combined radiotherapy and chemotherapy, brachiotherapy, proton beam therapy, immunotherapy, cellular therapy and photon beam radiosurgical therapy.

According to some embodiments of the invention, the composition further comprises an agent suitable for a treatment selected from the group consisting of: chemotherapy, biological therapy, photodynamic therapy, nutritional therapy, brachiotherapy, immunotherapy, and cellular therapy.

It should be noted that such synergistic activity of treatment with the nucleic acid construct of some embodiments of the invention and/or the nucleic acid construct system of some embodiments of the invention treatment with additional therapeutic methods or compositions has the potential to significantly reduce the effective clinical doses of such treatments, thereby reducing the often devastating negative side effects and high cost of the treatment.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclopho sphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Approved chemotherapy include, but are not limited to, abarelix, aldesleukin, aldesleukin, alemtuzumab, alitretinoin, allopurinol, altretamine, amifostine, anastrozole, arsenic trioxide, asparaginase, azacitidine, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trastuzumab, tretinoin ATRA, Uracil Mustard, valrubicin, vinblastine, vinorelbine, zoledronate and zoledronic acid.

Anti-cancer biological drugs that can be co-administered with the compounds of the invention include, but are not limited to bevacizumab (AVASTIN™ Genentech Inc.), Cetuximab (ERBITUX™ ImClone Systems Incorporated), Panitumumab (VECTIBIX™ Immunex Corporation) and/or any combination thereof.

Additional anti-cancer drugs that can be co-administered with the compounds of the invention include, but are not limited to 5-FU, Capecitabine (XELODA™ Hoffmann-La Roche, Inc), Irinotecan (CAMPTOSAR™ YAKULT HONSHA COMPANY, LTD), Oxaliplatin (ELOXATIN™ Sanofi), Trifluridine and tipiracil (LONSURF™ TAIHO PHARMACEUTICAL CO., LTD.), Gemcitabine (GEMZAR™ Eli Lilly and Company), Albumin-bound paclitaxel (ABRAXANE™ of ABRAXIS BIOSCIENCE, LLC), Cisplatin, Paclitaxel (TAXOL™ Bristol-Myers Squibb Company), Docetaxel (TAXOTERE™ AVENTIS PHARMA S.A.), Irinotecan liposome (ONIVYDE™ Merrimack Pharmaceuticals, Inc.), dacarbazine (DTIC-DOME™ BAYER HEALTHCARE PHARMACEUTICALS INC.), ETOPOSIDE (ETOPOPHOS™ Bristol-Myers Squibb Company), Temozolomide (TEMODAL™ Schering Corporation), lapatinib (Tyverb™ GlaxoSmithKline), erlotinib (Tarceva™ Astellas Pharma Inc.), everolimus (AFINITOR™ Novartis AG), and/or any combination thereof. It should be noted that any combination of known anti0cancer treatment (e.g., biological, immunological, chemotherapy and the like) can be combined with the gene therapy approach of the claimed compositions As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO:6 is expressed in a DNA sequence format (e.g., reciting T for thymine), but it can refer to either a DNA sequence that corresponds to an E. coli MazF ribonuclease nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074;

4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Reagents—All reagents were purchased from Sigma, Israel unless otherwise stated. All secondary HRP-conjugated antibodies were from Jackson ImmunoResearch Laboratories, USA. ECL reagent, cell culture media and additives were from Beit-Haemek, Israel. Nitrocellulose filters were from Schleicher & Schuell BioScience, USA. Annexin V and Reddot2 dye were purchased from Biotium, and G418 was purchased from Gibco. All plasmid and DNA fragment purifications were carried out with a High-Speed Plasmid Mini Kit and a Zymoclean™ Gel/PCR DNA recovery Kit (Fermentas and Zemo Research, respectively) unless otherwise specified. T4 DNA ligase and restriction enzymes were purchased from New England Biolabs, USA. DNA ligations were carried out overnight at 16° C.

Bacterial Strains—

The following *Escherichia coli* (*E. coli*) strains were used: DH5a (Stratagene, USA) for plasmid propagation and BJ5183 (Stratagene, USA) for the generation of recombinant adenovirus plasmid DNA.

Cell Lines—

HT29 human colon adenocarcinoma, HCT116 human colon cancer, R1 KRAS transformed rat enterocytes and HEK293 human kidney cell lines were grown in high-glucose Dulbecco's modified Eagle's medium (DMEM), all supplemented with 5% heat-inactivated fetal bovine serum (FBS), 1% penicillin and streptomycin in an atmosphere of 95% oxygen and 5% $CO_2$. 1 µg/ml tetracycline was added to the HEK293 medium for TA virus production. In addition, 600 µg/ml G418 was added to the culture medium of MazE-expressing cells.

Oligonucleotides—

All the oligonucleotides that were used in this study were purchased from Sigma, Israel.

Recombinant DNA techniques were carried out according to standard protocols or as recommended by the manufacturers. A more detailed description of the procedure is provided hereinbelow.

Construction and Propagation of Recombinant Adenovirus Vectors

Construction of the Vector Encoding for "mCherry-MazF"—

The monomeric red fluorescence protein mCherry was amplified from an expression cassette by PCR. The PCR product was digested with HindIII and XbaI and cloned between the corresponding sites of the plasmid "pGL3 promoter-Py4-PUMA" (replacing the PUMA gene) that had been previously prepared, generating the "pGL13 promoter-Py4-mCherry" plasmid.

The MazF coding sequence which was amplified from an expression cassette (kindly provided by Dr. Assaf Shapira, Department of Molecular Microbiology and Biotechnology, Tel-Aviv University, Israel) using the primes Hind-Cher-For and Xba-Maz-Rev [5'-CTTTTGCAAAAAGCTTCCAC-CATGggaattcacGTGAGCAAGGGCGAGGAGG-3' (SEQ ID NO:21) and 5'-CCGCCCCGACTCTAGActaaccggtgc-caatcagtacgttaattttggc-3' (SEQ ID NO:22), respectively] and was fused to the C terminus of the mCherry under the RRE, Py4-SV40 mP, generating the "pGL3 promoter-Py4-mCherry-MazF" plasmid. This intermediate vector was used as the template for the amplification of the Py4-mCherry-MazF fusion genes, and the amplified product was cloned using the AdEasy system (pShuttle and pAdEasy-1), as previously described (He et al., 1998, Luo et al., 2007) to generate the regulated expression cassette "pAdEasy-Py4-mCherry-MazF".

Construction of the Vector Encoding for "mCherry"—

The sequence of the red fluorescent protein mCherry3 was amplified by PCR from an expression cassette and cloned downstream to a CMV promoter, generating the expression cassette "pAdEasy-CMV-mCherry".

Construction of the Vector Encoding for "MazEF"—

The tetracycline repressor coding sequence was located downstream to an IRES sequence and cloned downstream to the SV40-mCherry-MazF sequence. An additional arm was introduced to this cassette, controlled by a different minimal promoter (mP) without the RAS-responsive elements. Starting from its N terminus, this arm includes: a CMV mP, a tetracycline operator sequence, the full MazE coding sequence, IRES and EGFP coding sequence (FIG. 2,A), generating the expression cassette "pAdEasy-Py4-mCherry-MazF-IRES-TetR-CMVmp-MazE-IRES-EGFP".

Plasmids were isolated by a standard miniprep procedure and sequenced to confirm their predicted composition. For the production of virus particles, the plasmids "pAdEasy-Py4-mCherry-MazF", "pAdEasy-Py4-mCherry-MazF-IRES-TetR-CMVmp-MazE-IRES-EGFP", "pAdEasy-SV40-mCherry-MazF-IRES-TetR-CMVmp-MazE-IRES-EGFP" and "pAdEasy-mCherry" were isolated from selected "positive" clones and digested with PacI. Next, DNA was purified using a Zymoclean™ Gel DNA Recovery Kit according to the manufacturer's instructions. Five micrograms (µg) of the purified, digested plasmids were used to transfect 70% confluence HEK293 cells (supplemented with tetracycline at a final concentration of 1 µg/ml when the TA construct had been transfected) and HEK293-MazE cells (for the mCherry-MazF construct, supplement S2) in 60-mm culture plates using the calcium-phosphate method. After 24 hours, the transfection medium was replaced with 5 ml of fresh medium (that was supplemented with 1 µg/ml of tetracycline in the TA system). From 7 to 10 days post-transfection, when a cytopathic effect (CPE) had been clearly observed, the cells were collected by scraping them off the plate and pelleting them along with any floating cells in the culture. The pellet was washed once with phosphate-buffered saline (PBS), suspended in 0.5 ml PBS and subjected to 4 cycles of freeze/thaw. Cell debris was precipitated by brief centrifugation, and 300 µl of the supernatant that contained virus particles were used to infect 70% confluent HEK293 and its derivative cells in 10 cm plates (first amplification "cycle"). When one-third to one-half of the cells had been detached (usually after 3-5 days), virus particles were released by freeze/thaw cycles as described above. The supernatant containing viruses was kept at −80° C.

High scale production of the adenoviruses was performed by SIRION biotech, Germany.

Establishment of New Packaging Cell Line for the Production of the Toxin—

The lethal transgene MazF coding sequence was fused to the mCherry gene and cloned into the Ad5 adenoviral vector plasmid DNA. The propagation of the virus particles in the HEK293 packaging cells resulted in low yields of virus production due to the highly toxic nature of the selected gene. Hence, an innovative packaging system was established, based on MazF-resistant HEK293 cells that constitutively express the MazE antitoxin, encoded from the pIRES2-MazE-IRES-EGFP plasmid. The EGFP marker was used for effective and rapid screening of stable clones according to their high fluorescence intensity. The yield was higher by almost 2 orders of magnitude after propagation in MazF-resistant cells compared to propagation in parental HEK293 packaging cells.

Cell-Viability Assay—

The cell-killing activities of adenoviruses encoding for MazF, and MazEF were measured by the Thiazolyl Blue Tetrazoliam Bromide (MTT) enzymatic assay. Briefly, $1\times10^4$ cells were seeded in 96-well plates. After 24 hours, different dilutions of recombinant adenoviruses encoding for the above-described cassettes were added. At 72 hours post infection, the media was replaced by fresh media (100 μl per well) containing 1 mg/ml MTT and the cells were incubated for 2-4 more hours. MTT-formazan crystals were dissolved by the addition of extraction solution (0.1N HCl in absolute isopropanol). Absorbance at 570 nm and a reference wavelength of 690 nm was recorded on an automated microplate reader.

Detection of Cell Death

Apoptosis—

Cells were seeded in 12-well plates ($1\times10^5$ cells/well) in complete medium and infected with the different adenoviruses at several multiple of infection (MOI) for 72 hours. Annexin V (Annexin V, CF640R conjugate) was detected according to the manufacturer's protocol (Biotium Inc., USA). The cells were washed with PBS and then incubated in a solution of Annexin V binding protein. The cells were analyzed by flow cytometry [FACSCalibur (Becton Dickinson, CA)], and the results were analyzed with the CELL-Quest program (Becton Dickinson).

Total Dead Cells—

Cells were seeded in 12-well plates ($1\times10^5$ cells/well) in complete medium and infected with the different adenoviruses at several MOI for 72 hours. Dead cells were detected by RedDotTM2, a far-red cell membrane-impermeable nuclear dye, according to the manufacturer's protocol (Biotium Inc., USA). The cells were washed with PBS, and then incubated in a solution of RedDot2 dye. Far red nuclear staining was detected by flow cytometry.

End-Point Dilution Assay (EPDA)—

$1\times10^4$ HEK293 cells/well were seeded in 96-well plate in 100 μl of growth medium. The recombinant adenovirus stock solutions were serially diluted 10-fold to a concentration in a range of $10^{-3}$-$10^{-10}$ into growth medium and added to each well in columns 1-10. Virus-free growth medium was added to the wells in columns 11 and 12 which served as controls for the viability of non-infected cells. The plate was incubated in a humidified $CO_2$ (5%) incubator for 10 days at 37° C. Each well was checked for CPE using a microscope. A well was scored as CPE positive even if only a few cells showed cytopathic effects. The viral titer was calculated according to the formula: Titer (pfu/ml)=$10^{(x+0.8)}$, where x=the sum of the fractions of CPE-positive wells for each dilution (10 out of 10 wells with CPE calculated as "1").

Colony Formation Assay—

$5\times10^5$ HCT116 and HT29 cells were seeded per well in 6-well plates. After 24 hours, the cells were infected with 25 and 10 MOI of the viruses "pAdEasy-Py4-mCherry-MazF-IRES-TetR-CMVmp-MazE-IRES-EGFP" and "pAdEasy-SV40-mCherry-MazF-IRES-TetR-CMVmp-MazE-IRES-EGFP" or left un-infected. After 7 hours, the cells were trypsinized and seeded in 3-fold dilutions and incubated for 7 days. Surviving colonies were fixed with 4% formaldehyde in PBS and stained with 0.02% crystal violet.

Xenograft Model in Mice for Measuring In Vivo Tumor Development—

Male 6-8 week old athymic nude mice (Harlan Laboratories) (n=18) were housed in sterile cages and handled with aseptic precautions. The mice were fed ad libitum. For testing the therapeutic potential of the TA system, exponentially growing HCT116 cells were harvested and resuspended at a final concentration of $5\times10^6$ cells per 0.1 ml PBS per injection. The cells were injected subcutaneously at two sites on the backs of the mice. When tumors were palpable (~0.3-0.5 $cm^3$), the mice were randomly divided into three groups of six each and the treatment was started. The viruses Ad-Py4-TA (6 mice) and ΔPy4-TA $1\times10^9$ pfu (6 mice) or PBS (6 mice) were administrated via two intraperitoneal injections with a 3-day interval between injections. The mice were weighed, the tumor volume was measured with a caliper every two days starting from treatment onset and those results were carefully plotted. Tumor volume was calculated as $4/3\pi\cdot a\cdot b^2$. At the end of the experiment, MazF and MazE expression in the tumors was monitored by imaging using the CRi Maestro system. The mice were anesthetized and then sacrificed by cervical dislocation and the tumors were excised.

TABLE 2

RT-PCR primers

| Gene | Forward primer (5'-3') | SEQ ID NO: | Reverse primer (5'-3') | SEQ ID NO: |
|---|---|---|---|---|
| P53 | CCCAAGCAATGGATGATTTGA | 25 | GGCATTCTGGGAGCTTCATCT | 36 |
| P21 | GGCAGACCAGCATGACAGATT | 26 | GCGGATTAGGGCTTCCTCTT | 37 |
| Bax | TGAGCAGATCATGAAGACAGGG | 27 | GCTCGATCCTGGATGAAACC | 38 |
| Noxa | AGAGCTGGAAGTCGAGTGT | 28 | GCACCTTCACATTCCTCTC | 39 |
| Puma | TCAACGCACAGTACGAGCG | 29 | GTAAGGGCAGGAGTCCCATG | 40 |
| MDM2 | CAGGCAAATGTGCAATACCAA | 30 | GGTTACAGCACCATCAGTAGGTACAG | 41 |
| 14-3-3 | GCCTATAAGAACGTGGTGGGC | 31 | CCTCGTTGCTTTTCTGCTCAA | 42 |
| CD95 | CCCTCCTACCTCTGGTTCTTACG | 32 | TTGAATGTCAGTCACTTGGGCAT | 43 |

TABLE 2-continued

RT-PCR primers

| Gene | Forward primer (5'-3') | SEQ ID NO: | Reverse primer (5'-3') | SEQ ID NO: |
|---|---|---|---|---|
| Btg2 | CCAGGAGGCACTCACAGAGC | 33 | GCCCTTGGACGGCTTTTC | 44 |
| GADD45 | CTCAACGTCGACCCCGATAA | 34 | ACATCTCTGTCGTCGTCCTCG | 45 |
| Survivin | CCACCGCATCTCTACATTCA | 35 | CAAGTCTGGCTCGTTCTCAGT | 46 |

Statistics—

Data from the in vitro studies are presented as mean±SD (standard deviation) of sets of data as determined in triplicates. Statistical significance between treatments was determined by Student t-test, P values <0.05 were considered significant.

In the in vivo studies, the tumor-bearing mice were randomized into various treatment groups (n=6) and the tumor volumes were periodically monitored and calculated as $4/3\pi \cdot a \cdot b^2$. Statistical significant differences between groups and at different time points were determined by Student t-test.

Study Approval—

The study was approved by the Institutional committee for animal welfare at Tel-Aviv Sourasky Medical Center.

Example 1

Experimental Results

The Activity of the PY4 Ras-Responsive Element was Tested in HCT116 Cells—

The activity of the KRAS pathway was evaluated in mutated CRC cells (HCT116). HCT116 cells were transfected with the luciferase vector (and Renilla plasmid) in which luciferase expression is under the control of the SV40 promoter and the PY4 enhancer (the luciferase construct is depicted in FIG. 9B). HCT116 CRC cell line is highly responsive to the Ras-activated promoter containing the Py2 Repeats (PY4). The Luciferase activity was normalized to Renilla Luciferase activity from a parallel co-transfection (FIG. 1I). As shown in FIG. 1I, the luciferase activity was significantly higher in the transfected cells compared to the untransfected cells.

Eradication of mutated RAS-Harboring Cells by Adenovirus-Mediated Delivery of MazF Ribonuclease—

The potency and ability of MazF to kill the target cells were evaluated prior to engineering a more complex system with several toxicity control points. Massive cell death, in a dose-dependent manner, was induced following infection of HCT116 cells [containing a mutated KRAS at codon 13 (Gly to Asp)] with Ad-Py4-SV40-mCherry-MazF (FIG. 1A). FIGS. 1A-H show the cytotoxicity induced by the ribonuclease activity qualitatively evaluated by a fluorescent microscope examination 72 hours after the infection (FIGS. 1D-E) as compared to the uninfected cells (FIGS. 1B-C). About 35% cell survival (relative to the uninfected controls) was quantitatively measured by the enzymatic MTT assay upon treatment, when employing a MOI of 25 (FIG. 1F). Cytotoxic activity of MazF was confirmed by FACS analysis: 50% apoptosis was measured using annexin V (FIG. 1G), while about 80% membrane compromised or dead cells was detected with RedDot2 (FIG. 1H).

Example 2

Design of a Toxin-Antitoxin Cassette Utilizing Hyperactive Ras in Cancer Cells

Rational Design of an Innovative Toxin-Antitoxin Cassette for Enhanced Regulation—

The rationale behind the design of the "pAdEasy-Py4-SV40Mp-mCherry-MazF-IRES-TetR-CMVmp-MazE-IRES-EGFP" construct (FIG. 2A), or briefly "pAdEasy-Py4-TA", was to couple the ribonuclease activity with its antidote in order to enable protection of non-target cells (i.e., normal cells without a hyperactive RAS pathway) while allowing a high level of expression of the toxic agent in mutated RAS-harboring cells.

In hyperactive RAS cells (FIG. 2C), the Py4 enhancer element induced toxin expression significantly more than that of the antitoxin. The Tet repressor, which is also expressed in high levels, binds to the Tet operator sequence and further inhibits the transcription of the antitoxin. Altogether, MazF is expected to overcome the antitoxin inhibition and the cells should die.

In cells that do not harbor mutated RAS (FIG. 2D), the Py4 enhancer is not activated, therefore there is no preference for expression from the SV40 mP. Since the CMV mP is slightly stronger than the SV40 mP and one molecule of the AT inhibits two molecules of toxin, the inhibitory activity of the antitoxin should prevail.

Consequently, the MazE in these cells will overcome the toxicity of MazF and the cells will survive. FIG. 2E shows a representative Western blot that confirms the differences in the degree of expression of the toxin (represented by the mCherry) vs. antitoxin (represented by the GFP). In cells with mutated KRAS, the expression of the toxin is higher than the antitoxin upon infection with the PY4-TA viruses.

Example 3

MazE Protects Normal Cells from MazF Cytotoxic Activity

MazE Protects Normal Cells from MazF Cytotoxic Activity

Experimental Results

In order to demonstrate the advantage of using the pAdEasy-Py4-TA cassette, the present inventors tested its ability to protect cells with wild type (WT) RAS from possible "leakage" of the lethal gene. The basal expression from the SV40 mP along with low expression levels of RAS in normal cells induce low expression of MazF. However, even this low level of expression is sufficient to kill a cell. HT29 cells, with WT RAS, were infected with twofold dilutions of the MazEF- or MazF-encoding viruses, and the viability of the cells was qualitatively examined by light and fluorescence microscopy. As shown in FIGS. 3C, 3E, 3G, 3I, and 3K, infection with MazF decreased cell viability, indicating a leakiness of MazF expression even in the absence of mutated RAS. In contrast, infection with the MazEF construct was well tolerated. When visualized under a fluorescence microscope, the intoxicated Ad-Py4-SV40-mCherry-MazF-infected cells showed very faint red fluorescence, indicating inefficient mCherry-MazF accumulation. This is due to the ribonuclease activity of MazF that results in inhibition of protein synthesis, including its own (Zhang 2003; Shapira et al., 2012). On the other hand, the ribonuclease activity of MazF was neutralized by its antidote MazE in cells infected with pAdEasy-Py4-TA, as indicated by the presence of both red and green fluorescence (FIGS. 3B, 3D, 3F, 3H and 3J).

Example 4

The MazEF Cassette is Capable of Killing Cells Harboring Hyperactive Ras

Experimental Results

Adenovirus-Mediated Delivery of TA-Encoding Cassette Specifically Eliminates R1 Cells Harboring Activated Ras—

The potential of the MazEF-encoding cassette to kill target cells was tested in a proof of concept study performed in R1 cells, which serve as a model system for hyperactive RAS-harboring cells (Arber et al., 1996). R1 cells were infected with twofold dilutions of the mCherry encoding virus (the mCherry construct is schematically depicted in FIG. 4A) or of the PY4-TA (MazEF-encoding) virus (FIG. 2A). Infection of R1 cells with MazEF elicited a considerable cytotoxic effect, decreasing viability to 36% (at MOI 5) relative to the uninfected controls, while no significant effect was seen after infection with the mCherry cassette (80-90%) (shown qualitatively by light microscope in FIGS. 4B-D and quantitatively by MTT in FIG. 4E). The expression of the GFP and mCherry proteins indicates that both MazF and MazE components had been expressed (FIGS. 4F-G). However, although both, mazF and mazE were expressed, the mazF overcame the inhibition of the antitoxin in KRAS mutated cells;

The MazEF Cassette Kills Mutated Ras-Harboring Cells—

An in vitro colony-forming assay was performed to qualitatively and comparatively assess the sensitivity of CRC cells with mutated RAS to the expression of the transgene. In addition, this assay was intended to verify that MazF is well tolerated by the normal cells that do not harbor hyperactive RAS. HCT116 (harboring hyperactive RAS) and HT29 (no KRAS mutation) cells were infected with 25 and 10 MOI of "pAdEasy-Py4-TA", "pAdEasy-ΔPy4-TA" or left uninfected. The cells were trypsinized and seeded in 3-fold dilutions 7 hours later. Surviving colonies were stained after 7 days. FIGS. 5A-J show the potency of the expressed transgene under the control of the RRE (FIG. 5B) compared to uninfected cells (FIG. 5A) and to the control cassette carrying a deletion of the RRE (FIG. 5D). Prominent differences in the numbers of surviving colonies were observed, confirming that MazF indeed overcame the inhibitory effect of MazE in mutated RAS-harboring cells (FIG. 5B) while MazE was able to protect cells (with the wild type RAS, devoid of the RA hyperactive mutation) from MazF toxicity (FIG. 5G). In addition, the selectivity of this targeting system was confirmed since the massive cell death took place only in the RRE—including cassette (FIG. 5B), while no significant effect was seen after infection with the ΔPy4-TA cassette that lacks the RRE (FIG. 5D).

Deletion of the RAS-Responsive Element Decreases the Cytotoxic Activity of MazF—

As mentioned above, an additional cassette lacking the RRE, "pAdEasy-ΔPy4-TA", was also constructed (FIG. 2B). FIGS. 7A-C demonstrate that deletion of the RAS-responsive DNA element enhanced the contribution of MazE. Cell viability was measured by FACS analysis: while massive cell death (55% apoptosis, 82% dead cells) was observed following infection with the full toxin-antitoxin encoding viruses, deletion of the RAS-responsive DNA element dramatically reduced this effect to 18% and 10%, respectively (FIGS. 7A-B; the untreated cells are shown in red, the toxin antitoxin-treated cells are shown in black, and the cells that were treated with the RRE deletion cassette are shown in green). These results were also confirmed by the enzymatic MTT assay (FIG. 7C), where a difference of about 60% was observed between Py4-TA and ΔPy4-TA.

Adenovirus-Mediated Delivery of TA Encoding Cassette Specifically Eliminates Activated Ras-Harboring CRC Cells—

The present inventors further examined the ability of the above-described TA system to kill a human cancer cell line expressing hyperactive RAS. HCT116 and HT29 cells were infected with twofold dilutions of the MazEF-encoding viruses, starting from 10 MOI (FIGS. 6E-J), or left untreated (FIGS. 6A-D). Massive cell death (73%, relative to the uninfected control, at 10 MOI) was demonstrated exclusively in the mutated KRAS harboring cells (HCT116) but not in cells lacking hyperactive RAS (HT29 cells), emphasizing the potency of this system (FIG. 6K). The percentage and intensity of the fluorescence of green cells (FIG. 6J) was higher than that of the red ones (FIG. 6I) in HT29 cells, lacking hyperactive RAS. This indicates that the expression of the antitoxin increases and exceeds that of the toxin in cells devoid of the hyperactive RAS.

In order to confirm and further support the ability of this system to protect normal cells on one hand, and to efficiently kill cancer cells on the other hand, additional CRC cell lines were tested and yielded very similar results, substantiating the above observations (data not shown). The potency of this system was also tested for other cancer types, such as pancreatic and prostate, suggesting a wide range of therapeutic potential of this suggested treatment modality (data not shown).

Induction by Tetracycline Results Increased Expression of the Antitoxin MazE in Naïve Cells—

Inclusion of tetracycline provided an additional protective layer, not only for virus production and propagation but also for normal cell protection. Binding of tetracycline to the Tet repressor led to a conformation change that resulted in relief of the MazE transcriptional inhibition. Consequently, expression of the antitoxin was increased in nave cells, as demonstrated by the increase in green fluorescence (FIGS. 6N and 6O), while tetracycline did not compromise the toxicity of MazF in mutated RAS-harboring cells (FIG. 6P). It is noted that in cells with mutated RAS with or without the addition of tetracycline, the viability of the cells was the same.

Example 5

MazEF-Encoding Viruses Inhibit Tumor Growth In Vivo

Experimental Results

MazEF-Encoding Viruses Inhibit Tumor Growth In Vivo—

The therapeutic potential of the TA system was tested by specific targeting of tumor cells in nude mice bearing a xenograft of HCT116 CRC cells, harboring mutated RAS. The growth of these cells was markedly inhibited by Py4-TA-encoding viruses (FIG. 8A). Impressive tumor shrinkage was demonstrated in vivo following treatment with Ad-Py4-SV40-MazEF-encoding adenovirus (61%) (P<0.0002) without any toxic or side effects. In the Ad-ΔPy4-SV40-MazEF treated mice (control group) tumor volume was reduced by only 27% (P<0.4). No growth inhibition was seen following injection of PBS (FIG. 8A).

Throughout this study the mice were monitored for their general well-being, weight, food and water consumption. At no time there was any evidence of toxicity ascribable to the adenoviral vectors (data not shown).

The expression of MazF and MazE in the infected tumor cells was monitored with the Maestro imaging CRi device (FIG. 8B). The imaging was performed on live mice (FIG. 8B) and outside the mouse body (FIG. 8C). This analysis confirmed that the adenoviruses indeed targeted the mutated RAS-harboring tumors and that the MazEF genes were expressed.

Example 6

An Orthotopic Model for Testing the Constructs

The present inventors have set up an orthotopic model for testing the efficacy of the therapeutic constructs system. For that purpose, the R1 cells (enterocytes that constitutively express mutated KRAS) are initially used. Additionally or alternatively, a similar system in murine cells (mc38 cell line) which express the KRAS mutated oncogene is currently designed.

Study Design:

The cells are injected into the colon of the mice, the initial volume of the tumors is measured by colonoscopy and then the treatment by a systemic injection of the viruses begins.

Since the orthotopic model is performed in C57/b1 mice, the present inventors first tested whether injection of the R1 cell line can grow to form tumors in the mouse. For that purpose, $5 \times 10^6$ R1 cells were subcutaneously injected at two sites on the backs of the mice. All the mice (5/5) developed tumors (data not shown). The viruses used for this experiment were propagated, produced and their titer was determined.

Example 7

Establishment of Stable Transfected System for KRAS Mutation

The present inventors have designed and constructed an additional vector which encodes for the mutated has having a missense mutation G13D in the KRAS (FIG. 9A). FIG. 9B schematically illustrates the luciferase construct. Next, a stable transfection to the mc38 murine colon carcinoma cells was performed and by measuring the luciferase expression the best clone was screened and selected (FIG. 9B), and as shown, the best clone was C3.

Example 8

AAV (Adeno Associated Virus)

The limitations of using adenovirus are well known, among other reasons because it causes an immune response. Therefore, the present inventors currently establish less immunogenic delivery systems; such as the AAV delivery system.

The AAV is one of the smallest 'viruses, it is a single-stranded DNA. Its properties made it one of the most promising delivery systems, partly because of its low immunogenicity, the long duration of transgenic expression, and because there are many serotypes to AAV and each one of them can infect only specific cell type, therefore the selectivity of the virus is high.

Identification of the Most Appropriate Serotype for the Different Target Cells, Especially Colorectal and Pancreatic Cancer Cells—

For that purpose, the present inventors induced tumors that derived from different cell lines in nude mice. Then a systemic single infecting of the various serotypes in several titers were conducted, and after two weeks the mice were sacrificed, the tumors were removed and the expression of the GFP was evaluated by Western blot analysis as shown in FIG. 10. According to these results, the AAV serotype 6 is the best serotype for the HT29 target cells.

The PY4-mazEF and ΔPY4-mazEF cassettes were cloned to AAV serotype 6 and the viruses are produced. These particles are evaluated in vivo, in nude mice bearing xenograft of pancreatic cancer cells.

Example 9

Establishment of a Dual System Based on Ras and P53 Responsive Elements

For establishing the dual system adenoviral vectors carrying the toxin (PY4-MazF-mcherry) and the antitoxin (RGC-MazE-IRES-GFP) were cloned under the regulation of Ras responsive elements and p53 responsive elements, respectively. FIG. 11A provides a schematic illustration of such a dual system.

Virus particles were produced, their titer was calculated and their potency was tested in vitro. Cell death was measured qualitatively by using the fluorescent microscopy and was quantified by the enzymatic MTT assay.

A594, $Ras^{mut}/p53^{wt}$; H2030, $Ras^{mut}/p53^{mut}$; H1299, $Ras^{mut}/p53^{mut}$; H1650, $Ras^{wt}/p53^{mut}$ and H1975, $Ras^{wt}/p53^{mut}$—lung cancer (LC) cell lines were used as a model system for testing the potency of the adenoviruses-based system. Mia Paca, $Ras^{mut}/p53^{mut}$; Colo357, $Ras^{mut}/p53^{mut}$ Panc1, $Ras^{mut}/p53^{mut}$ and BxPC3, $Ras^{wt}/p53'$-pancreatic cancer cell lines were tested as well.

Co-infection assays were performed, using the optimal 1:0.5 MOI ratio. The results showed decrease in the mortality of the mutated Ras cells expressing wild type (WT) p53; 36% with a titer of 7.5 MOI (FIG. 12). These results indicate that cells, which have WT p53, that expressed the toxin were protected by the antitoxin expressed under the p53 responsive element, while cells that have mutations of both genes, i.e., ras and p53, such as the SHP77, showed increased sensitivity.

The efficacy of the above dual system is tested in vitro and in vivo.

Example 10

The present inventors further tested whether the RAS responsive PY4 element works as an enhancer only in cells that carry mutation of the KRAS or even of N- and H-RAS genes. For that purpose, the ability of all the three RAS oncogenes (HRAS, NRAS, and KRAS) to activate their pathways was examined by testing their ability to stimulate their downstream transcription factors. H1299 (NRAS oncogene expressing cell line), A549 (KRAS oncogene expressing cell line) and T24 (HRAS oncogene expressing cell line) were co-transfected with PY4-luciferase and Renila luciferase plasmids. The results presented in FIG. 13A showed that the all three are able to induce the transcription of the luciferase reporter gene, with different efficiency (transcription levels of PY4-luciferase were normalized to the Renila luciferase activity).

Next, the present inventors examined the ability of those three oncogenes to induce the transcription of the toxin under the regulation of PY4 element. H1299, H2030, A549, and T24 were infected with Ad-PY4-mcherry-mazF viruses. Cell viability was measured by the MTT assay (72 hours post infection). These experiments support the previous observations by showing the different levels of toxin expression which in turn are leading to different percentage of cell viability (FIG. 13B).

Example 11

Chemically Induction of P53 Expression in CRC Cells P53 Responsive Element

Experimental Results

In order to test the ability of p53 to bind to its responsive element and stimulate transcription, HCT116 cells were transfected with RGC-mazE-IRES-GFP plasmid. Since p53 is degraded in un-activated cells, the present inventors used Quercetin, a ubiquitous bioactive plant flavonoid that is able to induce p53 phosphorylation, stabilization and total p53 protein accumulation. Another widely used p53 inducer is the antimetabolite agent 5-FU. P53 transcription activity was evaluated by measuring the expression of the downstream reporter gene, GFP. The present inventors show that the addition of Quercetin (50 μM) to the transfected HCT116 cells increased the expression of GFP by about 10 folds. Addition of 5-FU has led to significantly higher expression levels of GFP, even in lower concentration (10 μM). Furthermore, Quercetin showed severe cell toxicity (60% cell death) while no toxicity has been shown upon treatment with 5-FU, even very high doses (data not shown).

Induction of the Transcription of P53 Target Genes—

Further validation of endogenous p53 activation led the present inventors to test other canonical target genes. 5-FU (50 μM) was added to HCT116 p53 WT cells for 24 hours. Total cell lysate was prepared and subjected into Western blot analysis and at the same time RNA was prepared and used as a template for cDNA and semi-quantitative PCR was performed. The results show and confirm that protein expression, of all the target genes, correlates to the mRNA up regulation due to p53 activation. In particular a tight correlation between p21 and p53 protein levels (FIGS. 14A-C).

An in vitro colony-forming assay was performed to qualitatively and comparatively assess the sensitivity of lung cancer cells with mutated RAS to the expression of the transgene. In addition, this assay was intended to verify that MazF is well tolerated by the normal cells that do not harbor hyperactive RAS. A549 and H1650 cells were infected with 10 MOI of the adeno-PY4-mazF-mcherry and adeno-RGC-mazE-GFP viruses, in a ratio of 1:0.5 ratio, respectively. In parallel, those cells were infected with adeno-ΔPY4-mazF-mcherry and adeno-RGC-mazE-GFP viruses, in a ratio of 1:0.5, respectively. Empty vector (CMV-mcherry) infected or uninfected cells used as a control. After 7 hours, the cells were trypsinized and seeded in 3-fold dilutions and incubated for 7 days. Surviving colonies were fixed with 4% formaldehyde in PBS and stained with 0.02% crystal violet. A549 KRAS mutated and p53 WT expressing cells that were infected with PY4-mazF-mcherry and RGC-mazE-GFP viruses showed lower survival rate compared to ΔPY4-mazF-mcherry and RGC-mazE-GFP viruses infected cells. However, H1650 KRAS WT and p53 WT expressing cells that were infected with PY4-mazF-mcherry and RGC-mazE-GFP viruses showed no significant fold change in survival compared to ΔPY4-mazF-mcherry and RGC-mazE-GFP viruses infected cells (FIGS. 16A-H).

A549 cells express the mutated KRAS oncogene therefore the expression of the mazF toxin is high. In addition, these cells carry WT form of p53 that binds to its responsive element and enhances the transcription of the mazE anti-toxin. On the contrarily, H1650 cells express WT RAS, therefore the transcription of the toxin wasn't enhanced. Consequently, there was not a significant difference in toxicity between cells that were infected with viruses that carry or not the RAS responsive elements. The presence of WT p53 in these cells leads to the expression of the anti-toxin. Both the toxin and the antitoxin were visualized by the expression of the fluorescence proteins (mcherry and GFP, respectively). It is important to note the two cell lines above are different in their sensitivity to viral infections. H1650 cells showed much lower survival level then A549 line, upon infection with an empty vector (FIGS. 16A-H).

The Efficacy of mazF to Kill has been Evaluated Also in Pancreatic Cancer Cells—

PANC1, Mia Paca2, Colo357 (KRAS mutated cells) and BxPC3 (wt RAS) cell lines were seeded in 96-well plates. After 24 hours different dilutions of PY4-mazF-mcherry viruses were added. 72 hours later, cell survival was measured the enzymatic MTT assay. The results show that cells with hyperactive KRAS were more sensitive, about 50% viability in MOI of 15. However, WT RAS expressing cells showed 80% viability under the same conditions (FIG. 17).

Analysis and Discussion

In the present study vectors for cancer-directed gene delivery were constructed; "pAdEasy-Py4-SV40mP-mCherry-MazF", "pAdEasy-Py4-SV40mP-mCherry-MazF-TRES-TetR-CMVmp-MazE-IRES-EGFP", "pAdEasy-ΔPy4-SV40mP-mCherry-MazF-IRES-TetR-CMVmp-MazE-IRES-EGFP" and "pAdEasy-mCherry". Virus particles were produced and their potency was tested. Cell death was measured qualitatively by using the fluorescent microscopy and colony formation assay, and was quantified by MTT. FACS analysis using annexin V and RedDot2 dyes was performed for measuring apoptosis and dead cells, respectively. In vivo tumor formation was measured in xenograft model.

Herein, an improved approach is suggested by tightening the expression of the toxin and replacing the pro-apoptotic gene by a significant more potent toxic molecule that does not exist in human cells.

These results demonstrate a very well-regulated system that can precisely control gene delivery and expression at a specific targeted site. This system exploits the hyperactive RAS pathway, rather than inhibiting it. In addition, the results presented here demonstrate a proof-of-concept that normal tissues can be selectively spared from the toxic effects of drugs by taking advantage of their wt RAS that express the "antidote".

Thus, the MazF-MazE toxin-antitoxin system has a potential to be used as a therapeutic tool, to kill undetectable micrometastases that are a major hurdle in challenging.

This approach, of taking advantage of Ras mutation in order to selectively kill cancer cells while sparing the normal cells, either alone or preferably in conjunction with other treatment modalities can enhance efficacy while reducing toxicity.

Thus, the suggested gene therapy strategy can advance the management of human cancer, allowing a tailor-made protocol for biological treatment specific to the molecular profile of a tumor.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. American Cancer Society. Colorectal Cancer Facts & Figures. 2014.
2. Reddy M A, Langer S J, Colman M S, et al. An enhancer element responsive to ras and fms signaling pathways is composed of two distinct nuclear factor binding sites. Mol Endocrinol 1992; 6:1051-60.
3. Nabel G J. Genetic, cellular and immune approaches to disease therapy: past and future. Nat Med 2004; 10:135-41.
4. Kootstra N A, Verma I M. Gene therapy with viral vectors. Annu Rev Pharmacol Toxicol 2003; 43:413-39.
5. Verma I M, Weitzman M D. Gene therapy: twenty-first century medicine. Annu Rev Biochem 2005; 74:711-38.
6. Young L S, Searle P F, Onion D, et al. Viral gene therapy strategies: from basic science to clinical application. J Pathol 2006; 208:299-318.
7. Kaplan J M. Adenovirus-based cancer gene therapy. Curr Gene Ther 2005; 5:595-605.
8. El-Aneed A. Current strategies in cancer gene therapy. Eur J Pharmacol 2004; 498:1-8.
9. Dvory-Sobol H, Kazanov D, Arber N. Gene targeting approach to selectively kill colon cancer cells, with hyperactive K-Ras pathway. Biomed Pharmacother 2005; 59 Suppl 2:S370-4.
10. Dvory-Sobol H, Sagiv E, Kazanov D, et al. Targeting the active beta-catenin pathway to treat cancer cells. Mol Cancer Ther 2006; 5:2861-71.
11. Dvory-Sobol H, Sagiv E, Liberman E, et al. Suppression of gastric cancer cell growth by targeting the beta-catenin/T-cell factor pathway. Cancer 2007; 109:188-97.
12. Giladi N, Dvory-Sobol H, Sagiv E, et al. Gene therapy approach in prostate cancer cells using an active Wnt signal. Biomed Pharmacother 2007; 61:527-30.
13. Naumov I, Kazanov D, Lisiansky V, et al. Novel approach to abuse the hyperactive K-Ras pathway for adenoviral gene therapy of colorectal cancer. Exp Cell Res 2012; 318:160-8.
14. FitzGerald D, Pastan I. Redirecting *Pseudomonas* exotoxin. Semin Cell Biol 1991; 2:31-7.
15. Lisiansky V, Naumov I, Shapira S, et al. Gene therapy of pancreatic cancer targeting the K-Ras oncogene. Cancer Gene Ther 2012; 19:862-9.
16. Inouye M. The discovery of mRNA interferases: implication in bacterial physiology and application to biotechnology. J Cell Physiol 2006; 209:670-6.
17. Pandey D P, Gerdes K. Toxin-antitoxin loci are highly abundant in free-living but lost from host-associated prokaryotes. Nucleic Acids Res 2005; 33:966-76.
18. Engelberg-Kulka H, Amitai S, Kolodkin-Gal I, et al. Bacterial programmed cell death and multicellular behavior in bacteria. PLoS Genet 2006; 2:e135.
19. Engelberg-Kulka H, Hazan R, Amitai S. mazEF: a chromosomal toxin-antitoxin module that triggers programmed cell death in bacteria. J Cell Sci 2005; 118: 4327-32.
20. Cook G M, Robson J R, Frampton R A, et al. Ribonucleases in bacterial toxin-antitoxin systems. Biochim Biophys Acta 2013; 1829:523-31.
21. Thisted T, Sorensen N S, Wagner E G, et al. Mechanism of post-segregational killing: Sok antisense RNA interacts with Hok mRNA via its 5'-end single-stranded leader and competes with the 3'-end of Hok mRNA for binding to the mok translational initiation region. EMBO J 1994; 13:1960-8.
22. Gerdes K, Bech F W, Jorgensen S T, et al. Mechanism of postsegregational killing by the hok gene product of the parB system of plasmid R1 and its homology with the relF gene product of the *E. coli* relB operon. EMBO J 1986; 5:2023-9.
23. Zhang Y, Zhang J, Hoeflich K P, et al. MazF cleaves cellular mRNAs specifically at ACA to block protein synthesis in *Escherichia coli*. Mol Cell 2003; 12:913-23.
24. Shapira A, Shapira S, Gal-Tanamy M, et al. Removal of hepatitis C virus-infected cells by a zymogenized bacterial toxin. PLoS One 2012; 7:e32320.
25. Arber N, Sutter T, Miyake M, et al. Increased expression of cyclin D1 and the Rb tumor suppressor gene in c-K-ras transformed rat enterocytes. Oncogene 1996; 12:1903-8.
26. Okamoto M, Chono H, Kawano Y, et al. Sustained inhibition of HIV-1 replication by conditional expression of the *E. coli*-derived endoribonuclease MazF in CD4+ T cells. Hum Gene Ther Methods 2013; 24:94-103.
27. Chono H, Matsumoto K, Tsuda H, et al. Acquisition of HIV-1 resistance in T lymphocytes using an ACA-specific *E. coli* mRNA interferase. Hum Gene Ther 2011; 22:35-43.
28. Shimazu T, Mirochnitchenko O, Phadtare S, et al. Regression of Solid Tumors by Induction of MazF, a Bacterial mRNA Endoribonuclease. J Mol Microbiol Biotechnol 2014; 24:228-33.

What is claimed is:

1. A nucleic acid construct system comprising:
   first nucleic acid constructs (NA1) encoding a bacterial-derived toxin operatively linked to a first constitutive promoter and at least one Ras responsive enhancer element comprising at least one element selected from the group consisting of an Ets binding site, an Ap-1 binding site and a PY2 sequence; and
   (ii) second nucleic acid constructs (NA2) encoding a bacterial-derived anti-toxin operatively linked to a second constitutive promoter and 17 copies of a p53 wild type responsive element, wherein said 17 copies of said p53 wild type responsive element are set forth in SEQ ID NO:15;
   wherein said first and second constitutive promoters have the same ability to direct transcription; wherein said bacterial-derived toxin and said bacterial-derived anti-toxin are a bacterial type II toxin anti-toxin pair selected from the toxin-antitoxin pairs CcdB-CcdA, ParE-ParD, MazF-MazE, yafO-yafN, HicA-HicB, Kid-Kis, and Zeta-Epsilon; and wherein a greater number of said first nucleic acid constructs are provided than said second nucleic acid constructs, wherein said greater number comprises NA1 and NA2 provided at a ratio of between NA1:NA2=1:0.5 and NA1:NA2=1:0.1.

2. The nucleic acid construct system of claim 1, wherein said second constitutive promoter comprises CMV and said first promoter comprises SV40.

3. The nucleic acid construct system of claim 1, wherein said first nucleic acid construct, said second nucleic acid construct or both is adeno-virus based.

4. The nucleic acid construct system of claim 1, wherein said first nucleic acid construct, said second nucleic acid construct or both is *Lenti*-virus based.

5. The nucleic acid construct system of claim 1, wherein said Ras-responsive element comprises a PY2 sequence.

6. The nucleic acid construct system of claim 1, wherein said Ras responsive enhancer element is a K-Ras responsive enhancer element.

7. The nucleic acid construct system of claim 1, wherein said first nucleic acid construct comprises four repeats of the PY2 sequence set forth by SEQ ID NO:2 being upstream and operably linked to the SV40 minimal promoter region set forth by SEQ ID NO:4, a toxin coding sequence being downstream of and transcriptionally regulated by said SV40 minimal promoter region, an IRES sequence set forth by SEQ ID NO:7 being downstream and operably linked to said toxin coding sequence, and a Tetracycline repressor set forth by SEQ ID NO: 8 being downstream of and operably linked to said IRES sequence.

8. The nucleic acid construct system of claim 1, wherein said second nucleic acid construct comprises a CMV minimal promoter which comprises two repeats of a tetracycline operator as set forth by SEQ ID NO:9 and an antitoxin coding sequence being downstream of and operably linked to said CMV minimal promoter.

9. The nucleic acid construct system of claim 1, wherein said first promoter and said second promoter are identical.

10. The nucleic acid construct system of claim 1, wherein said first promoter and said second promoter are different.

11. The nucleic acid construct system of claim 1, wherein said toxin is mazF and said antitoxin is mazE.

12. The nucleic acid construct system of claim 1, wherein said first nucleic acid construct further comprises a repressor of a bacterial repressor-operator system, said repressor being under a transcriptional regulation of said Ras responsive enhancer element, and wherein said second nucleic acid construct comprises an operator of said bacterial repressor-operator system, such that expression of said repressor inhibits expression of said antitoxin.

13. The nucleic acid construct system of claim 12, wherein said repressor comprises the Tetracycline repressor (Tet-R) sequence, and wherein said operator comprises the tetracycline operator sequence.

14. The nucleic acid construct system of claim 12, wherein said operator comprises at least two repeats of the sequence tetracycline operator sequence.

15. A nucleic acid construct system comprising:
(i) first nucleic acid constructs (NA1) encoding a mazF operatively linked to a first constitutive promoter and at least one Ras responsive enhancer element comprising at least one element selected from an Ets binding site, Ap-1 binding site and a PY2 sequence; and
(ii) second nucleic acid constructs (NA2) encoding mazE operatively linked to a second constitutive promoter and 17 copies of a p53 wild type responsive element, wherein said 17 copies of said p53 wild type responsive element are set forth in SEQ ID NO:15;
wherein said first and second constitutive promoters have the same ability to direct transcription; and wherein a greater number of said first nucleic acid constructs are provided than said second nucleic acid constructs, wherein said greater number comprises NA1 and NA2 provided at a ratio of between NA1:NA2=1:0.5 and NA1:NA2=1:0.1.

16. A nucleic acid construct system comprising:
(i) first nucleic acid constructs (NA1) encoding a mazF operatively linked to a first constitutive promoter and at least one Ras responsive enhancer element comprising at least one element selected from an Ets binding site, Ap-1 binding site and a PY2 sequence; and
(ii) second nucleic acid constructs (NA2) encoding mazE operatively linked to a second constitutive promoter and 17 copies of a p53 wild type responsive element, wherein said 17 copies of said p53 wild type responsive element are set forth in SEQ ID NO:15;
wherein said first and second constitutive promoters are identical; and wherein a greater number of said first nucleic acid constructs are provided than said second nucleic acid constructs, wherein said greater number comprises NA1 and NA2 provided at a ratio of between NA1:NA2=1:0.5 and NA1:NA2=1:0.1.

17. A pharmaceutical composition for treatment of a tumor overexpressing Ras, said pharmaceutical composition comprising: (a) the nucleic acid construct system of claim 1, wherein said nucleic acid construct system is adeno-associated virus based and (b) a pharmaceutically acceptable vehicle.

18. A method for treating a tumor overexpressing Ras in a patient in need thereof, said method comprising introducing into the tumor cells an effective amount of the pharmaceutical composition of claim 17, wherein said tumor cells are characterized by a hyperactive RAS pathway as compared to non-tumor cells of the same tissue, thereby inhibiting tumor growth.

* * * * *